United States Patent
Madder et al.

(10) Patent No.: US 11,053,279 B2
(45) Date of Patent: Jul. 6, 2021

(54) METHODS FOR THE SITE-SELECTIVE COUPLING OF A FIRST AGENT TO A SECOND AGENT

(71) Applicant: UNIVERSITEIT GENT, Ghent (BE)

(72) Inventors: Annemieke Madder, Massemen (BE); Eirini Antonatou, Ghent (BE); Kurt Hoogewijs, Overmere (BE)

(73) Assignee: UNIVERSITEIT GENT, Ghent (BE)

( * ) Notice: Subject to any disclaimer, the term of this patent is extended or adjusted under 35 U.S.C. 154(b) by 5 days.

(21) Appl. No.: 15/737,769

(22) PCT Filed: Jun. 16, 2016

(86) PCT No.: PCT/EP2016/063854
§ 371 (c)(1),
(2) Date: Dec. 19, 2017

(87) PCT Pub. No.: WO2017/001204
PCT Pub. Date: Jan. 5, 2017

(65) Prior Publication Data
US 2019/0002494 A1    Jan. 3, 2019

(30) Foreign Application Priority Data
Jun. 29, 2015    (EP) .................................... 15174208

(51) Int. Cl.
*C07K 1/13*    (2006.01)
*C07K 1/107*    (2006.01)

(52) U.S. Cl.
CPC .............. *C07K 1/13* (2013.01); *C07K 1/1077* (2013.01)

(58) Field of Classification Search
CPC ................................ C07K 1/13; C07K 1/1077
See application file for complete search history.

(56) References Cited

U.S. PATENT DOCUMENTS

| 4,000,125 A | 12/1976 | Casagrande et al. |
| 2013/0289239 A1 | 10/2013 | Madder et al. |
| 2016/0244481 A1 | 8/2016 | Madder et al. |

FOREIGN PATENT DOCUMENTS

WO    2012085279 A2    6/2012

OTHER PUBLICATIONS

Al-Zaydi. Molecules, 2003, 8, 910-23 (Year: 2003).*
Pasceri. Chemical Communications, 2012, 48, 12077-79 (Year: 2012).*
Abdel-Khalik. Synthesis, 2001, 12, 1861-65 (Year: 2001).*
Abdel-Khalik. Zeitschift fuer Naturforschung, B: Chemical Sciences, 2000, 55(12), 1211-15 (Year: 2000).*
Costas. Bioorganic and Medicinal Chemistry Letters, 2010, 20, 6624-6627 (Year: 2010).*
Montanaro. Chemical Research in Toxicology, 2009, 22, 173-178 (Year: 2009).*
PCT International Search Report and Written Opinion dated Nov. 18, 2016 for PCT International Patent Application No. PCT/EP2016/063854, 10 pages.
Gobbini M et al: "Synthesis and Biological Evaluation of 14-Methoxy Digitalis Derivatives", Molecules Online, vol. 3, No. I, Jan. 25, 1998 (Jan. 25, 1998), pp. 20-25.
Kalaitzakis D et al: "Methylene Blue as a Photosensitizer and Redox Agent: Synthesis of 5-Hydroxy-1 H-pyrrol-2(5 H)-ones from Furans". Angewandte Chemie International Edition. vol. 54. No. 21, May 18, 2015 (May 18, 2015), pp. 6283-6287.
Li H et al: "Click Chemistry in Peptide-Based Drug Design". Molecules. vol. 18, No. 8, Aug. 16, 2013 (Aug. 16, 2013), pp. 9797-9817.
Antonatou E et al: "Singlet Oxygen-Induced Furan Oxidation for Site-Specific and Chemoselective Peptide Ligation". Chemistry—A European Journal, vol. 22, No. 25, Jun. 13, 2016 (Jun. 13, 2016), pp. 8457-8461.

* cited by examiner

*Primary Examiner* — Noble E Jarrell
(74) *Attorney, Agent, or Firm* — Amster, Rothstein & Ebenstein LLP

(57) ABSTRACT

The present invention relates to a method for site-selective coupling of a first agent to a second agent, comprising the steps of: contacting a first agent comprising at least one furan moiety with an activation signal and with a second agent comprising at least one hydrazine moiety or at least one hydroxylamine moiety, thereby activating said furan moiety to an activated furan moiety; and reacting said activated furan moiety with the hydrazine moiety or the hydroxylamine moiety, thereby site-selectively coupling said first agent to said second agent.

21 Claims, 33 Drawing Sheets
Specification includes a Sequence Listing.

n = 0, 1, 2, ...

Chemical Formula: $C_{41}H_{63}N_{11}O_9$
Exact Mass: 853,48102
Molecular Weight: 854,00722

Chemical Formula: $C_{42}H_{66}N_{11}O_9^+$
Exact Mass: 868,50395
Molecular Weight: 869,04119

Chemical Formula: $C_{44}H_{67}N_{12}O_9^+$
Exact Mass: 907,51485
Molecular Weight: 908,07723

Chemical Formula: $C_{39}H_{64}N_{13}O_9^+$
Exact Mass: 858,49445
Molecular Weight: 859,00661

Chemical Formula: $C_{54}H_{72}N_{14}O_{19}S_2$
Exact Mass: 1284,45396
Molecular Weight: 1285,36188

FIG. 36

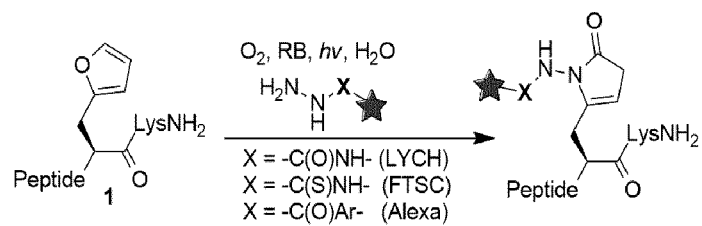

Peptide = NH-Phe-Lys-Glu-Ile-Ac

| Entry | Fluorophore (equiv.) | Solvent[a] | Labeling time (hours) / conversion (%)[b] |
|---|---|---|---|
| 1 | LYCH (1.0) | H$_2$O | 8 / 80 |
| 2 | LYCH (8.0) | pH 6.7 | 18 / 55 |
| 3 | LYCH (8.0) | pH 7.4 | 18 / 46 |
| 4 | FTSC (2.0) | H$_2$O | 18 / 4 |
| 5 | FTSC (2.0) | pH 7.4 | 48 / 68 |
| 6 | FTSC (2.0) | pH 6.7 | 48 / 60 |
| 7 | Alexa (1.0) | H$_2$O | 4 / 90 |

[a] For the reactions of peptide 1 in H$_2$O: pH 4.3 (pH of 0.5 mM or 0.2 mM for entry 7). Buffers used: 80 mM phosphate buffer pH 6.7 and 6.7 mM phosphate buffered saline pH 7.4. [b] Conversion was quantified by HPLC as consumption of oxidized species.

FIG. 42

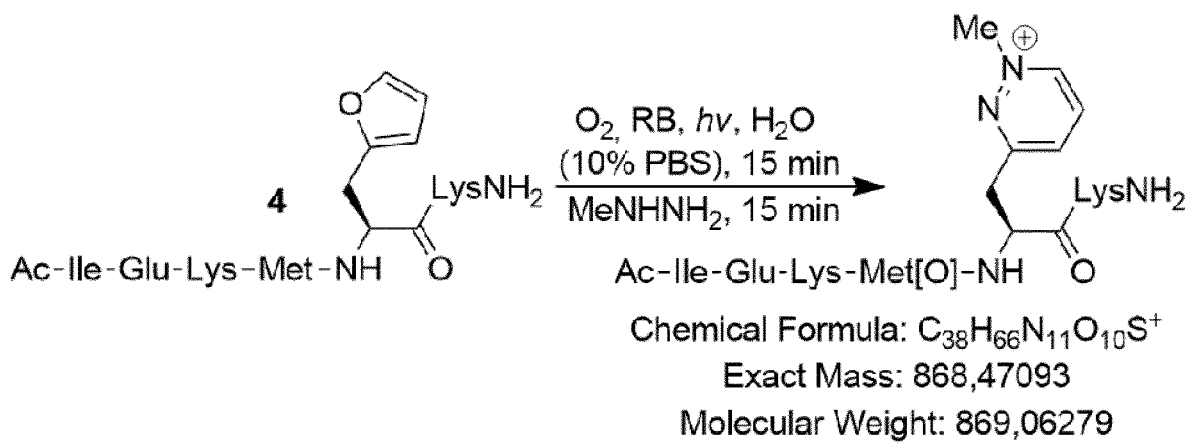

FIG. 43

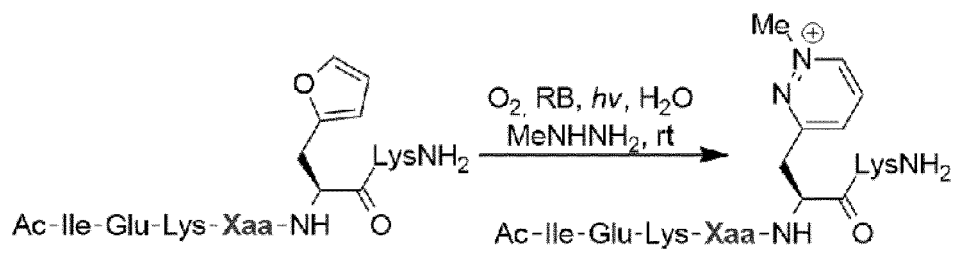

| Peptide | Xaa | Oxidation time [min] | Trapping time [min] |
| --- | --- | --- | --- |
| 2 | Trp | 50 | 15 |
| 3 | His | 30 | 30 |
| 4 | Met[a] | 15 | 15 |

Reactions were performed in MilliQ water, except for peptide 4 where 10% phosphate buffered saline was used. In all cases, 0.3 mM solutions of peptides were photooxidized at the pH of the peptides (pH = 4-5), in presence of rose Bengal (10 µM) and methyl hydrazine was added in 10-fold excess. For the irradiation a 100 W cold light lamp was used. [a] 4a contains a methionine sulfoxide residue.

FIG. 44
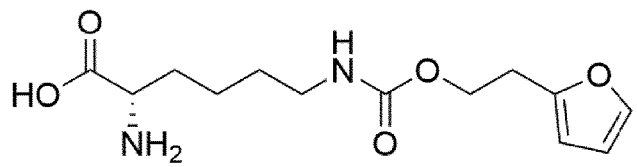
FIG. 45
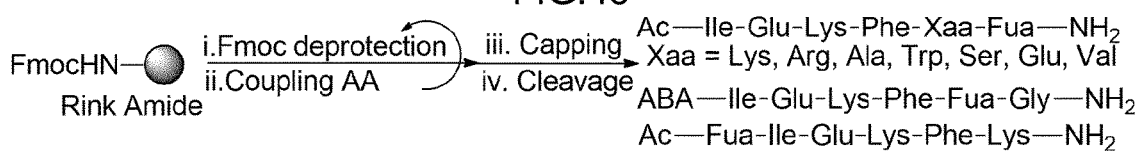
FIG. 46
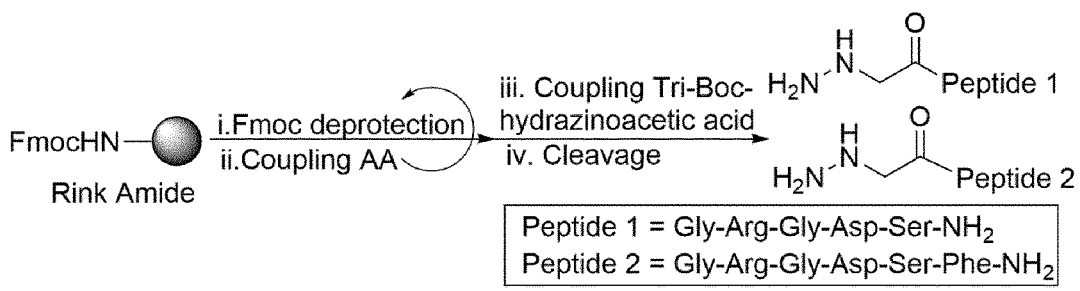
FIG. 47
A
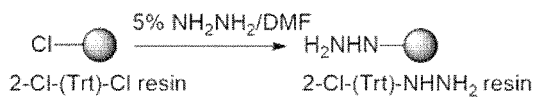
B
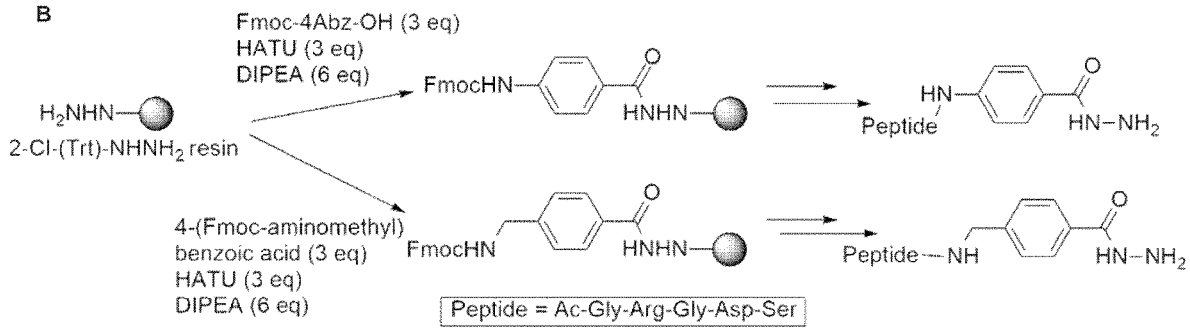

ODN1 a:  5' – CTG ACG C1C TGC- 3'
ODN1 b:  5' – CTG ACG G1G TGC- 3'

```
                       SEQUENCE LISTING

<160> NUMBER OF SEQ ID NOS: 19

<210> SEQ ID NO 1
   <211> LENGTH: 6
   <212> TYPE: PRT
   <213> ORGANISM: Artificial Sequence
   <220> FEATURE:
   <223> OTHER INFORMATION: artificial peptide
   <220> FEATURE:
   <221> NAME/KEY: MOD_RES
   <222> LOCATION: (5)..(5)
   <223> OTHER INFORMATION: L-furylalanine

<400> SEQUENCE: 1

Ile Glu Lys Phe Xaa Lys
   1               5

<210> SEQ ID NO 2
   <211> LENGTH: 6
   <212> TYPE: PRT
   <213> ORGANISM: Artificial Sequence
   <220> FEATURE:
   <223> OTHER INFORMATION: artificial peptide
   <220> FEATURE:
   <221> NAME/KEY: MOD_RES
   <222> LOCATION: (5)..(5)
   <223> OTHER INFORMATION: L-furylalanine

<400> SEQUENCE: 2

Ile Glu Lys Trp Xaa Lys
   1               5

<210> SEQ ID NO 3
   <211> LENGTH: 6
   <212> TYPE: PRT
   <213> ORGANISM: Artificial Sequence
   <220> FEATURE:
   <223> OTHER INFORMATION: artificial peptide
   <220> FEATURE:
   <221> NAME/KEY: MOD_RES
   <222> LOCATION: (5)..(5)
   <223> OTHER INFORMATION: L-furylalanine

<400> SEQUENCE: 3

Ile Glu Lys His Xaa Lys
   1               5

<210> SEQ ID NO 4
   <211> LENGTH: 6
   <212> TYPE: PRT
   <213> ORGANISM: Artificial Sequence
   <220> FEATURE:
   <223> OTHER INFORMATION: artificial peptide
   <220> FEATURE:
   <221> NAME/KEY: MOD_RES
   <222> LOCATION: (5)..(5)
   <223> OTHER INFORMATION: L-furylalanine

<400> SEQUENCE: 4

Ile Glu Lys Met Xaa Lys
   1               5
```

```
<210> SEQ ID NO 5
<211> LENGTH: 23
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (13)..(13)
<223> OTHER INFORMATION: L-furylalanine

<400> SEQUENCE: 5

Asp Thr Arg Gln Ala Arg Arg Asn Arg Arg Arg Xaa Arg Glu Arg
1               5                  10                  15

Gln Arg Ala Ala Ala Ala Arg
            20

<210> SEQ ID NO 6
<211> LENGTH: 6
<212> TYPE: PRT
<213> ORGANISM: Artificial Sequence
<220> FEATURE:
<223> OTHER INFORMATION: Artificial peptide
<220> FEATURE:
<221> NAME/KEY: MOD_RES
<222> LOCATION: (6)..(6)
<223> OTHER INFORMATION: L-furylalanine

<400> SEQUENCE: 6

Ile Glu Lys Phe Lys Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (6)..(6)
<223> OTHER INFORMATION: L-furylalanine

<400> SEQUENCE: 7

Ile Glu Lys Phe Arg Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (6)..(6)
<223> OTHER INFORMATION: L-furylalanine

<400> SEQUENCE: 8

Ile Glu Lys Phe Ala Xaa
1               5

<210> SEQ ID NO 9
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
```

```
<222> LOCATION: (6)..(6)
<223> OTHER INFORMATION: L-furylalanine

<400> SEQUENCE: 9

Ile Glu Lys Phe Ser Xaa
1               5

<210> SEQ ID NO 10
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (6)..(6)
<223> OTHER INFORMATION: L-furylalanine

<400> SEQUENCE: 10

Ile Glu Lys Phe Glu Xaa
1               5

<210> SEQ ID NO 11
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (6)..(6)
<223> OTHER INFORMATION: L-furylalanine

<400> SEQUENCE: 11

Ile Glu Lys Phe Val Xaa
1               5

<210> SEQ ID NO 12
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (6)..(6)
<223> OTHER INFORMATION: L-furylalanine

<400> SEQUENCE: 12

Ile Glu Lys Phe Trp Xaa
1               5

<210> SEQ ID NO 13
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (5)..(5)
<223> OTHER INFORMATION: L-furylalanine

<400> SEQUENCE: 13

Ile Glu Lys Phe Xaa Gly
1               5

<210> SEQ ID NO 14
<211> LENGTH: 6
```

```
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: L-furylalanine

<400> SEQUENCE: 14

Xaa Ile Glu Lys Phe Lys
1               5

<210> SEQ ID NO 15
<211> LENGTH: 5
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: hydrazine containing modification

<400> SEQUENCE: 15

Gly Arg Gly Asp Ser
1               5

<210> SEQ ID NO 16
<211> LENGTH: 6
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: hydrazine containing modification

<400> SEQUENCE: 16

Gly Arg Gly Asp Ser Phe
1               5

<210> SEQ ID NO 17
<211> LENGTH: 5
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (5)..(5)
<223> OTHER INFORMATION: 4-aminobenzoic hydrazide containing
      modification

<400> SEQUENCE: 17

Gly Arg Gly Asp Ser
1               5

<210> SEQ ID NO 18
<211> LENGTH: 5
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (5)..(5)
<223> OTHER INFORMATION: 4-aminomethyl benzoic hydrazide containing
      modification
```

```
<400> SEQUENCE: 18

Gly Arg Gly Asp Ser
1               5

<210> SEQ ID NO 19
<211> LENGTH: 5
<212> TYPE: PRT
<213> ORGANISM: Artificial Sequence
<220> FEATURE:
<223> OTHER INFORMATION: artificial peptide
<220> FEATURE:
<221> NAME/KEY: MOD_RES
<222> LOCATION: (1)..(1)
<223> OTHER INFORMATION: hydrazide containing modification

<400> SEQUENCE: 19

Gly Arg Gly Asp Ser
1               5
```

1

METHODS FOR THE SITE-SELECTIVE COUPLING OF A FIRST AGENT TO A SECOND AGENT

CROSS-REFERENCE TO RELATED APPLICATIONS

This application is a U.S. national stage entry under 35 U.S.C. § 371 of PCT International Patent Application No. PCT/EP2016/063854, filed Jun. 16, 2016, which claims priority to European Patent Application No. 16165868.7, filed Apr. 18, 2016 and European Patent Application No. 15174208.7, filed Jun. 29, 2015, the contents of which are incorporated herein by reference in their entirety.

FIELD OF THE INVENTION

The present invention is broadly in the field of bioorthogonal chemistry, more precisely in the field of orthogonal methods for coupling of a first agent to a second agent. In particular, the invention concerns a method for the site-selective coupling of a first agent, such as a peptide, to a second agent, such as a labelling agent.

BACKGROUND OF THE INVENTION

In modern biology, fluorescent probes have become an indispensable tool for studying the localization and quantity of molecules of interest such as proteins, enzymes, and nucleic acids.

The application, tracking, and visualization of peptides in an intracellular or in vivo setting can be performed through the use of site-selectively conjugated peptides. In general one makes use of the naturally available nucleophilic biomolecule functionalities such as amines, thiols, and alcohols. Selectivity problems resulting from these naturally available functionalities need to be solved by either specifically modifying N-termini or using carefully balanced orthogonal protection strategies.

To be considered an orthogonal method for conjugation of peptides, the method should fulfill a number of requirements. For instance, the method should allow the introduction of an orthogonal moiety in the bioactive peptide and the introduction of the orthogonal moiety should preserve the bioactivity of the peptide. Further, the method should allow the site-selective conjugation of the peptide at one specific position, avoiding side reactions with other biological compounds or other side chain functionalities. The method should allow the conjugation of a completely deprotected peptide under physiological conditions (e.g. aqueous solution and near-neutral pH).

Reactions at thiols are common due to their unique nucleophilicity. Also, maleimide conjugation with thiols is frequently used, but has recently been found to lead to heterogeneous conjugates due to susceptibility of the imido group to spontaneous hydrolysis. Maleimides and derivatives (bromomaleimides and aryloxymaleimides) are used for selective conjugation to peptides forming a succinimide or thiomaleimide bond respectively. Currently, there is uncertainty concerning the stability of the resulting thiomaleimide bond, which limits the applicability of the methodology so far.

In the above methodologies, conjugation is based on reaction with nucleophilic moieties in the peptide side chains. As the side chains of the natural amino acids serine, threonine, histidine, cysteine, tyrosine, glutamic acid, aspartic acid, lysine, and arginine also contain nucleophilic residues this inherently leads to orthogonality issues. Even if cysteine can be targeted quite selectively the occurrence of additional cysteines again disturbs the selectivity profile.

Therefore, methodologies have been developed for the introduction of orthogonal functional groups into peptides through the use of unnatural amino acids. This allows for a more site-selective conjugation of the peptides.

A few methodologies have been developed based on orthogonal chemistries such as carbonyl condensation reactions. However, site-selective introduction of selectively modifiable carbonyl moieties (i.e., aldehydes and ketones) into biomolecules is not straightforward. In particular, the introduction of aldehydes still represents a major synthetic hurdle. Also, the carbonyls exhibit sluggish reactivity in aqueous solutions at neutral pH. Moreover, the resulting oximes and hydrazones are hydrolytically unstable, thereby limiting the methodology. Carbonyl modifications also require the addition of catalysts (e.g. aniline) or must be performed with excess of reagents in order to reach completion.

Alternatively, the so-called "click" 1,3-dipolar cycloaddition between alkynes and azides can be used as a conjugation strategy. However, this strategy requires the use of Cu for catalysis, thereby leaving traces of Cu in the final conjugates which can interfere with biologicals assays. Furthermore, experiments have shown that the presence of free amino acid side chains leads to complexation of Cu and to sluggish click reactions with unprotected peptides. A solution to this problem involves the use of strained alkynes which are however much less straightforward to obtain, let alone to incorporate into either the peptide or the coupling reagent.

Peptide labeling based on a furan-oxidation conjugation strategy has been described previously. Deceuninck and Madder describe a strategy for peptide labeling on a solid support, relying on the incorporation of a furan moiety (Deceuninck and Madder, Chem. Commun., 2009, 21(3), 340-342). Only after linking the dye to the peptide via reductive amination, the labeled peptide was cleaved from the solid support on which the peptide was synthesized. Subsequent experiments performed by the authors have shown that the acidic cleavage from the solid support resulted in loss of fluorescence and that the methodology did not work for labeling deprotected peptides in aqueous solution.

In view of the above, there remains a need in the art to provide further and/or improved orthogonal methods for conjugation (e.g., labeling) of peptides.

SUMMARY OF THE INVENTION

The present inventors have found a method for site-selective coupling of a first agent to a second agent, comprising the steps of:
contacting a first agent comprising at least one furan moiety with an activation signal and with a second agent comprising at least one hydrazine moiety or at least one hydroxylamine moiety, thereby activating said furan moiety to an activated furan moiety; and
reacting said activated furan moiety with the hydrazine moiety or the hydroxylamine moiety, thereby site-selectively coupling said first agent to said second agent.

The present inventors have found a method for site-selective coupling of a first agent to a second agent, comprising the steps of: a) providing a first agent comprising at least one furan moiety; b) contacting said first agent with an activation signal, thereby activating said furan moiety to an activated furan moiety; c) contacting said activated furan moiety with a second agent comprising at least one hydrazine moiety or at least one hydroxylamine moiety; and d) reacting said activated furan moiety with the hydrazine moiety or the hydroxylamine moiety, thereby site-selectively coupling said first agent to said second agent.

The methods illustrating the principles of the present invention allow coupling of a first agent to a second agent with high specificity. The present methods advantageously allow the site-selective coupling of a first agent to a second agent without side reactions with other (biological) compounds or other side chain functionalities. The furan moiety also allows preserving the bioactivity of the first agent and the second agent.

Furthermore, the present methods advantageously allow the coupling of a first agent to a second agent under physiological conditions such as physiological pH, temperature, and pressure, and hence the present method can be applied intracellularly. In addition, coupling of a first agent to a second agent according to the methods of the present invention is efficient and results in high yields of conjugates. The kinetics of the present method are satisfying even at low reagent concentrations. Further, the present methods result in the formation of stable conjugates.

The present methods also allow the coupling of a first agent to a second agent in one pot. As illustrated in the example section, the one pot conversion of a furan-peptide to its labelled adduct was easily achieved. The all-in-one coupling procedure (e.g., all-in-one labeling procedure) further underscores the technical practicality of the developed methods.

The ensuing statements provide additional illustration of certain aspects and embodiments that have been disclosed in accordance with the present invention:

1. A method for site-selective coupling of a first agent to a second agent, comprising the steps of:
   a) providing a first agent comprising at least one furan moiety;
   b) contacting said first agent with an activation signal, thereby activating said furan moiety to an activated furan moiety;
   c) contacting said activated furan moiety with a second agent comprising at least one hydrazine moiety or at least one hydroxylamine moiety; and
   d) reacting said activated furan moiety with the hydrazine moiety or the hydroxylamine moiety, thereby site-selectively coupling said first agent to said second agent, wherein the first agent is a peptide.
2. The method according to statement 1, wherein the second agent comprises a hydrazine moiety or hydroxylamine moiety having a structure of Formula I, wherein $X^1$ is O, S, or N, $L^1$ is N or O, and $R^1$ is hydrogen, $C_{1-30}$alkyl, or $C_{6-20}$aryl.

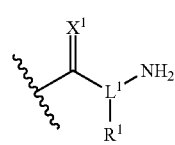

(I)

3. The method according to statement 1 or 2, wherein the second agent comprises a hydrazine moiety or hydroxylamine moiety having a structure of Formula Ia, wherein EDG is an electron donating group, and $X^1$, $L^1$, and $R^1$ have the same meaning as defined in statement 2.

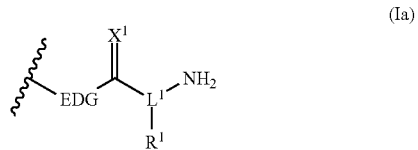

(Ia)

4. The method according to statement 3, wherein the EDG is selected from the group consisting of —NH—; —O—; —S—; $C_{1-30}$alkyl; $C_{6-20}$aryl; and $C_{5-20}$heteroaryl; wherein the $C_{1-30}$ alkyl; $C_{6-20}$aryl; or $C_{5-20}$heteroaryl group are optionally substituted with an $C_{1-6}$alkyl, $C_{3-6}$cycloalkyl, carboxyl, or $C_{1-6}$alkoxy.
5. The method according to any one of statements 1 to 4, wherein the second agent comprises a hydrazine moiety selected from the group consisting of a hydrazide, a carbohydrazide, a semicarbazide, a thiosemicarbazide, an iminosemicarbazide, a guanyl hydrazine, a dansyl hydrazine, a hydrazine, or a methyl hydrazine.
6. The method according to any one of statements 1 to 5, wherein the second agent is a labeling reagent, a small molecule, a solid surface, a biomolecule, or a polymer.
7. The method according to statement 6, wherein the biomolecule is a peptide, a polysaccharide, a lipid, a nucleic acid, or a combination thereof.
8. The method according to any one of statements 1 to 7, wherein the activation signal is singlet oxygen.
9. The method according to statement 8, wherein the singlet oxygen is generated by irradiation of air or oxygen in the presence of a sensitizer.
10. The method according to statement 9, wherein the irradiation is polychromatic light, Xenon light, or monochromatic light.
11. The method according to any one of statements 9 or 10, wherein the sensitizer is selected from the group consisting of xanthene, xanthene derivatives, fluorescein, fluorescein derivatives, methylene blue, porphyrine, porphyrine derivatives, phtalocyanine, phtalocyanine derivatives, naphthalocyanines, bacteriochlorins, texaphyrins, chlorophyll, and spirulina.
12. The method according to any one of statements 8 to 11, wherein the singlet oxygen is generated by irradiation of air or oxygen by polychromatic light in the presence of Rose bengal.
13. The method according to any one of statements 1 to 7, wherein the activation signal is a reactive oxygen species (ROS) which is generated by cells.
14. The method according to any one of statements 1 to 13, wherein the method is performed in an aqueous solution.
15. The method according to any one of statements 1 to 14, wherein the method is performed at physiological conditions, and/or at a pH ranging from about 3 to about 11, preferably at a pH ranging from about 4 to about 8.
16. A method for site-selective coupling of a first agent to a second agent, comprising the steps of:
   contacting a first agent comprising at least one furan moiety with an activation signal and with a second agent comprising at least one hydrazine moiety or at least one hydroxylamine moiety, thereby activating said furan moiety to an activated furan moiety; and
   reacting said activated furan moiety with the hydrazine moiety or the hydroxylamine moiety, thereby site-selectively coupling said first agent to said second agent, wherein the first agent is a peptide.

17. The method according to statement 16, comprising the steps of:
    a) providing a first agent comprising at least one furan moiety;
    b) contacting said first agent with an activation signal, thereby activating said furan moiety to an activated furan moiety;
    c) contacting said activated furan moiety with a second agent comprising at least one hydrazine moiety or at least one hydroxylamine moiety; and
    d) reacting said activated furan moiety with the hydrazine moiety or the hydroxylamine moiety, thereby site-selectively coupling said first agent to said second agent.
18. The method according to statement 16, comprising the steps of:
    a) providing a first agent comprising at least one furan moiety;
    b') contacting the first agent with a second agent comprising at least one hydrazine moiety or at least one hydroxylamine moiety;
    c') contacting the first agent with an activation signal, thereby activating said furan moiety to an activated furan moiety; and
    d) reacting the activated furan moiety with the hydrazine moiety or the hydroxylamine moiety, thereby site-selectively coupling the first agent to the second agent.
19. The method according to statement 16 or 18, wherein the first agent is contacted with the activation signal immediately after contacting the first agent with the second agent, such as wherein the first agent is contacted with the activation signal at most 10 minutes, or at most 5 minutes, or at most 3 minutes, or at most 1 minute, or at most 30 seconds, or at most 10 seconds, or at most 5 seconds after contacting the first agent with the second agent.
20. The method according to any one of statements 16 to 19, wherein the second agent comprises a hydrazine moiety or hydroxylamine moiety having a structure of Formula I, wherein $X^1$ is O, S, or N, $L^1$ is N or O, and $R^1$ is hydrogen, $C_{1-30}$alkyl, or $C_{6-20}$aryl.
21. The method according to any one of statements 16 to 20, wherein the second agent comprises a hydrazine moiety or hydroxylamine moiety having a structure of Formula Ia, wherein EDG is an electron donating group, and $X^1$, $L^1$, and $R^1$ have the same meaning as defined in statement 20.
22. The method according to statement 21, wherein the EDG is selected from the group consisting of —NH—; —O—; —S—; $C_{1-30}$alkyl; $C_{6-20}$aryl; and $C_{5-20}$heteroaryl; wherein the $C_{1-30}$alkyl; $C_{6-20}$aryl; or $C_{5-20}$heteroaryl group are optionally substituted with an $C_{1-6}$alkyl, $C_{3-6}$cycloalkyl, carboxyl, or $C_{1-6}$alkoxy.
23. The method according to any one of statements 16 to 22, wherein the second agent comprises a hydrazine moiety selected from the group consisting of a hydrazide, a carbohydrazide, a semicarbazide, a thiosemicarbazide, an iminosemicarbazide, a guanyl hydrazine, a dansyl hydrazine, a hydrazine, or a methyl hydrazine.
24. The method according to any one of statements 16 to 23, wherein the second agent is a labeling reagent, a small molecule, a solid surface, a biomolecule, or a polymer.
25. The method according to statement 24, wherein the biomolecule is a peptide, a polysaccharide, a lipid, a nucleic acid, or a combination thereof.
26. The method according to any one of statements 16 to 25, wherein the activation signal is singlet oxygen.
27. The method according to statement 26, wherein the singlet oxygen is generated by irradiation of air or oxygen in the presence of a sensitizer.
28. The method according to statement 27, wherein the irradiation is polychromatic light, Xenon light, or monochromatic light.
29. The method according to any one of statements 27 or 28, wherein the sensitizer is selected from the group consisting of xanthene, xanthene derivatives, fluorescein, fluorescein derivatives, methylene blue, porphyrine, porphyrine derivatives, phtalocyanine, phtalocyanine derivatives, naphthalocyanines, bacteriochlorins, texaphyrins, cholorophyll, and spirulina.
30. The method according to any one of statements 26 to 29, wherein the singlet oxygen is generated by irradiation of air or oxygen by polychromatic light in the presence of Rose bengal.
31. The method according to any one of statements 16 to 25, wherein the activation signal is a reactive oxygen species (ROS) which is generated by cells.
32. The method according to any one of statements 16 to 31, wherein the method is performed in an aqueous solution.
33. The method according to any one of statements 16 to 32, wherein the method is performed at physiological conditions, and/or at a pH ranging from about 3 to about 11, preferably at a pH ranging from about 4 to about 8.

The present invention will now be further described. In the following passages, different aspects of the invention are defined in more detail. Each aspect so defined may be combined with any other aspect or aspects unless clearly indicated to the contraryl. In particular, any feature indicated as being preferred or advantageous may be combined with any other feature or features indicated as being preferred or advantageous.

BRIEF DESCRIPTION OF THE FIGURES

FIG. 36 represents an overview of reaction conditions for labeling of furan-peptide 1 using different fluorophores.

FIG. 42 represents a schematic overview illustrating the synthesis of the pyridazinium cation modified peptide synthesized from furan-peptide 4 and methylhydrazine.

FIG. 43 represents an overview of optimized conditions for the photo-oxidation of peptides containing Trp, His, Met, or Met sulfoxide residue.

FIG. 44 represents a furan modified amino acid (faa) to be used in a method according to an embodiment of the present invention.

FIG. 45 represents a schematic overview illustrating the synthesis of C-terminal, internal, and N-terminal furan-peptides to be used in methods according to embodiments of the present invention.

FIG. 46 represents a schematic overview illustrating the synthesis of N-terminal hydrazine peptides to be used in methods according to embodiments of the present invention.

FIG. 47 represents a schematic overview illustrating the synthesis of C-terminal hydrazide peptides (next to an aromatic ring) to be used in methods according to embodiments of the present invention. FIG. 47A illustrates the preparation of 2-Cl-(Trt)-NHNH$_2$ resin. FIG. 47B illustrates the synthesis of C-terminal hydrazide peptides by coupling of 4-(Fmoc-amino)benzoic acid (upper panel) or 4-(Fmoc-aminomethyl) benzoic acid (lower panel).

DETAILED DESCRIPTION OF THE INVENTION

Figure 1:
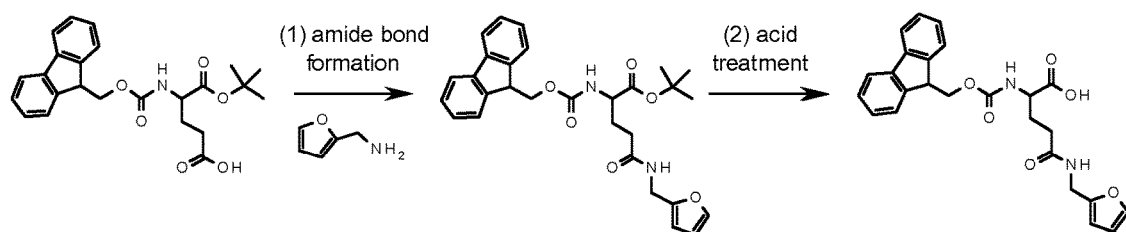
FIG. 1 represents a schematic overview illustrating the synthesis of a furan amino acid from a commercially available furyl amine derivative and a glutamic acid derivative. (1): amide bond formation; (2): acid treatment.

Before the present method and products of the invention are described, it is to be understood that this invention is not limited to particular methods, components, products or combinations described, as such methods, components, products and combinations may, of course, varyl. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contraryl. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

A problem in bioorthogonal peptide conjugation (e.g., labeling) is the difficulty to incorporate orthogonal functional groups such as a carbonyl moiety or strained alkyne into the peptide. Also, current techniques using a furan moiety are unsatisfactory since they only allow labeling of a furan-peptide on a solid support.

Unexpectedly, the present inventors have found that a hydrazine moiety may be used for selective and specific coupling of a first agent comprising a furan moiety to a second agent which comprises a hydrazine moiety.

The present invention concerns realizing 1) the activation of a furan moiety to a reactive intermediate which is stable and can be characterized if needed before further reaction, and 2) the coupling of the reactive intermediate to a second agent comprising a hydrazine moiety or a hydroxylamine moiety.

In particular, the coupling method leads to the generation of covalently connected first agent-second agent conjugates. This coupling method is useful in modification of peptides or polymers, e.g., biopolymers (peptides, proteins, DNA), for example in tagging and labeling of peptides or nucleic acids, production of antibody-drug conjugates, coupling of peptides to solid supports, coupling of peptides to small molecules, peptide-peptide ligation strategies, etc. The first agent-second agent conjugates are valuable tools in diagnostics and therapeutics, and in research. For instance, the present method allows fluorescent bioimaging studies in living cells by labeling a protein of interest with a fluorescent marker, which allows for the selective and real-time detection of protein localization, trafficking, and activities.

In contrast to other orthogonal functional groups that can be incorporated into biomolecules such as a carbonyl moiety or strained alkyne, the furan moiety can be easily incorporated into peptides for instance through genetic expression. Furthermore, furan moieties are absent from biological settings, whereas carbonyls can be found intracellularly.

Many commercially available fluorescent reagents contain a hydrazine, in particular a hydrazide, or fluorescent hydrazines can be easily prepared from commercially available fluorescent labeling reagents, thereby allowing a broad range of labeling applications.

A first aspect of the invention relates to a method for site-selective coupling of a first agent to a second agent, comprising the steps of:
contacting a first agent comprising at least one furan moiety with an activation signal and with a second agent comprising at least one hydrazine moiety or at least one hydroxylamine moiety, thereby activating said furan moiety to an activated furan moiety; and
reacting said activated furan moiety with the hydrazine moiety or the hydroxylamine moiety, thereby site-selectively coupling said first agent to said second agent.

Preferably, the present invention relates to a method for site-selective coupling of a first agent to a second agent, comprising the steps of: a) providing a first agent comprising at least one furan moiety; b) contacting said first agent with an activation signal, thereby activating said furan moiety to an activated furan moiety; c) contacting said activated furan moiety with a second agent comprising at least one hydrazine or at least one hydroxylamine moiety; and d) reacting said activated furan moiety with the hydrazine or hydroxylamine moiety, thereby site-selectively coupling said first agent to said second agent. The methods as taught herein are preferably performed in vitro.

The present invention provides methods for the site-selective coupling of a first agent to a second agent.

The term "coupling" or "conjugating" refers to linking a first agent to a second agent with a covalent bond.

The terms "site-selective coupling" or "site-specific coupling", as opposed to non-selective or non-specific coupling, refer to the coupling of one or more monomers present or introduced in one or more determined positions of a first agent (e.g., one or more furan amino acids present or introduced in one or more determined positions of the furan-peptide) to a second agent.

The term "first agent" refers to any agent capable of comprising at least one furan moiety. In the context of the present invention, the nature of the first agent is not limited as long as at least one furan moiety can be present in the first agent (e.g., is part of a commercially available first agent) or can be introduced in the first agent such as by a chemical reaction, by recombinant molecular genetic techniques, or by a cell or translation system.

The term "furan moiety", "furan", "furyl" or "furyl-moiety" relates to a heterocyclic organic compound or functional group of Formula (IIa) or (IIb) consisting of a five-membered aromatic ring with four carbon atoms and one oxygen atom.

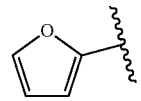

(IIa)

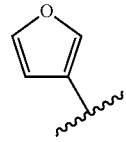

(IIb)

The term "second agent" refers to any agent which is of interest to be coupled to a first agent. In the context of the present invention, the nature of the second agent is not limited as long as the second agent comprises at least one hydrazine moiety or at least one hydroxylamine moiety. In the methods as taught herein, the hydrazine or hydroxylamine moiety may be part of the second agent (e.g., may be naturally present in the second agent or may be part of a commercially available second agent) or may be introduced into the second agent such as by a chemical reaction.

The term "hydrazine moiety" as used herein refers to any moiety comprising a nitrogen-nitrogen single covalent bond (i.e., N—N bond). The hydrazine moiety may be chemically linked to the (remainder of the) second agent with one or both nitrogen atoms. Preferably, the hydrazine moiety may be chemically linked to the (remainder of the) second agent with one nitrogen atom only.

The term "hydroxylamine moiety" as used herein refers to any moiety comprising a nitrogen-oxygen single covalent bond (i.e., N—O bond). The hydroxylamine moiety may be chemically linked to the (remainder of the) second agent with the nitrogen atom and/or oxygen atom. Preferably, the hydroxylamine moiety is chemically linked to the (remainder of the) second agent with the oxygen atom.

In certain preferred embodiments, the hydrazine moiety or the hydroxylamine moiety may be chemically linked to the (remainder of the) second agent by binding to (a) carbon atom(s). In certain embodiments, the hydrazine moiety or the hydroxylamine moiety may be chemically linked to the (remainder of the) second agent by binding to (a) sulfur atom(s).

In certain embodiments of the methods as taught herein, the second agent may comprise a hydrazine moiety or hydroxylamine moiety having a structure of Formula I or Ia, wherein $X^1$ is O, S, or N, $L^1$ is N or O, and $R^1$ is hydrogen, $C_{1-30}$alkyl, or $C_{6-20}$aryl. Preferably, $X^1$ is O or S, $L^1$ is N or O, and $R^1$ is hydrogen or methyl. More preferably, $X^1$ is O or S, $L^1$ is N or O, and $R^1$ is hydrogen.

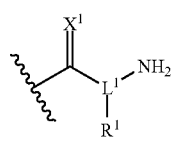

(I)

In certain embodiments of the methods as taught herein, the second agent may comprise a hydrazine moiety or hydroxylamine moiety having a structure of Formula I or Ia, wherein $X^1$ is O, S, or N, $L^1$ is N or O, and $R^1$ is hydrogen, $C_{1-12}$alkyl, or $C_{6-10}$aryl. In certain embodiments of the methods as taught herein, the second agent may comprise a hydrazine moiety or hydroxylamine moiety having a structure of Formula I or Ia, wherein $X^1$ is O, S, or N, $L^1$ is N or O, and $R^1$ is hydrogen, $C_{1-6}$alkyl, or $C_{6-10}$aryl. In certain embodiments of the methods as taught herein, the second agent may comprise a hydrazine moiety or hydroxylamine moiety having a structure of Formula I or Ia, wherein $X^1$ is O, S, or N, $L^1$ is N or O, and $R^1$ is hydrogen or methyl. In certain embodiments of the methods as taught herein, the second agent may comprise a hydrazine moiety or hydroxylamine moiety having a structure of Formula I or Ia, wherein $X^1$ is O, S, or N, $L^1$ is N or O, and $R^1$ is hydrogen.

In certain embodiments of the methods as taught herein, the second agent may comprise a hydrazine moiety having a structure of Formula Ib or Id, wherein $X^1$ is O, S, or N, and $R^1$ is hydrogen, $C_{1-30}$alkyl, or $C_{6-20}$aryl. In certain embodiments of the methods as taught herein, the second agent may comprise a hydrazine moiety having a structure of Formula Ib or Id, wherein $X^1$ is O, S, or N, and $R^1$ is hydrogen, $C_{1-12}$alkyl, or $C_{6-10}$aryl. In certain embodiments of the methods as taught herein, the second agent may comprise a hydrazine moiety having a structure of Formula Ib or Id, wherein $X^1$ is O, S, or N, and $R^1$ is hydrogen, $C_{1-6}$alkyl, or $C_{6-10}$aryl. Preferably, $X^1$ is O or S, and $R^1$ is hydrogen or methyl. More preferably, $X^1$ is O or S, and $R^1$ is hydrogen.

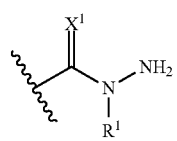

(Ib)

In certain embodiments of the methods as taught herein, the second agent may comprise a hydrazine moiety having a structure of Formula Ic or Ie, wherein $X^1$ is O, S, or N. Preferably, $X^1$ is O or S.

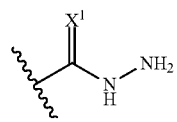

(Ic)

In certain embodiments of the methods as taught herein, the second agent may comprise a hydrazine moiety or hydroxylamine moiety having a structure of Formula Ia, wherein EDG is an electron donating group, and $X^1$, $L^1$, and $R^1$ have the same meaning as defined herein.

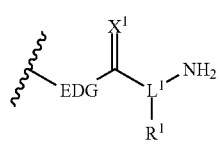

(Ia)

In certain embodiments of the methods as taught herein, the second agent may comprise a hydrazine moiety having a structure of Formula Id, wherein EDG is an electron donating group; $X^1$ is O, S, or N; and $R^1$ is hydrogen, $C_{1-30}$alkyl, or $C_{6-20}$aryl.

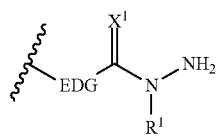

(Id)

In certain embodiments of the methods as taught herein, the second agent may comprise a hydrazine moiety having a structure of Formula Id, wherein EDG is an electron donating group; $X^1$ is O, S, or N; and $R^1$ is hydrogen, $C_{1-12}$alkyl, or $C_{6-10}$aryl. In certain embodiments of the methods as taught herein, the second agent may comprise a hydrazine moiety having a structure of Formula Id, wherein EDG is an electron donating group; $X^1$ is O, S, or N; and $R^1$ is hydrogen, $C_{1-6}$alkyl, or $C_{6-10}$aryl. Preferably, $X^1$ is O or S, and $R^1$ is hydrogen or methyl. More preferably, $X^1$ is O or S, and $R^1$ is hydrogen.

In certain embodiments of the methods as taught herein, the second agent may comprise a hydrazine moiety having a structure of Formula Ie, wherein EDG is an electron donating group; $X^1$ is O, S, or N. Preferably, $X^1$ is O or S.

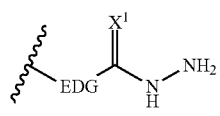

(Ie)

In certain embodiments, the EDG may be selected from the group consisting of —NH—; —O—; —S—; $C_{1-30}$alkyl; $C_{6-20}$aryl; and $C_{5-20}$heteroaryl; wherein the $C_{1-30}$alkyl; $C_{6-20}$aryl; or $C_{5-20}$heteroaryl group are optionally substituted with an $C_{1-6}$alkyl, $C_{3-6}$cycloalkyl, carboxyl, or $C_{1-6}$alkoxy. In certain embodiments, the EDG may be selected from the group consisting of —NH—; $C_{1-30}$alkyl;

$C_{6-20}$aryl; and $C_{5-20}$heteroaryl; wherein the $C_{1-30}$alkyl; $C_{6-20}$aryl; or $C_{5-20}$heteroaryl group are optionally substituted with an $C_{1-6}$alkyl, $C_{3-6}$cycloalkyl, carboxyl, or $C_{1-6}$alkoxy. In certain embodiments, the EDG may be selected from the group consisting of —NH—; $C_{1-30}$alkyl; $C_{6-20}$aryl; and $C_{5-20}$heteroaryl.

In certain embodiments, the EDG may be selected from the group consisting of —NH—; —O—; —S—; $C_{1-12}$alkyl; $C_{6-10}$aryl; and $C_{5-10}$heteroaryl; wherein the $C_{1-12}$alkyl; $C_{6-10}$aryl; or $C_{5-10}$heteroaryl group are optionally substituted with an $C_{1-6}$alkyl, $C_{3-6}$cycloalkyl, carboxyl, or $C_{1-6}$alkoxy. In certain embodiments, the EDG may be selected from the group consisting of —NH—; $C_{1-12}$alkyl; $C_{6-10}$aryl; and $C_{5-10}$heteroaryl; wherein the $C_{1-12}$alkyl; $C_{6-10}$aryl; or $C_{5-10}$heteroaryl group are optionally substituted with an $C_{1-6}$alkyl, $C_{3-6}$cycloalkyl, carboxyl, or $C_{1-6}$alkoxy. In certain embodiments, the EDG may be selected from the group consisting of —NH—; $C_{1-12}$alkyl; $C_{6-10}$aryl; and $C_{5-10}$heteroaryl.

In the methods as taught herein, the electron donating group may be part of the second agent (e.g., may be naturally present in the second agent or may be part of a commercially available second agent) or may be introduced into the second agent by a chemical reaction.

The present inventors have surprisingly found that a hydrazine or hydroxylamine moiety comprising an electron donating group, such as the aforementioned electon donating groups, advantageously allows faster coupling of the first agent to the second agent. The faster coupling may be due to increasing the stability of intermediate compounds formed during reaction of the activated furan-peptide with the hydrazine moiety or hydroxylamine moiety of the second agent. For instance, the presence of an electron donating group may stabilize the intermediate derived from the reaction of a hydrazide (comprised in a second agent) with a ketoenal (comprised in a first agent) to form a hydrazone intermediate which is stabilized by an electron donating group (EDG) as shown below.

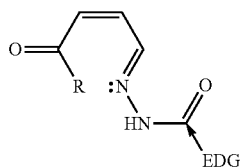

In certain embodiments of the methods as taught herein, the hydrazine moiety may have a structure of Formula If or Ig, wherein the EDG is as defined herein.

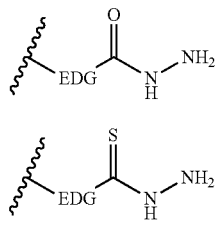

In certain embodiments of the methods as taught herein, the second agent may comprise a hydrazine moiety selected from the group consisting of a hydrazide, a carbohydrazide, a semicarbazide, a thiosemicarbazide, an iminosemicarbazide, a guanyl hydrazine, a dansyl hydrazine, a hydrazine, or a methyl hydrazine. In certain embodiments, the second agent may comprise a hydrazide moiety. In certain embodiments the second agent may comprise a carbohydrazide. In certain embodiments the second agent may comprise a semicarbazide moiety or thiosemicarbazide moiety.

The term "hydrazide moiety" as used herein refers to a moiety having a structure of Formula Ih.

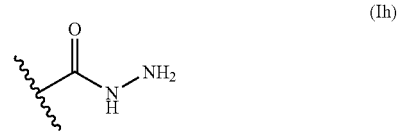 [SMILES: *C(=O)NN]

The term "carbohydrazide moiety" as used herein refers to a moiety having a structure of Formula Ij.

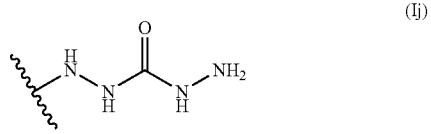 [SMILES: *NNC(=O)NN]

The term "semicarbazide moiety" as used herein refers to a moiety having a structure of Formula Ik.

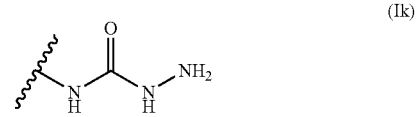 [SMILES: *NC(=O)NN]

The term "thiosemicarbazide moiety" as used herein refers to a moiety having a structure of Formula Im.

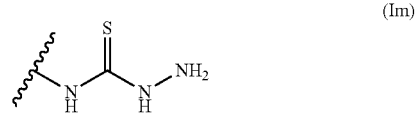 [SMILES: *NC(=S)NN]

The term "iminosemicarbazide moiety" as used herein refers to a moiety having a structure of Formula In.

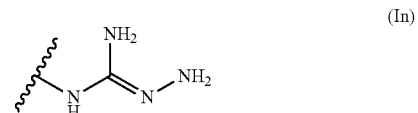

The term "guanyl hydrazine" as used herein refers to a moiety having a structure of Formula Ip.

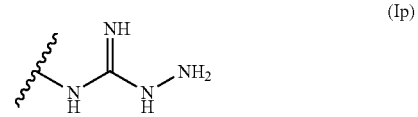 [SMILES: *NC(=N)NN]

The term "dansyl hydrazine" as used herein refers to a moiety having a structure of Formula Iq.

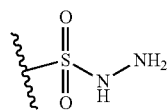

The term "hydrazine" as used herein refers to a moiety having the structure —NH—NH$_2$.

The term "methyl hydrazine" as used herein refers to a moiety having the structure —N(CH$_3$)—NH$_2$.

It is to be understood that in the structures of Formula Ia, Id, Ie, If, Ig, Ij, Ik, Im, In, and Ip as defined herein the electron donating group, for instance —NH—, can be part of a heteroaryl as defined herein.

The term "alkyl", as a group or part of a group, refers to a hydrocarbyl group of Formula $C_nH_{2n+1}$ wherein n is a number of at least 1. Alkyl groups may be linear, or branched and may be substituted as indicated herein. Generally, the alkyl groups comprise from 1 to 30 carbon atoms, preferably from 1 to 6 or 12 carbon atoms, more preferably from 1 to 6 carbon atoms, even more preferably 1, 2, 3, 4, 5, or 6 carbon atoms. When a subscript is used herein following a carbon atom, the subscript refers to the number of carbon atoms that the named group may contain.

For example, the term "$C_{1-30}$alkyl", as a group or part of a group, refers to a hydrocarbyl group of Formula $C_nH_{2n+1}$ wherein n is a number ranging from 1 to 30. Thus, for example, $C_{1-30}$alkyl groups include all linear, or branched alkyl groups having 1 to 30 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octadecyl and its isomers, nonadecyl and its isomers, icosyl and its isomers, henicosyl and its isomers, docosyl and its isomers, tricosyl and its isomers, tetracosyl and its isomers, pentacosyl and its isomers, hexacosyl and its isomers, heptacosyl and its isomers, octacosyl and its isomers, nonacosyl and its isomers, triacontyl and its isomers.

For example, the term "$C_{1-12}$alkyl", as a group or part of a group, refers to a hydrocarbyl group of Formula $C_nH_{2n+1}$ wherein n is a number ranging from 1 to 12. Thus, for example, $C_{1-12}$alkyl groups include all linear, or branched alkyl groups having 1 to 12 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers, undecyl and its isomers, and dodecyl and its isomers.

For example, $C_{1-6}$alkyl groups include all linear or branched alkyl groups having 1 to 6 carbon atoms, and thus include for example methyl, ethyl, n-propyl, i-propyl, 2-methyl-ethyl, butyl and its isomers (e.g. n-butyl, i-butyl and t-butyl); pentyl and its isomers, and hexyl and its isomers.

The term "cycloalkyl", as a group or part of a group, refers to a cyclic alkyl group, that is a monovalent, saturated, hydrocarbyl group having 1 or more cyclic structures, and comprising from 3 to 12 carbon atoms, more preferably from 3 to 9 carbon atoms, more preferably from 3 to 6 carbon atoms, still more preferably from 5 to 6 carbon atoms. Cycloalkyl includes all saturated hydrocarbon groups containing 1 or more rings, including monocyclic or bicyclic groups. The further rings of multi-ring cycloalkyls may be fused, bridged, and/or joined through one or more spiro atoms. The term "$C_{3-6}$cycloalkyl", as used herein, refers to a cyclic alkyl group comprising from 3 to 6 carbon atoms, more preferably from 5 to 6 carbon atoms. Non-limiting examples of $C_{3-6}$cycloalkyl groups include cyclopropyl, cyclobutyl, cyclopentyl, cyclohexyl. Cycloalkyl groups may also be considered to be a subset of homocyclic rings discussed hereinafter.

The term "homocyclic ring" as a group or part of a group, refers to a ring wherein the ring atoms comprise only carbon atoms. Non limiting examples of homocyclic rings include cycloalkyl, cycloalkenyl, with cycloalkyl being preferred. Where a ring carbon atom is replaced with a heteroatom, preferably nitrogen, oxygen of sulfur, the heteroatom-containing ring resultant from such a replacement is referred to herein as a heterocyclic ring. More than one carbon atom in a ring may be replaced so forming heterocyclic ring having a plurality of heteroatoms.

The term "$C_{1-6}$alkoxy" or "$C_{1-6}$alkyloxy", as a group or part of a group, refers to a group having the Formula —OR$^a$ wherein R$^a$ is $C_{1-6}$alkyl as defined herein above. Non-limiting examples of suitable $C_{1-6}$alkoxy include methoxy, ethoxy, propoxy, isopropoxy, butoxy, isobutoxy, sec-butoxy, tert-butoxy, pentyloxy and hexyloxy.

The term "aryl" as used herein refers to a polyunsaturated, aromatic hydrocarbyl group having a single ring (i.e. phenyl) or multiple aromatic rings fused together (e.g. naphthalene) or linked covalently, typically containing 6 to 20 atoms; preferably 6 to 10, wherein at least one ring is aromatic. The aromatic ring may optionally include one to two additional rings (either cycloalkyl, heterocyclyl, or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7- or 8-azulenyl, naphthalen-1- or -2-yl, 4-, 5-, 6 or 7-indenyl, 1-2-, 3-, 4- or 5-acenaphtylenyl, 3-, 4- or 5-acenaphtenyl, 1-, 2-, 3-, 4- or 10-phenanthryl, 1- or 2-pentalenyl, 4- or 5-indanyl, 5-, 6-, 7- or 8-tetrahydronaphthyl, 1,2,3,4-tetrahydronaphthyl, 1,4-dihydronaphthyl, 1-, 2-, 3-, 4- or 5-pyrenyl. Where a carbon atom in an aryl group is replaced with a heteroatom, the resultant ring is referred to herein as a heteroaryl ring.

The term "heteroaryl" as used herein by itself or as part of another group refers but is not limited to 5 to 20 carbon-atom aromatic rings or ring systems containing 1 to 2 rings which are fused together or linked covalently, typically containing 5 to 6 atoms; at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized.

In the compounds defined herein, the term "carboxyl" refers to the group —COOH.

In an embodiment, the methods as described herein comprise (the step of) a) providing a first agent comprising at least one furan moiety.

In certain embodiments, the first agent comprising at least one furan moiety is a first agent comprising at least one furan moiety of Formula IIa.

In certain embodiments, the first agent may be a peptide, a small molecule, or a polymer.

In certain embodiments, the first agent may be a peptide or a polymer.

The terms "peptide", "polypeptide" or "protein" are interchangeably used herein and refer to any natural, synthetic or recombinant molecule comprising amino acids joined together by peptide bonds between adjacent amino acid residues. A "peptide bond", "peptide link" or "amide bond" is a covalent bond formed between two amino acids when the carboxyl group of one amino acid reacts with the amino group of the other amino acid, thereby releasing a molecule of water. The peptide can be from any source, e.g. a naturally occurring peptide, a chemically synthesized peptide, a peptide produced by recombinant molecular genetic techniques, or a peptide from a cell or translation system. In embodiments, the peptide may be a linear chain or may be folded into a globular form. It is not intended that a peptide be limited by the number of amino acids joined together by peptide bonds. Furthermore, it is not intended that a peptide be limited by possessing or not possessing any particular biological activity.

The term "polymer" as used herein refers to a macromolecule composed of many covalently bonded repeated subunits.

In certain embodiments, the first agent may be a synthetic polymer such as polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS) high impact polystyrene (HIPS), polyamides (PA) (Nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), and polyurethanes (PU).

In certain embodiments, the first agent may be a natural polymer (i.e., biopolymer) such as a polynucleotide (i.e., RNA and DNA); a polypeptide; or a polysaccharide.

The term "biopolymer" generally refers to polymers produced by living organisms. In other words, they are polymeric biomolecules.

In certain embodiments, the first agent may be a lipid.

In certain embodiments, the first agent may be a small molecule. The small molecule may be a furyl propionate such as ethyl 3-(furan-2-yl)propionate.

In certain preferred embodiments, the first agent may be a peptide.

In the context of the present invention, the term "furan-peptide" refers to any peptide comprising a furan moiety.

In certain embodiments, the present invention provides a method for site-selective coupling of a first agent to a second agent, comprising the steps of:
  contacting a first agent comprising at least one furan moiety with an activation signal and with a second agent comprising at least one hydrazine moiety or at least one hydroxylamine moiety, thereby activating said furan moiety to an activated furan moiety; and
  reacting said activated furan moiety with the hydrazine moiety or the hydroxylamine moiety, thereby site-selectively coupling said first agent to said second agent, wherein the first agent is a peptide.

Accordingly, in certain embodiments, the present invention provides a method for site-selective coupling of a peptide to a second agent, comprising the steps of:
  contacting a furan-peptide, said furan-peptide comprising at least one furan moiety, with an activation signal and with a second agent comprising at least one hydrazine moiety or at least one hydroxylamine moiety, thereby activating said furan-peptide to an activated furan-peptide; and
  reacting said activated furan-peptide with the hydrazine moiety or the hydroxylamine moiety, thereby site-selectively coupling said activated furan-peptide to said second agent.

In certain embodiments, the present invention relates to a method for site-selective coupling of a first agent to a second agent, comprising the steps of: a) providing a first agent comprising at least one furan moiety; b) contacting said first agent with an activation signal, thereby activating said furan moiety to an activated furan moiety; c) contacting said activated furan moiety with a second agent comprising at least one hydrazine or at least one hydroxylamine moiety; and d) reacting said activated furan moiety with the hydrazine or hydroxylamine moiety, thereby site-selectively coupling said first agent to said second agent, wherein the first agent is a peptide.

Hence, in certain embodiments, the present invention provides a method for site-selective coupling of a peptide to a second agent, comprising the steps of:
  a) providing a furan-peptide, said furan-peptide comprising at least one furan moiety;
  b) contacting the furan-peptide with an activation signal, thereby activating said furan-peptide to an activated furan-peptide;
  c) contacting said activated furan-peptide with a second agent comprising at least one hydrazine moiety or at least one hydroxylamine moiety; and
  d) reacting the activated furan-peptide with the hydrazine moiety or the hydroxylamine moiety, thereby site-selectively coupling the activated furan-peptide to the second agent. Preferably, the method is performed in an aqueous solution The methods as taught herein thus may make use of furan-peptides.

In certain embodiments, the furan-peptide is a peptide comprising a furan moiety of Formula IIa.

The furan-peptides as taught herein comprise at least one furan moiety. The furan-peptides may comprise more than one, such as, for instance, 2, 3, 4, 5, 6, 7, 8, 9, 10, 11, 12, 13, 14, 15, 16, 17, 18, 19 or 20 furan moieties. In certain embodiments, the furan-peptide may comprise only one furan moiety. The furan moieties as taught herein can be located on any position in the furan-peptide, such as, for instance, N-terminally, C-terminally or internally. For instance, in case of more than one furan moiety, a first furan moiety may be located C-terminally and a further furan moiety may be located internally and/or N-terminally in a furan-peptide.

The furan-peptides as taught herein can be obtained by any suitable method known by the person skilled in the art. In a preferred method, the furan-peptides as taught herein are obtained by incorporating at least one furan moiety during solid-phase peptide synthesis (SPPS) of a peptide. Solid-phase peptide synthesis is a method that is widely used to chemically synthesize peptides (see, e.g., Merrifield, 1963, JACS, 85, 2149-2154) and can be adapted to produce furan-peptides. This technique typically comprises two stages: the first stage of solid phase peptide synthesis (SPPS) includes the assembly of a peptide chain using protected amino acid derivatives on a solid support via repeated cycles of coupling-deprotection. The free N-terminal amine of a solid-phase attached peptide can then be coupled to the C-terminal carboxyl of a single N-protected amino acid unit, e.g., a furan amino acid. This unit is then deprotected, revealing a new N-terminal amine to which a further amino acid may possibly be attached. While the peptide is being synthesized usually by stepwise methods, all soluble reagents can be removed from the peptide-solid support matrix by filtration and washed away at the end of each coupling step. In the second stage of SPPS, the peptide is cleaved from the support and side-chain protecting groups are removed to produce the peptide, e.g., a furan-peptide.

In certain embodiments, the methods as described herein may comprise prior to step (a), the step of producing furan-peptides by incorporating at least one furan amino acid or furan moiety into a peptide during solid-phase peptide synthesis (SPPS) of said peptide.

There are two major used forms of solid phase peptide synthesis: Fmoc (Carpino et al., 1972, *J. Org. Chem.*, 37, 3404-3409), in which a base labile alpha-amino protecting group is used, and t-Boc, in which an acid labile protecting group is used. Each method involves different solid support resins and amino acid side chain protection and consequent cleavage/deprotection steps. For additional details regarding peptide synthesis, see the following publications and references cited within: Crick et al., 1961, *Nature*, 192, 1227-32; Hofmann et al., 1966, *JACS*, 88, 5914-9; Kaiser et al., 1989, *Acc. Chem. Res.*, 22, 47-54; Nakatsuka et al., 1987, *JACS*, 109, 3808-10; Schnolzer et al., 1992, *Science*, 5054, 221-5; Chaiken et al., 1981, *CRC Crit. Rev. Biochem.*, 11, 255-301; Offord, 1987, *Protein Eng*, 1, 151-157; and Jackson et al., 1994, *Science*, 5183: 243-7; all of which are incorporated herein explicitly by reference.

The furan-peptides as taught herein can also be obtained by incorporating at least one furan amino acid into a peptide during protein translation in prokaryotes, such as bacteria, e.g. *E. coli*, or in eukaryotes such as yeast or mammalian cells, as described by Young and Schultz (2010, *J. Biol. Chem.*, 285(15), 11039-44).

In certain embodiments, the methods as described herein may comprise prior to step (a), the step of producing furan-peptides by incorporating at least one furan amino acid into a peptide during peptide translation in prokaryotes or in eukaryotes.

In certain embodiments, the methods as described herein may prior to step (a) comprise producing furan-peptides by a method comprising the steps of:
providing a translation system comprising: (i) a furan amino acid, (ii) an orthogonal tRNA synthetase, or a functional fragment or variant thereof, (iii) an orthogonal tRNA, wherein said orthogonal tRNA is specifically aminoacylated by said orthogonal tRNA synthetase with the furan amino acid, and (iv) a nucleic acid encoding a peptide, wherein the nucleic acid comprises a codon that is recognized by said orthogonal tRNA; and
translating the nucleic acid, thereby incorporating the furan amino acid into the peptide.

The genetic encoding of a furan amino acid in *Escherichia coli* and in human cells has been described by Schmidt et al. (Schmidt et al., 2013, *Angew. Chem. Int. Ed.*, 52, 4690-4693; 2013, *Angew. Chem.*, 125, 4788-4791; 2014, ChemBioChem., 15(12):1755-60).

The furan amino acid as taught herein can be any amino acid comprising a furan moiety, for example, the furan amino acid as taught herein may be selected from a furyl-glycine, furyl-alanine, furyl-valine, furyl-leucine, furyl-iso-leucine, furyl-proline, furyl-tyrosine, furyl-tryptophane, furyl-phenylalanine, furyl-cysteine, furyl-methionine, furyl-serine, furyl-threonine, furyl-lysine, furyl-arginine, furyl-histidine, furyl-aspartic acid, furyl-glutamic acid, furyl-asparagine or furyl-glutamine. In certain embodiments, the furan amino acid as taught herein may be furyl-alanine, furyl-glycine, or furyl-phenylalanine. Preferably, the furan amino acid as taught herein may be furylalanine, for example furyl-L-alanine or furyl-D-alanine, more preferably furyl-L-alanine. An important advantage of furyl-alanine is that it is commercially available. Moreover, furyl-alanine can be considered isosteric with histidine and iso-electronic with histidine and tyrosine. Consequently, no destabilization or alteration of the native protein structure is expected when incorporating furylalanine in a peptide. This allows that the furan-peptide may first perform its biological task and may only subsequently be labeled for intracellular tracking.

The furan amino acid as taught herein can be an Fmoc-protected or tBoc-protected furan amino acid which allows easy incorporation into peptides through solid-phase peptide synthesis. For example, Fmoc-protected furyl-alanine, which provides the required handle for subsequent orthogonal labeling, is a commercially available amino acid.

The furan amino acid as taught herein may further be a furan amino acid as described by Schmidt et al. (2014, ChemBioChem., 15(12), 1755-60).

The furan amino acid as taught herein may further be obtained through standard organic synthesis using commercially available furan derivatives and commercially available amino acid derivatives. Commercially available furan derivatives used in the methods as described herein comprise both 2- and 3-substituted furan derivatives. For instance, commercially available furan derivatives can be selected from, but are not limited to compounds with Formula (IIIa), (IIIb), (IIIc), (IIId), (IIIe), (IIIf) or (IIIg), (IIIh), (IIIi), (IIIj), (IIIk) or stereoisomeric forms thereof.

(IIIa)

(IIIb)

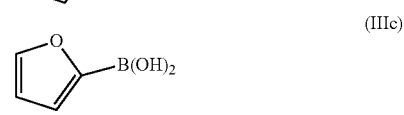

(IIIc)

(IIId)

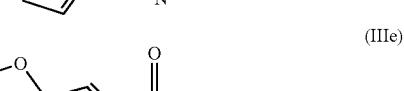

(IIIe)

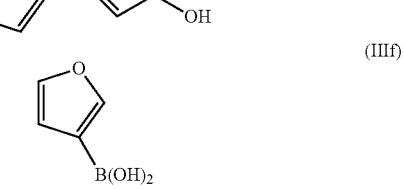

(IIIf)

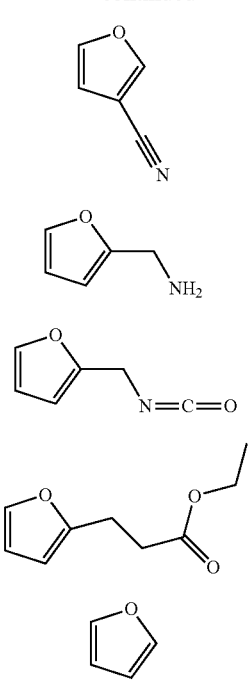

(IIIg)

(IIIh)

(IIIi)

(IIIj)

(IIIk)

Starting from commercially available furan derivatives, other furan derivatives are within reach through standard organic synthesis known to the skilled person.

Commercially available amino acid derivatives used in the methods as described herein can for example be selected from but are not limited to compounds with Formula (IVa) or (IVb), or stereoisomeric forms thereof,

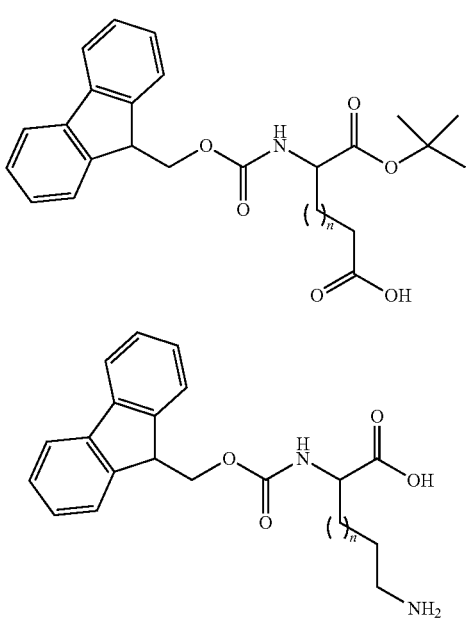

(IVa)

(IVb)

wherein n is an integer selected from 0, 1 or 2.

Figure 2:
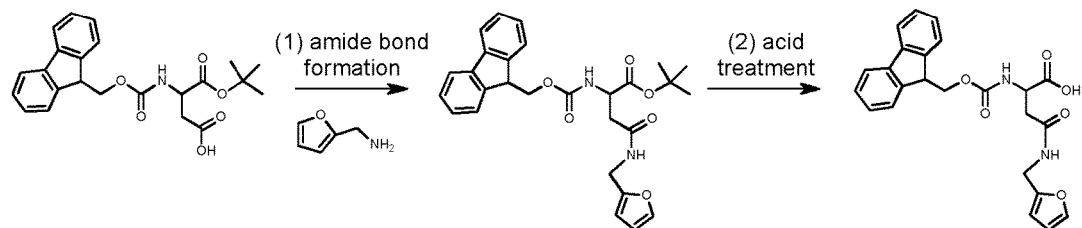
FIG. 2 represents a schematic overview illustrating the synthesis of a furan amino acid from a commercially available furyl amine derivative and an aspartic acid derivative. (1): amide bond formation; (2): acid treatment.
Figure 3A:
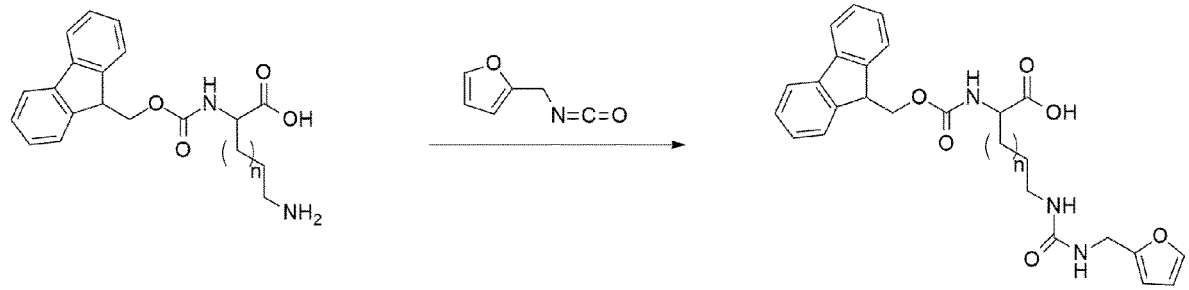
FIGS. 3A and 3B represent a schematic overview illustrating the synthesis of a furan amino acid from a lysine derivative and a commercially available furyl isocyanate derivative or a furyl carboxylic acid derivative respectively.
Figure 3B:
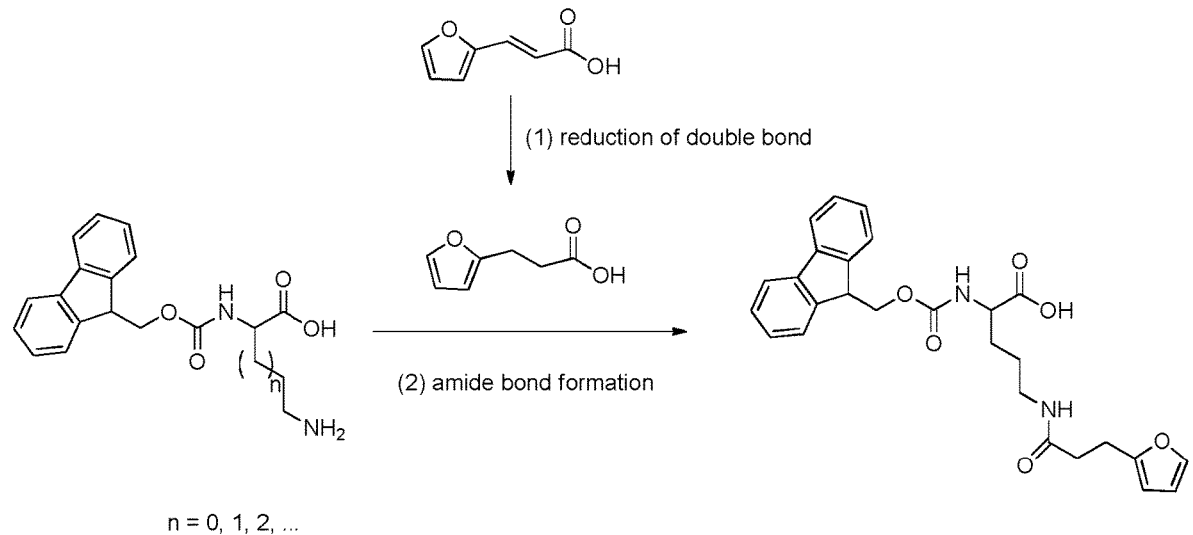

In an embodiment, the furan amino acids as taught herein are obtained through amide bond formation between a furyl amine derivative and the carboxyl group of a glutamic acid (Glu) derivative as depicted in FIG. 1. Furthermore, in an embodiment, the furan amino acids as taught herein may be obtained through amide bond formation between a furyl amine derivative and the carboxyl group of an aspartic acid (Asp) derivative as shown in FIG. 2. In an embodiment, the furan amino acids as taught herein may further be obtained through amide bond formation between a furyl isocyanate derivative or a furyl carboxylic acid derivative and the amine group of Lys as shown in FIGS. 3A and 3B, respectively.

In certain embodiments, the furan amino acid as taught herein can be located in any position in the peptide. It will be understood by the skilled person, however, that sterical hindrance, e.g. of the furan amino acid, by other amino acids of the peptide should preferably be avoided. The furan amino acid as taught herein should preferably be located in a position in the furan-peptide being accessible for coupling to a second agent, e.g., to a labeling agent, a small molecule, or a solid support. The position of the furan amino acid or furan moiety as taught herein in the peptide is preferably chosen based on, e.g., whether its position in a particular location would change the conformation, activity or stability of the peptide.

In an embodiment, the furan-peptides as taught herein contain at least three amino acids. Preferably, the furan-peptides as taught herein contain from 3 to 5000 amino acids, for example, the furan-peptides as taught herein contain from 3 to 20 amino acids, for example, the furan-peptides as taught herein contain 3, 4, 5, 6, 7, 8, 9, 10, 11, 12, 13, 14, 15, 16, 17, 18, 19, 20, 21, 22, 23, 24, or 25 amino acids. Preferably, the furan-peptides as taught herein contain from 20 to 50 amino acids, or from 50 to 100 amino acids, or from 100 to 1000, or from 1000 to 5000 amino acids; for example, the furan-peptides as taught herein contain 20, 25, 30, 35, 40, 45, 50, 60, 70, 80, 90, 100, 200, 300, 400, 500, 600, 700, 800, 900 or 1000 amino acids or any integer in between the aforementioned values.

In certain embodiments, the methods as described herein comprise the step of providing a composition comprising furan-peptides, said furan-peptides comprising at least one furan moiety, e.g., a furan amino acid.

The furan-peptides as taught herein may be free furan-peptides or furan-peptides bound to a solid support. In preferred embodiments, the furan-peptide as taught herein may be an unbound furan-peptide.

The terms "free", "deprotected", or "unbound" denote that the peptide is not coupled to a solid support, e.g. the furan-peptide is cleaved from the solid support on which it is synthesized or the furan-peptide is produced by protein translation. The free or unbound furan-peptides as taught herein include, but are not limited to, furan-peptides in solution and dried or lyophilized furan-peptides, such as, for instance a powder of furan-peptides.

The furan-peptides as taught herein may be provided in dried or lyophilized form, such as, for instance a powder of furan-peptides.

The furan-peptides as taught herein may be provided in solution. The furan-peptides as taught herein may be provided in a solvent wherein the furan-peptides can be dissolved. In certain embodiments, the solvent is water, dichloromethane (DCM), dimethylformamide (DMF), or N-methyl-2-pyrrolidone (NMP), dimethyl sulfoxide (DMSO), methanol, ethanol, chloroform ($CHCl_3$), acetonitrile ($CH_3CN$), or tetrahydrofuran (THF), or a combination of the aforementioned solvents. Preferably, the furan-peptides as taught herein are provided in a solvent comprising or consisting of water.

In certain preferred embodiments, the methods as described herein may comprise providing the furan-peptides in an aqueous solution.

The solid support for peptide synthesis is any support on which the furan-peptides as taught herein are synthesized. The solid supports for peptide synthesis may be polystyrene resins comprising an acid labile linker, a base-labile linker, or a photo-labile linker, or any other linker known in the art. The solid supports for peptide synthesis may also be polyethyleneglycol (PEG) resins comprising an acid labile linker, a base-labile linker, or a photo-labile linker, or any other linker known in the art. The solid supports for peptide synthesis may also be polystyrene-co-polyethyleneglycol resins comprising an acid labile linker, a base-labile linker, or a photo-labile linker, or any other linker known in the art. The solid supports for peptide synthesis are preferably chosen from polystyrene resins comprising an acid or base labile linker or polystyrene-co-polyethyleneglycol resins comprising an acid or base labile linker. In an embodiment, the solid support for peptide synthesis may be selected from the group comprising Wang resin, Rink amide resin, ChemMatrix®, phenylacetamidomethyl (PAM) resin, Merrifield resin, and paramethyl-benzhydrylamine (pMBHA) resin. It will be understood that furan-peptides which are subsequently, e.g. after synthesizing and cleaving from the solid support, coupled, connected or linked to a further solid support, such as for instance beads, membranes, colloids, rubber or synthetic particles and the like, can be considered free furan-peptides.

The furan-peptides as taught herein may be provided in a composition. In an embodiment, the composition preferably comprises or consists of at least 60%, preferably, at least 65%, 70%, 75%, 80%, 85%, 90%, 95%, 96%, 97%, 98%, 99% or 100% of furan-peptides. For example, the composition comprises from about 60% to about 70% of furan-peptides, for example, from about 70% to about 80% of furan-peptides, for example, from about 80% to about 90% of furan-peptides, for example, the composition comprises from about 90% to about 100% of furan-peptides. In an embodiment, the composition consists of 100% of substantially pure furan-peptides.

In certain preferred embodiments, the first agent may be a polymer.

In the context of the present invention, the term "furan-polymer" or "furan-modified polymer" refers to any polymer comprising a furan moiety.

The furan-polymers as taught herein comprise at least one furan moiety. The furan-polymers may comprise more than one, such as, for instance, 2, 3, 4, 5, 6, 7, 8, 9, 10, 11, 12, 13, 14, 15, 16, 17, 18, 19 or 20 furan moieties. In certain embodiments, the furan-polymer may comprise only one furan moiety. The furan moiety as taught herein can be located on any position in the furan-polymer.

The furan-polymers as taught herein can be obtained by any suitable method known by the person skilled in the art. In certain embodiments, a furan-polymer as taught herein may be obtained through standard organic synthesis using commercially available furan derivatives as described herein such as compounds of Formula (IIIa), (IIIb), (IIIc), (IIId), (IIIe), (IIIf) or (IIIg), (IIIh), (IIIi), (IIIj), (IIIk) or stereoisomeric forms thereof. In certain embodiments, a furan-polymer as taught herein may be obtained by reacting an amino group in a polymer with a commercially available furan derivative as described herein such as with a compound of Formula (IIIi).

In certain embodiments, the first agent may be a polymer such as a polynucleotide. In those embodiments, a furan-polymer as taught herein may be obtained by incorporating a furan-modified nucleoside-phosphoramidite building block in a polynucleotide. The furan-modified nucleoside-phosphoramidite building block may be incorporated at any position in the polynucleotide sequence. Furan-modified nucleoside-phosphoramidite building blocks are known by the person skilled in the art and have been described inter alia by Stevens and Madder, 2009, Nucleic acids research, 37, 5, 1555-1565; Op de Beeck and Madder, 2011, J. Am. Chem. Soc., 133, 796-807; Op de Beeck and Madder, 2012, J. Am. Chem. Soc., 134, 10737-10740; Jawalekar et al., 2011, Chem. Commun., 47, 2796-2798; Stevens et al., 2011, Chem. Eur. J., 17, 25, 6940-6953).

In certain embodiments, the first agent may be a small molecule.

In the context of the present invention, the phrase "furan-modified small molecule" refers to any small molecule comprising a furan moiety.

A furan-modified small molecule may be commercially available, e.g., ethyl 3-(furan-2-yl)propionate (Sigma Aldrich).

In certain embodiments, a furan moiety may be incorporated in a small molecule by methods known in the art. For instance, a furan moiety may be incorporated in a small molecule by reacting a small molecule with a commercially available furan derivative (e.g., compounds of Formula IIIa, IIIb, IIIc, IIId, IIIe, IIIf, IIIh, IIIg, IIIi, IIIj, or IIIk as defined herein) For instance, depending on the functional group availability, a commercially available furan derivative such as furan carboxylic acids or furfurylisocyanate can be incorporated into a small molecule by methods known in the art such as esterification, amide bond formation, aryl-aryl coupling, or urea bond formation.

In an embodiment, the methods as taught herein comprise (the step of) b) contacting the first agent with an activation signal, thereby activating said furan moiety to an activated furan moiety.

The recitations "contacting a first agent with an activation signal" refers to exposing a first agent to an activation signal. Exposing a first agent to an activation signal may be performed actively (e.g., by bringing together the first agent and the activation signal such as singlet oxygen) or may be performed passively (e.g., in case the first agent encounters an activation signal such as reactive oxygen species).

In certain embodiments, the activation signal may activate the furan moiety of a first agent to an intermediate comprising a hydroxy-hydroperoxy moiety and/or an intermediate comprising a keto-enal moiety or a (2,5-dihydroxy-2H-furan-5-yl)-moiety.

The terms "activate" or "oxidize" relate to the oxidation of a furan moiety to a hydroxy-hydroperoxy moiety; and/or a keto-enal moiety or a (2,5-dihydroxy-2H-furan-5-yl)-moiety. The hydroxy-hydroperoxy moiety, keto-enal moiety or (2,5-dihydroxy-2H-furan-5-yl)-moiety allow the formation of a covalent bond between the first agent and the hydrazine or hydroxylamine moiety of the second agent.

The term "activated furan moiety" as used herein refers to a furan moiety which is oxidized to a hydroxy-hydroperoxy moiety; and/or a keto-enal moiety or a (2,5-dihydroxy-2H-furan-5-yl)-moiety. The activated furan moiety advantageously is stable and can be characterized if needed before reaction with a second agent.

In certain embodiments, when the first agent is a peptide, the activation signal as defined herein may activate the furan moiety of a furan-peptide to an intermediate comprising a hydroxy-hydroperoxy moiety and an intermediate comprising a keto-enal moiety or a (2,5-dihydroxy-2H-furan-5-yl)-moiety.

The term "activated furan-peptide" as used herein refers to a peptide wherein the furan moiety is oxidized to a hydroxy-hydroperoxy moiety; and/or a keto-enal moiety or a (2,5-dihydroxy-2H-furan-5-yl)-moiety. The activated furan-peptides advantageously are stable and can be characterized if needed before reaction with a second agent such as a labeling agent, a small molecule, a solid support, a biomolecule, or a polymer.

Figure 4:
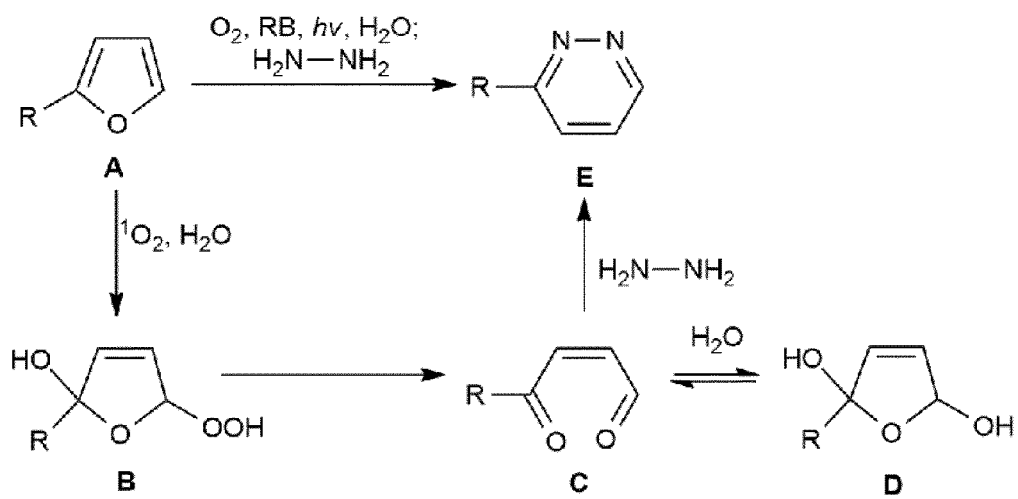
FIG. 4 represents a schematic overview illustrating a possible mechanism for the activation of furan-peptides to activated furan-peptides comprising an activated furan moiety using singlet oxygen as activation signal. A: furan-peptide; B: peptide comprising a hydroxy-hydroperoxy moiety; C: peptide comprising a keto-enal moiety; D: peptide comprising a (2,5-dihydroxy-2H-furan-5-yl)-moiety; and E: peptide comprising a pyridazine moiety.

A mechanism for the activation of a furan moiety of Formula (IIa) using singlet oxygen as activation signal is shown in FIG. 4. The oxidation of the furan moiety in a furan-peptide (FIG. 4, compound A) with singlet oxygen as activation signal is performed through a [4+2] cycloaddition, wherein furan functions as diene and wherein a 2,5-endoperoxide is formed. In an aqueous solution, further intermediates which are formed include intermediates comprising a hydroxy-hydroperoxy moiety (FIG. 4, intermediate B), and intermediates comprising a keto-enal moiety (FIG. 4, intermediate C) or comprising a (2,5-dihydroxy-2H-furan-5-yl)-moiety (intermediate D). Finally, reaction with hydrazine ($NH_2$—$NH_2$) results in the formation of a peptide comprising a pyridazine-moiety (FIG. 4, compound E).

In certain embodiments, the activation signal may be singlet oxygen. In certain embodiments, the activation signal may be singlet oxygen generated by photosensitization.

In certain embodiments, the singlet oxygen may be generated by irradiation of air or oxygen in the presence of a sensitizer. Singlet oxygen is preferably generated by irradiation in combination with sensitizers. In this case, the sensitizer needs to be excited by irradiation such as visible light and relaxes by converting triple oxygen to singlet oxygen. Singlet oxygen as activation signal has the advantage that, if controlled, it can be a nondestructive activation signal.

In certain embodiments, photosensitization may be performed using polychromatic (visible) light (such as Euromex tunable Cold light source with Halogen lamp 100 W), Xenon light (such as 300 W Xenon lamp, e.g., a Xenon Variac Eimac Cermax 300 W lamp), or monochromatic light such as monochromatic light with filters (e.g. red light).

In certain embodiments, the solution comprising the first agent (e.g., furan-peptide) is well-aligned to the lamp.

Preferably, the distance between the vessel (e.g., tube) comprising the first agent (e.g., furan-peptide) and the lamp is minimum. For example, the distance between the vessel comprising the first agent (e.g., furan-peptide) and the lamp is 0 mm to 20 mm, such as 1 mm to 10 mm.

Preferably, the distance between the vessel (e.g., tube) comprising the first agent (e.g., furan-peptide) and the lamp is the minimum and the solution comprising the first agent (e.g., furan-peptide) is well-aligned to the lamp for fast and efficient oxidation.

In certain embodiments, air or oxygen may be bubbled through a solution comprising the first agent (e.g., furan-peptide).

In certain embodiments, the irradiation may be polychromatic (or visible) light, Xenon light, or monochromatic light. In certain embodiments, the irradiation may be visible light such as red light, green light, blue light, or unfiltered white light, depending on the photosensitizer.

In certain embodiments, the sensitizer may be selected from the group consisting of xanthene, xanthene derivatives, fluorescein, fluorescein derivatives, methylene blue, porphyrine, porphyrine derivatives, phtalocyanine, phtalocyanine derivatives, naphthalocyanines, bacteriochlorins, texaphyrins, cholorophyll, and spirulina.

In certain embodiments, the sensitizer may be selected from the group consisting of Rose bengal (4,5,6,7-tetrachloro-2',4',5',7'-tetraiodo-fluorescein), methylene blue, porphyrine, porphyrine derivatives, phtalocyanine, phtalocyanine derivatives, naphthalocyanines, bacteriochlorins, texaphyrins, chlorophyll, and spirulina.

In certain embodiments, said singlet oxygen may be generated by irradiation, of air or oxygen by polychromatic light in the presence of Rose bengal. In certain embodiments, said singlet oxygen may be generated by irradiation of air or oxygen by polychromatic light in the presence of Rose bengal, wherein the concentration of the Rose bengal is 1 µM to 400 µM. For instance, the singlet oxygen may be generated by irradiation of air or oxygen by polychromatic light in the presence of Rose bengal, wherein the concentration of the Rose bengal is 2 µM to 400 µM, 5 µM to 400 µM, 5 µM to 300 µM, 5 µM to 200 µM, 1 µM to 100 µM, or 5 µM to 100 µM. Preferably, the singlet oxygen may be generated by irradiation of air or oxygen by polychromatic light in the presence of Rose bengal, wherein the concentration of the Rose bengal is about 10 µM.

In certain embodiments, the singlet oxygen may be generated by irradiation, preferably for 2 min to 60 min, of air or oxygen in the presence of Rose bengal with an Euromex 100 W cold light Halogen microscope lamp, wherein the concentration of the Rose bengal is 5 µM to 100 µM, preferably about 10 µM.

The singlet oxygen quantum yield ($\Phi^1O_2$) of Rose bengal, irradiated by polychromatic light, in aqueous solutions, is well known in the literature (Gandin et al., Photochem. Photobiol., 1983, 37, 271-278; Redmond and Gamlin, Photochem. Photobiol., 1999, 70, 391-475; Coordination Chemistry Reviews, 2002, 233-234, 351-371).

In certain embodiments, said activation signal is singlet oxygen in an amount as generated by irradiation, preferably for 2 min to 60 min, of air or oxygen in the presence of Rose bengal with an Euromex 100 W cold light Halogen microscope lamp, wherein the concentration of the Rose bengal is 5 µM to 100 µM, preferably about 10 µM.

In certain embodiments, the second agent may be capable of acting as a sensitizer.

Hence, in certain embodiments, singlet oxygen may be generated by irradiation of air or oxygen by polychromatic light in the presence of a second agent capable of acting as a sensitizer. For instance, a second agent capable of acting as a sensitizer may be lucifer yellow CH (LYCH), an acridine dye, or fluorescein.

In certain embodiments, when the methods comprise the steps of: a) providing a first agent comprising at least one furan moiety; b') contacting the first agent with a second agent comprising at least one hydrazine moiety or at least one hydroxylamine moiety; c') contacting the first agent with an activation signal, thereby activating said furan moiety to an activated furan moiety; and d) reacting the activated furan moiety with the hydrazine moiety or the hydroxylamine moiety, thereby site-selectively coupling the first agent to the second agent, the activation signal may consist essentially of or may consist of irradiation of air or oxygen by polychromatic light.

Singlet oxygen is further advantageous if coupling of a first agent to a second agent is desired in humans and/or animals. The in vivo use of furan may seem counterintuitive in view of its carcinogenic properties. However, since the oxidation of furan is inducible, the formation of a reactive moiety and the consequent coupling to a second agent are only triggered in the presence of an activation signal. Singlet oxygen can be specifically generated in various biological tissues by use of a sensitizer, as is demonstrated in photodynamic therapy for the treatment of tumors. In vivo activation of furan is possible because the sensitizer can be selectively absorbed by the affected cells, where it is irradiated with long wavelength light which penetrates deep into the tissue. Thereby, large amounts of reactive singlet oxygen are generated, leading to activation of the furan moiety.

Alternatively, furan activation by singlet oxygen can occur even without the combination with sensitizer and irradiation. All cells produce singlet oxygen to some extent and cancerous or infected cells produce singlet oxygen to a higher extent. The present inventors have shown that the furan moiety can be activated in or on cells without specific activation and that reactive oxygen species (ROS) may be involved. Accordingly, in certain embodiments, the activation signal may be a reactive oxygen species which is generated by cells. In certain embodiments, the activation signal may be a reactive oxygen species which is generated intracellulary or extracellularly.

In an embodiment, the methods as described herein further comprise (the step of) c) contacting said activated furan moiety with a second agent comprising at least one hydrazine moiety or at least one hydroxylamine moiety. In other words, in an embodiment, the methods as described herein comprise exposing said activated furan moiety to a second agent comprising a hydrazine moiety or hydroxylamine moiety. Preferably, the second agent comprises a hydrazine moiety, more preferably a hydrazide moiety.

The recitations "contacting the activated furan moiety with a second agent" or "exposing the activated furan moiety to a second agent" refers to bringing together the activated furan moiety and a second agent.

In certain embodiments, the second agent may be a labeling reagent, a small molecule, a solid surface, a biomolecule, or a polymer.

In certain embodiments, the second agent as taught herein may be a labeling agent. In certain embodiments, the labeling agent may be a fluorophore or a non-fluorescent label.

The term "fluorophore, "fluorescent agent", or "fluorescent probe" generally refers to a fluorescent chemical compound that can re-emit light upon light excitation. Fluorophores typically contain several combined aromatic groups, or planar or cyclic molecules with several π bonds. A fluorophore may advantageously serve as a marker (or dye, or tag, or reporter) for the first agent to which it is coupled. The fluorophore may allow to detect a peptide in a tissue, in a cell, or other material in a variety of analytical methods, i.e., fluorescent imaging and spectroscopy.

In certain embodiments, the fluorophore may comprise a fluorescein moiety, a rhodamine moiety, a coumarin moiety, or a cyanine moiety.

Suitable non-limiting examples of labeling agents, in particular fluorophores, include Lucifer Yellow CH dilithium salt, fluorescein-5-thiosemicarbazide, rhodamine hydrazide, pyrene hydrazide, and Alexa Fluor® 488 hydrazide, and biotin hydrazide.

In certain embodiments the labeling agent may be a non-fluorescent label such as a biotin hydrazide or a biotin semicarbazide. Such a non-fluorescent label such as a biotin hydrazide or biotin semicarbazide may allow conjugation and purification of the first agent.

In certain embodiments, the second agent may be a fluorophore comprising a hydrazine moiety or hydroxylamine moiety.

In the methods as taught herein, the hydrazine or hydroxylamine moiety may be part of the fluorophore (e.g., may be naturally present in the fluorophore or may be part of a commercially available fluorophore).

Suitable, non-limiting examples of second agents comprising a hydrazine moiety, in particular fluorophores comprising a hydrazide moiety, include Alexa Fluor® 350 Hydrazide, Alexa Fluor® 488 Hydrazide, Alexa Fluor® 514 Hydrazide, Alexa Fluor® 532 Hydrazide, Alexa Fluor® 568 Hydrazide, Alexa Fluor® 594 Hydrazide, Alexa Fluor® 555 Hydrazide, Alexa Fluor® 633 Hydrazide, and Alexa Fluor® 647 Hydrazide (all Life Technologies, CA, USA); rhodamine hydrazide (Product Number 83684, Sigma-Aldrich, Mo., USA); and pyrene hydrazide or 1-pyrenebutyric hydrazide (Product Number 82669, Sigma-Aldrich, Mo., USA).

Suitable, non-limiting examples of second agents comprising a hydrazine moiety, in particular fluorophores comprising a carbohydrazide moiety, include Lucifer Yellow CH dilithium salt (Product Number L 0259, Sigma-Aldrich, Mo., USA).

Suitable, non-limiting examples of second agents comprising a hydrazine moiety, in particular fluorophores comprising a thiosemicarbazide moiety, include fluorescein-5-thiosemicarbazide (Product Number 46985, Sigma-Aldrich, Mo., USA).

In the methods as taught herein, the hydrazine or hydroxylamine moiety may be introduced into the fluorophore by a chemical reaction.

In certain embodiments, the hydrazine or hydroxylamine moiety may be inserted in a fluorophore (e.g., commercially available fluorophore) by a chemical reaction. In certain embodiments, a second agent comprising a hydrazine moiety may be synthesized or prepared by reacting a fluorophore (e.g., commercially available fluorophore) comprising an N-hydroxysuccinimide (NHS) ester with tert-butyl carbazate followed by treatment with trifluoroacetic acid (TFA). For example, a fluorescein-semicarbazide may be prepared by reaction of a NHS-fluorescein with tert-butyl carbazate in the followed by treatment with TFA.

For example, fluorophores configured for the preparation of fluorophores comprising a hydrazine moiety include Alexa Fluor® 350 NHS ester, Alexa Fluor® 488 NHS ester, Alexa Fluor® 514 NHS ester, Alexa Fluor® 532 NHS ester, Alexa Fluor® 568 NHS ester, Alexa Fluor® 594 NHS ester, Alexa Fluor® 555 NHS ester, Alexa Fluor® 633 NHS ester, and Alexa Fluor® 647 NHS ester (all Life Technologies, CA, USA) and 5(6)-Carboxyfluorescein N-hydroxysuccinimide ester (Product Number 21878-25MG-F, Sigma-Aldrich, Mo., USA).

Suitable non-limiting examples of non-fluorescent labels comprising a hydrazine moiety include biotin hydrazide ((+)-Biotin hydrazide, B7639, Sigma-Aldrich, Mo., USA).

In certain embodiments, the second agent as taught herein may be a small molecule comprising a hydrazine moiety. In certain embodiments, the second agent as taught herein may be a drug comprising a hydrazine moiety.

In certain embodiments, the first agent may be a peptide comprising at least one furan moiety and the second agent may be a labeling agent comprising one hydrazine moiety or at least one hydroxylamine moiety. The methods of the present invention thus advantageously allow preparing labeled peptides.

In certain embodiments, the first agent may be an oligonucleotide comprising at least one furan moiety and the second agent may be a labeling agent comprising one hydrazine moiety or at least one hydroxylamine moiety. The methods of the present invention thus advantageously allow preparing labeled oligonucleotides.

In certain embodiments, the second agent as taught herein may be a small molecule. In certain embodiments, the small molecule may be a drug, a pesticide, or a cell signaling molecule.

In certain embodiments of the methods as taught herein, the first agent may be an antibody and the small molecule may be a drug. Such methods advantageously allow the preparation of antibody-drug conjugates whereby the drug is site-specifically coupled to the antibody.

In certain embodiments, the small molecule may be a natural small molecule such as a secondary metabolite. In certain embodiments, the small molecule may be a synthetic or artificial small molecule such as an antiviral drug.

Suitable non-limiting examples of small molecules comprising a hydrazine moiety include isonicotinylhydrazine or isonicotinic hydrazide (Isoniazid, marketed under brand names including Hydra, Isovit, Laniazid, and Nydrazid); aminoguanidine (Pimagedine), N4-(N,N-diphenylcarbamoyl)-aminoguanidine (DrugBank Accession Number: DB07120); Aza peptides (e.g. goserelin); and semicarbazide-sensitive amine oxidase (SSAO) inhibitors.

In certain embodiments, the second agent as taught herein may be a solid support.

The terms "solid support" or "solid surface" may be used interchangeably herein.

In certain embodiments, the solid support may be substantially made of a solid support material. In certain embodiments, the solid support material may be any suitable material onto which a first agent (e.g., a peptide) can be immobilized. In certain embodiments, the solid support may be substantially made of a chemically-activated material onto which a first agent (e.g., a peptide) can be immobilized. In certain embodiments, the solid support material may be any suitable rigid material onto which a first agent (e.g., a peptide) can be immobilized.

In certain embodiments, the solid support material may a polymeric material or glass. In certain embodiments, the solid support material may be substantially plastic, such as for example polystyrene, polypropylene, polycarbonate, polyethylene glycol (PEG), poly(2-oxazoline), or copolymers thereof.

In certain embodiments, the solid support may be substantially made of a chemically-activated material comprising a hydrazine moiety. For instance, a solid support comprising a hydrazine moiety has been described by Melnyk et al. (2002, Bioconjugate Chem., 13, 713-720).

In certain embodiments, the second agent as taught herein may be a biomolecule. In certain embodiments, the biomolecule may be a peptide, a polysaccharide, a lipid, a nucleic acid, or a combination thereof.

In certain embodiments, the second agent may be a peptide. In certain embodiments, the first agent may be a peptide comprising at least one furan moiety and the second agent may be a peptide comprising at least one hydrazine moiety or at least one hydroxylamine moiety. The method of the present invention can thus advantageously be used for coupling two or more peptides to each other, for instance for the preparation of alphabodies or for peptide stitching. In certain embodiments, the first agent may be a peptide comprising two or more furan moieties, such as two, three, four, five, six, seven, eight, nine, or ten furan moieties, and the second agent may be a peptide comprising two or more hydrazine or hydroxylamine moieties, such as two, three, four, five, six, seven, eight, nine, or ten hydrazine or hydroxylamine moieties. Alternatively, in certain embodiments, the first agent may be a peptide comprising a combination of at least one furan moiety (e.g., two or more furan moieties, such as two, three, four, five, six, seven, eight, nine, or ten furan moieties) and two or more hydrazine or hydroxylamine moieties, such as two, three, four, five, six, seven, eight, nine, or ten hydrazine or hydroxylamine moieties, and the second agent may be a peptide comprising a combination of at least one hydrazine or hydroxylamine moiety (e.g., two or more hydrazine or hydroxylamine moieties, such as two, three, four, five, six, seven, eight, nine, or ten hydrazine or hydroxylamine moieties) and two or more furan moieties, such as two, three, four, five, six, seven, eight, nine, or ten furan moieties. In certain embodiments, the first agent and the second agent may be the same peptide or a different peptide.

In certain embodiments, the first agent may be an oligonucleotide comprising at least one furan moiety and the second agent may be a peptide comprising at least one hydrazine moiety or at least one hydroxylamine moiety. The methods of the present invention therefore allow preparing oligonucleotide-peptide conjugates.

In certain embodiments, the at least one furan moiety and the at least one hydrazine moiety or at least one hydroxylamine moiety may be part of or may be located on one agent (e.g., one agent acting at the same time as first agent and second agent) such as one peptide. The method of the present invention may thus allow generating cyclic conjugates, such as cyclic peptides.

In certain embodiments, a hydrazine moiety or hydroxylamine moiety may be incorporated in a peptide or protein via modification of the N-terminus of the peptide or protein or via a lysine side chain (provided an orthogonal protecting group is used). For instance, a peptide may be reacted with Tri-Boc-hydrazinoacetic acid or (Boc-aminooxy)acetic acid to introduce a hydrazide moiety on a free amino group.

Alternatively, in certain embodiments, a free N-terminus of a peptide or protein may be reacted with bis(2,2,2-trifluoroethyl)carbonate or 2,2,2-trifluoroethylchloroformate followed by treatment with a hydrazine hydrate delivering a substituted carbazide (see Bogolubsky et al., 2015, RSC Adv., 5, 1063-1069, Schemes 2 and 3, and Table 1).

In certain embodiments, a C-terminal hydrazide moiety may be incorporated in a peptide or protein by starting the synthesis on a Cl-Trt resin, treating it with hydrazine, and subsequently synthesizing the peptide of desired sequence. Final TFA cleavage yields C-terminally modified peptide hydrazides (see Zheng et al., 2013, Nature Protocols, 8, 12, 2483-2495, inter alia FIG. 1).

The skilled person will understand that the method of the present invention also allows the coupling of one or more further agents, such as a third agent, as long as each further agent comprises at least one furan moiety or at least one hydrazine or hydroxylamine moiety. The further agent may be the same or different from the first agent and/or second agent. For instance, the method of the present invention may allow the coupling of a further peptide such as a third peptide. In certain embodiments, the further peptide may be the same or different from the first peptide and/or second peptide.

In certain embodiments, the second agent as taught herein may be a polymer as defined herein.

In certain embodiments, the second agent may be a synthetic polymer such as polyester (PES), polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS) high impact polystyrene (HIPS), polyamides (PA) (Nylons), acrylonitrile butadiene styrene (ABS), polyethylene/acrylonitrile butadiene styrene (PE/ABS), polycarbonate (PC), polycarbonate/acrylonitrile butadiene styrene (PC/ABS), and polyurethanes (PU).

In certain embodiments, the second agent may be a natural polymer (i.e., biopolymer) such as a polynucleotide (i.e., RNA and DNA); a polypeptide; or a polysaccharide.

A suitable non-limiting example of a polymer comprising a hydrazine moiety includes a hydrazide-modified polymer like PEG.

In certain embodiments, the first agent may be contacted with the second agent in a molar ratio (mole/mole) of from 1:1 to 1:100. In certain embodiments, the first agent may be contacted with the second agent in a molar ratio (mole/mole) from 1:1 to 1:50, from 1:1 to 1:25, from 1:1 to 1:20, from 1:1 to 1:10, or from 1:1 to 1:5.

In certain embodiments, the first agent may be contacted with the second agent in an equivalent ratio of from 1:1 to 1:100. In certain embodiments, the first agent may be contacted with the second agent in an equivalent ratio from 1:1 to 1:50, from 1:1 to 1:25, from 1:1 to 1:20, from 1:1 to 1:10, or from 1:1 to 1:5.

In the methods of the present invention, the order of the steps b) and c) may be reversed. Hence, in certain embodiments, the present invention provides a method for site-selective coupling of a first agent to a second agent, comprising the steps of: a) providing a first agent comprising at least one furan moiety; b') contacting the first agent with a second agent comprising at least one hydrazine moiety or at least one hydroxylamine moiety; b or c') contacting the first agent with an activation signal, thereby activating said furan moiety to an activated furan moiety; and d) reacting the activated furan moiety with the hydrazine moiety or the hydroxylamine moiety, thereby site-selectively coupling the first agent to the second agent.

In certain embodiments, in case the first agent is contacted with the activation signal after contacting the first agent with the second agent, the activation of said furan moiety to an activated furan moiety and the reaction of the activated furan moiety with the hydrazine moiety or the hydroxylamine moiety may proceed without any further intervention, e.g. without any further human intervention. Hence, in these embodiments, the site-selective coupling of a first agent to a second agent can be said to be performed "in one pot" or "all-in-one".

In certain embodiments of the methods as taught herein, the first agent may be contacted with the activation signal immediately after contacting the first agent with the second agent, e.g., the first agent may be contacted with the activation signal at most 10 minutes after contacting the first agent with the second agent. For instance, the first agent may be contacted with the activation signal at most 5 minutes, or at most 3 minutes, or at most 1 minute, or at most 30 seconds, or at most 10 seconds, or at most 5 seconds after contacting the first agent with the second agent.

In certain embodiments, the present invention provides a method for site-selective coupling of a peptide to a second agent, comprising the steps of: a) providing a furan-peptide, said furan-peptide comprising at least one furan moiety; b') contacting the furan-peptide with a second agent comprising at least one hydrazine moiety or at least one hydroxylamine moiety; b or c') contacting the furan-peptide with an activation signal, thereby activating said furan-peptide to an activated furan-peptide; and d) reacting the activated furan-peptide with the hydrazine moiety or the hydroxylamine moiety, thereby site-selectively coupling the activated furan-peptide to the second agent.

In preferred embodiments, the step of contacting the first agent with a second agent comprising a hydrazine or hydroxylamine moiety occurs after activation of the furan moiety. This allows to use less equivalents of the second agent while still obtaining high reaction yields, which is advantageous for expensive or sensitive agents such as labeling agents.

In an embodiment, the methods as described herein comprise (the step of) d) reacting said activated furan moiety with the hydrazine moiety or the hydroxylamine moiety, thereby site-selectively coupling said first agent to said second agent.

In an embodiment, the activated furan moiety as taught herein reacts with the hydrazine moiety of the second agent. Preferably, coupling of a first agent to a second agent occurs between the activated furan moiety of the first agent as taught herein and the hydrazine moiety of the second agent as taught herein.

In an embodiment, the activated furan moiety as taught herein reacts with the hydroxylamine moiety of the second agent. Preferably, coupling of a first agent to a second agent occurs between the activated furan moiety of the first agent as taught herein and the hydroxylamine moiety of the second agent as taught herein.

Figure 8:
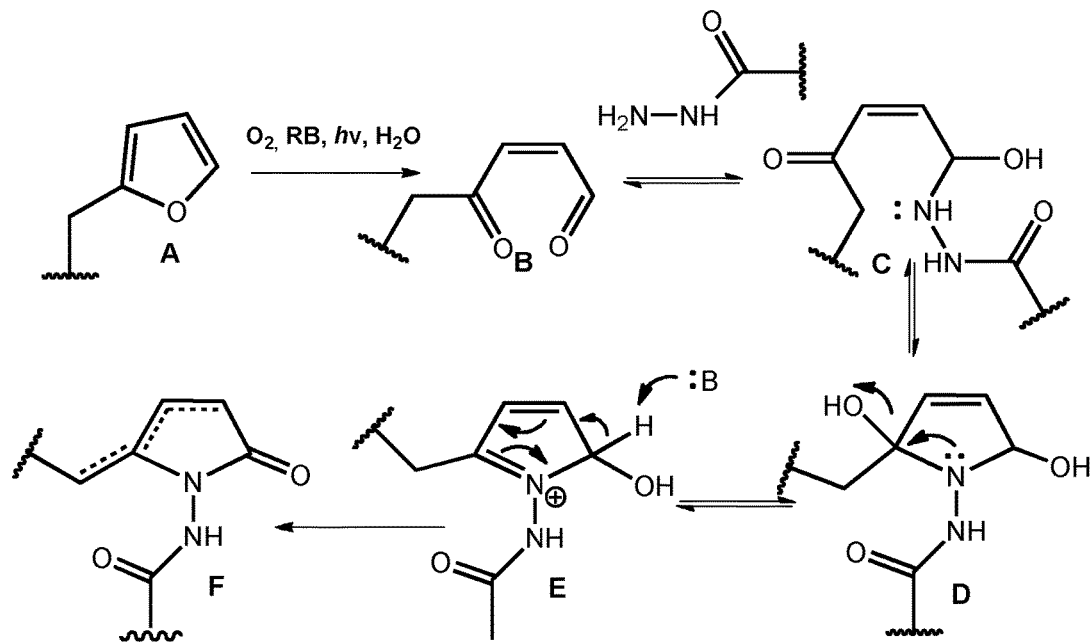
FIG. 8 represents a schematic overview illustrating the proposed mechanism for the oxidation of a furan-peptide and the reaction of an activated furan-peptide with a second agent comprising a hydrazide moiety.
Figure 32:
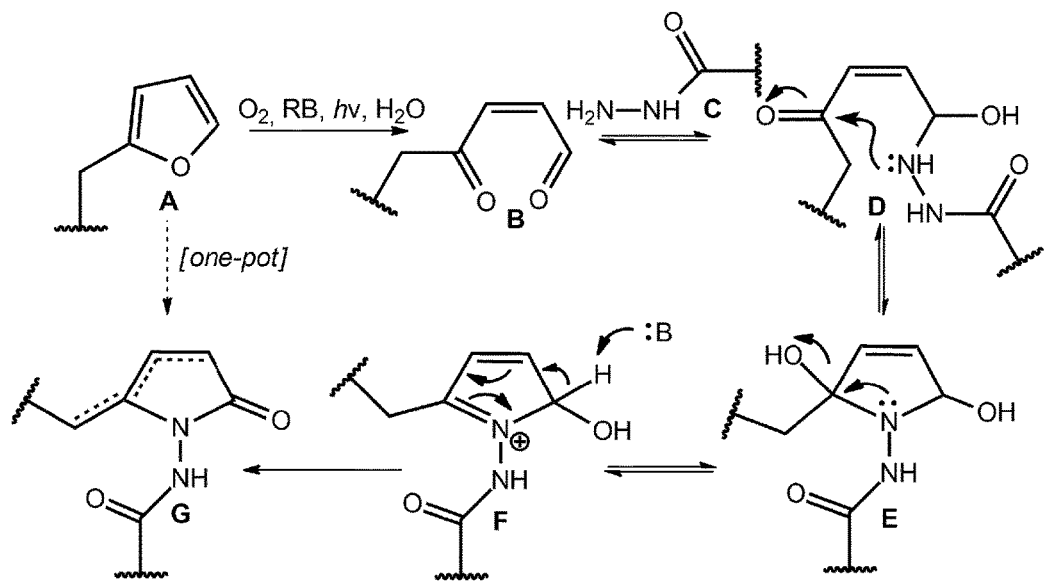
FIG. 32 represents a schematic overview illustrating a proposed mechanism for the oxidation of a furan-peptide and the reaction of an activated furan-peptide with a second agent comprising a hydrazide moiety.

In certain embodiments, the coupling of a peptide to a second agent occurs between the activated furan moiety of the activated furan-peptide as taught herein and the hydrazine or hydroxylamine moiety of the second agent as taught herein. In certain embodiments, a conjugate (FIG. 8, compound F) may be obtained after reaction of an activated furan-peptide of Formula B (FIG. 8) with a second agent (FIG. 8). In certain embodiments, a conjugate of Formula F (FIG. 8) may be obtained after reaction of the activated furan moiety of an activated furan-peptide of Formula B (FIG. 8) with the hydrazine moiety of a second agent, in particular the hydrazide moiety of the second agent (FIG. 8). In certain embodiments, a conjugate (FIG. 32, compound G) may be obtained after reaction of an activated furan-peptide of Formula B (FIG. 32) with a second agent of Formula C (FIG. 32). In certain embodiments, a conjugate of Formula F (FIG. 32) may be obtained after reaction of the activated furan moiety of an activated furan-peptide of Formula B (FIG. 32) with the hydrazine moiety of a second agent, in particular the hydrazide moiety of the second agent of Formula C (FIG. 32). The coupling may be performed in one pot (all-in-one), as explained herein.

In certain embodiments, the methods for site-selective coupling of a peptide to a second agent may comprise the steps of: a) providing a furan-peptide, said furan-peptide comprising at least one furan moiety; b) contacting the furan-peptide with an activation signal, thereby activating said furan-peptide to an activated furan-peptide comprising an activated furan moiety; c) contacting said activated furan-peptide comprising an activated furan moiety with a second agent comprising at least one hydrazine moiety; and d) reacting the activated furan moiety of the activated furan-peptide with the hydrazine moiety, thereby site-selectively coupling the activated furan moiety of the activated furan-peptide to the hydrazine moiety of the second agent.

In certain embodiments, the methods for site-selective coupling of a peptide to a second agent, may comprise the steps of: a) providing a furan-peptide, said furan-peptide comprising at least one furan moiety; b) contacting the furan-peptide with an activation signal, thereby activating said furan-peptide to an activated furan-peptide comprising an activated furan moiety; c) contacting said activated furan-peptide comprising an activated furan moiety with a second agent comprising at least one hydroxylamine moiety; and d) reacting the activated furan moiety of the activated furan-peptide with the hydroxylamine moiety, thereby site-selectively coupling the activated furan moiety of the activated furan-peptide to the hydroxylamine moiety of the second agent.

In the context of the present invention, the methods as taught herein are performed in solution. The methods as taught herein may be performed in a solvent in which the first agent and/or second agent can be dissolved. In certain embodiments, the solvent may comprise, consist essentially of, or consist of water, DCM, DMF, NMP, DMSO, methanol, ethanol, chloroform, acetonitrile, THF, or a combination of the aforementioned solvents. Preferably, the methods as taught herein are performed in a solvent comprising or consisting of water.

The methods as described herein may be performed in an aqueous solution.

The term "aqueous solution" generally refers to a solution in which the solvent comprises, consists essentially of, or consists of water. In certain embodiments, the aqueous solution comprises at least 0.1% of water. For example, the aqueous solution comprises at least 0.5%, at least 1%, at least 5%, at least 10%, at least 20%, at least 30%, at least 40%, at least 50%, at least 60%, at least 70%, at least 80%, at least 90%, at least 95%, or at least 99% of water. In certain embodiments, the solvent consists of water.

The methods as described herein may be performed in an organic solvent such as DCM, DMF, NMP, DMSO, methanol, ethanol, chloroform, acetonitrile, or THF.

In certain embodiments of the methods as taught herein, the first agent as taught herein may be provided in an aqueous solution. In certain embodiments, the second agent as taught herein may be provided in an aqeuous solution.

In certain embodiments of the methods as taught herein, the first agent as taught herein may be provided in an organic solvent. In certain embodiments, the second agent as taught herein may be provided in an organic solvent.

In certain preferred embodiments, the methods as taught herein may be performed in an aqueous solution. For instance, when the first agent is a peptide, the method is preferably performed in an aqueous solution.

In certain embodiments, the methods as taught herein may be performed in vivo or intracellularyl. In certain embodiments, for instance when the methods as taught herein are performed in vivo or intracellulary, the methods as taught herein may be performed in intracellular fluid (i.e., cytosol or liquid found inside cells). In certain embodiments, the methods as taught herein may be performed in extracellular fluid (i.e., fluid found outside cells) such as interstitial fluid (or tissue fluid) or blood plasma. In these instances, the methods as taught herein can be performed in an aqueous solution without the addition of water.

In certain embodiments, the methods as described herein may be performed in an aqueous solution without the use of organic solvents. In certain embodiments, the methods as described herein may be performed in an aqueous solution without the use of reducing agents. In certain embodiments, the methods as described herein may be performed without the use of toxic additives (e.g., copper or aniline) and/or without the use of catalysts (e.g., copper or aniline). In certain embodiments, the methods as described herein may be performed in an aqueous solution without the use of organic solvents and/or without the use of reducing agents and/or without the use of toxic additives and/or without the use of catalysts. Such conditions advantageously offer great potential for in cellulo applications of the methods as described herein. Furthermore, the first agent-second agents conjugates prepared in an aqueous solution are stable.

In certain embodiments, the methods as described herein may be performed at physiological conditions. Advantageously, such conditions allow the application of the methods as described herein in an intracellular context and in vivo.

In certain embodiments, the methods as described herein may be performed at a pH ranging from about 3 to about 11. In certain embodiments, the methods as described herein may be performed at a pH ranging from about 3 to about 10. In certain embodiments, the methods as described herein may be performed at a pH ranging from about 3 to about 9. In certain embodiments, the methods as described herein may be performed at a pH ranging from about 4 to about 8. In certain embodiments, the methods as described herein may be performed at a near neutral pH.

In certain embodiments, the methods as described herein may be performed at physiological conditions and at a pH ranging from about 3 to about 11. In certain embodiments, the methods as described herein may be performed at physiological conditions and at a pH ranging from about 4 to about 8.

In certain embodiments, the methods as described herein may be performed in an aqueous solution, at physiological conditions, and at near neutral pH. Such conditions allow the application of the methods as described herein in an intracellular context and in vivo.

In embodiments, the methods as taught herein may further comprise the step of identifying the first agent-second agent conjugate. In certain embodiments, the methods as taught herein may further comprise the step of identifying the covalent bond between the first agent and the second agent, i.e., identifying the covalent bond between the activated furan moiety and the hydrazine or hydroxylamine moiety.

In certain embodiments, the methods as taught herein may further comprise the step of identifying a 2-pyrrolidinone adduct (e.g., by NMR spectroscopy). The 2-pyrrolidinone adduct may be formed after the reaction of the activated furan moiety with a hydrazide moiety of the second agent.

Identifying the covalent bond between the activated furan moiety and the hydrazine or hydroxylamine moiety is preferably performed by any adequate technique known to the skilled person for protein mass spectrometry (MS) analysis, preferably by gel electrophoresis, gas chromatography-mass spectrometry (GC-MS), liquid chromatography-mass spectrometry (LC-MS), high performance liquid chromatography-mass spectrometry (HPLC-MS), reversed phase high performance liquid chromatography-mass spectrometry (RP HPLC-MS), matrix-assisted laser desorption/ionization-time of flight (MALDI-TOF), electro spray ionization-mass spectrometry (ESI-MS), inductively coupled plasma-mass spectrometry (ICP-MS), accelerator mass spectrometry (AMS), thermal ionization-mass spectrometry (TI-MS) and spark source mass spectrometry (SS-MS), more preferably by gel electrophoresis, liquid chromatography-mass spectrometry (LC-MS), matrix-assisted laser desorption/ionization-time of flight (MALDI-TOF) or electro spray ionization-mass spectrometry (ESI-MS). These techniques for protein mass spectrometry analysis can optionally be preceded by a tryptic digest. The methods as described herein can thus be easily monitored by analytical techniques.

RP-HPLC is generally used to monitor the reaction progress according to the retention time of the analytes which is related to the polarity of the analytes. Measurement of the absorbance by a UV detector may be helpful in monitoring the different steps of the methods as taught herein, e.g., a furan-peptide is highly absorbing at 214 nm whereas the oxidized form absorbs less and it is more polar. For instance, a peptide-second agent conjugate will usually be more polar (except with thiosemicarbazide used herein) with higher absorbance at 254, 280, and 360 nm.

MALDI-TOF analysis may provide information on the mass of the molecules involved.

Identifying the covalent bond between the activated furan moiety and the hydrazine or hydroxylamine moiety is preferably performed by nuclear magnetic resonance (NMR) spectroscopy as known in the art. NMR spectroscopy analysis may provide information on the structure and the stereochemistry of the formed species.

A further aspect provides the products obtained or obtainable by the methods as described herein. Hence, a further aspect provides a first agent-second agent conjugate obtained or obtainable by a method or process for site-selective coupling of a first agent to a second agent, comprising the steps of: a) providing a first agent comprising at least one furan moiety; b) contacting said first agent with an activation signal, thereby activating said furan moiety to an activated furan moiety; c) contacting said activated furan moiety with a second agent comprising at least one hydrazine moiety or at least one hydroxylamine moiety; and d) reacting said activated furan moiety with the hydrazine moiety or the hydroxylamine moiety, thereby site-selectively coupling said first agent to said second agent. Advantageously, first agent-second agent conjugates as taught herein are stable under storage conditions, and hence suitable for long-term biological studies.

Furthermore, the first agent-second agent conjugates as taught herein may be irreversibly formed.

The term "first agent-second agent conjugate", "conjugate", or "bio-conjugate" as used herein refers to a complex comprising at least the first agent as taught herein covalently bound to the second agent as taught herein via a bond formed by reacting the activated furan moiety and the hydrazine or hydroxylamine moiety.

In certain embodiments, a first agent-second agent conjugate as taught herein can be used to study localization, trafficking, and activities of a first agent such as a peptide, for instance in living cells, by fluorescent bioimaging techniques as known in the art.

In certain embodiments, a first agent-second agent conjugate as taught herein can be used in therapeutics. For instance, the first agent-second agent conjugates as taught herein may be antibody-drug conjugates. In order to avoid the side effects of traditional chemotherapeutic agents in cancer treatments, cytotoxic drugs can be coupled to antibodies which allow the targeting of the drug to its site of action, e.g., the cancer cell. In this way, antibody-drug conjugates allow discrimination between healthy cells or tissue and diseased cells or tissue.

In embodiments, the methods as taught herein can be used for coupling a carrier peptide to a therapeutic small molecule (e.g., drug). The carrier peptide can promote the delivery of the therapeutic small molecule into cells, can reduce the toxicity of the therapeutic small molecule or can prolong its stability and/or activity following its administration to a subject. The peptide-second agent conjugates as taught herein can therefore find therapeutic and/or pharmaceutical use e.g. in combination with a suitable pharmaceutical carrier.

A further aspect thus provides pharmaceutical compositions comprising a therapeutic and/or prophylactic effective amount of the first agent-second agent conjugates as taught herein, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering peptides are well known in the art and can be applied to administration of the first agent-second agent conjugates as taught herein.

The terms "pharmaceutical formulation" and "pharmaceutical composition" may be used interchangeably herein. The terms "formulation" and "composition" may be used interchangeably herein.

Administration is by any of the routes normally used for introducing a molecule into ultimate contact with blood or tissue cells. The first agent-second agent conjugates as taught herein are administered in any suitable manner, optionally with one or more pharmaceutically acceptable carriers. Suitable methods of administering the first agent-second agent conjugates as taught herein to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Pharmaceutically acceptable carriers and excipients are well known in the art, and one or more first agent-second agent conjugates as taught herein can be formulated into pharmaceutical compositions by well-known methods (see, e.g., Remington: The Science and Practice of Pharmacy, 21st edition, A. R. Gennaro, Ed., Mack Publishing Company, 2005; Pharmaceutical Formulation Development of Peptides and Proteins, S. Frokjaer and L. Hovgaard, Eds., Taylor & Francis, 2000; and Handbook of Pharmaceutical Excipients, 3rd edition, A. Kibbe, Ed., Pharmaceutical Press, 2000).

The first agent-second agent conjugates as taught herein can be administered by a number of routes including, but not limited to: oral, intravenous, intraperitoneal, intramuscular, transdermal, subcutaneous, topical, sublingual, or rectal means. The first agent-second agent conjugates as taught herein can also be administered via liposomes. Such administration routes and appropriate formulations are generally known to those of skill in the art. The first agent-second agent conjugates as taught herein, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intra-articular (in the joints), intravenous, intramuscular, intra-dermal, intra-peritoneal, and sub-cutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials.

Parenteral administration and intravenous administration are preferred methods of administration. In particular, the routes of administration already in use for conjugate therapeutics, along with formulations in current use, provide preferred routes of administration and formulation for the first agent-second agent conjugates as taught herein.

The dose administered to a patient, in the context of the present invention, is sufficient to effect a beneficial therapeutic response in the patient over time, or, e.g., to inhibit infection by a pathogen, to reduce or prevent the symptoms of a disease state, or other appropriate activity, depending on the application. The dose is determined by the efficacy of a particular composition/formulation, and the activity, stability or serum half-life of the carrier peptide-therapeutic drug bio-conjugate employed and the condition of the patient, as well as the body weight or surface area of the patient to be treated. The size of the dose is also determined by the existence, nature, and extent of any adverse side-effects that accompany the administration of a particular composition, or the like in a particular patient.

In determining the effective amount of the composition/formulation to be administered in the treatment or prophylaxis of disease (e.g., cancers, inherited diseases, diabetes, AIDS, or the like), the physician evaluates circulating plasma levels, formulation toxicities, progression of the disease, and/or where relevant, the production of bio-conjugate antibodies.

The dose administered, e.g., to a 70 kilogram patient, is typically in the range equivalent to dosages of currently-used therapeutic proteins, adjusted for the altered activity or serum half-life of the relevant first agent-second agent conjugates. The first agent-second agent conjugates as taught herein can supplement treatment conditions by any known conventional therapy, including antibody administration, vaccine administration, and administration of cytotoxic agents, natural amino acid polypeptides, nucleic acids, nucleotide analogues, biologic response modifiers, and the like.

For administration, formulations of the bio-conjugates as taught herein are administered at a rate determined by the LD-50 of the relevant formulation, and/or observation of any side-effects of the first agent-second agent conjugates as taught herein at various concentrations, e.g., as applied to the mass and overall health of the patient.

Administration can be accomplished via single or divided doses. General Methods for preparing administrable compositions are known to those skilled in the art and are described in more detail in e.g., Remington: The Science and Practice of Pharmacy, 21st edition, A. R. Gennaro, Ed., Mack Publishing Company (2005).

A variety of subjects can benefit from the therapeutic treatments, and/or prophylactic treatments provided by the first agent-second agent conjugates as taught herein. Humans, and animals including, but not limited to, domestic livestock, such as cows, pigs, goats, sheep, chickens, and/or other common farm animals can be administered compositions and formulations that include the conjugates described herein. Common household pets, e.g., cats, dogs, parrots, parakeets, doves, etc., can also benefit from being administered therapeutic or prophylactic first agent-second agent conjugates as taught herein.

A further aspect provides a kit comprising a first agent comprising at least one furan moiety, a second agent comprising at least one hydrazine moiety or at least one hydroxylamine moiety, and components or instructions for coupling said first agent with said second agent according to the methods as taught herein. In embodiments, the kits comprise a first agent comprising at least one furan moiety, a second agent comprising at least one hydrazine moiety or at least one hydroxylamine moiety, and instructions for coupling said first agent with said second agent according to the methods as taught herein. In particular embodiments, the kits comprise instructions for coupling said first agent with said second agent according to the methods as taught herein.

In certain embodiments, the kits comprise furan-peptides comprising at least one furan moiety, second agents comprising at least one hydrazine moiety or at least one hydroxylamine moiety, and components or instructions for coupling said furan-peptides with said second agents according to the methods as taught herein. In certain embodiments, the kits comprise furan-peptides comprising at least one furan moiety, second agents comprising at least one hydrazine moiety or at least one hydroxylamine moiety, and instructions for coupling said furan-peptides with said second agents according to the methods as taught herein. In particular embodiments, the kits comprise instructions for coupling said furan-peptides with said second agents according to the methods as taught herein.

Amino acids with their three letter code and one letter code are listed in Table 1.

TABLE 1

Amino acids with their three letter code and one letter code

| Amino acid | Three letter code | One letter code |
| --- | --- | --- |
| glycine | Gly | G |
| alanine | Ala | A |
| valine | Val | V |
| leucine | Leu | L |
| isoleucine | Ile | I |
| proline | Pro | P |
| tyrosine | Tyr | Y |
| tryptophan | Trp | W |
| phenylalanine | Phe | F |
| cysteine | Cys | C |
| methionine | Met | M |
| serine | Ser | S |
| threonine | Thr | T |
| lysine | Lys | K |
| arginine | Arg | R |
| histidine | His | H |
| aspartic acid | Asp | D |
| glutamic acid | Glu | E |
| asparagine | Asn | N |
| glutamine | Gln | Q |

EXAMPLES

Material and Methods
Products

Rink Amide AM resin (0.68 mmol/g) was obtained from Novabiochem. All amino acids were purchased from Novabiochem. Fmoc-2-L Furylalanine (Fua) was purchased from PepTech Corporation. L-amino acids were used throughout the synthesis. Dimethylformamide (DMF) peptide synthesis grade and N-methylpyrrolidone (NMP) were purchased from Biosolve. Phosphate Buffered Saline (PBS) without calcium or magnesium was purchased from Lonza. Dichloromethane (DCM) and N,N-diisopropylethylamine (DIPEA) were obtained from Aldrich. Trifluoroacetic acid (TFA) and coupling reagents were obtained from Iris Biotech GmbH. All reagents used for automated peptide synthesis were peptide synthesis grade. Methyl hydrazine was purchased from Acros Organics. Ethyl 3-(furan-2-yl)propionate, hydrazine, isonicotinic hydrazide, Lucifer yellow carbohydrazine (LYCH) dilithium salt, and fluorescein-5-thiosemicarbazide were purchased from Sigma Aldrich, and Alexa fluor 488 hydrazide was obtained from Life technologies. All chemicals were used without further purification.

Peptide Syntheses

Automated peptide syntheses were performed on a 24-reactor block SYRO Multiple Peptide Synthesizer equipped with a vortexing unit (Multisyntech, Witten, Germany). Peptides were synthesized by standard Fmoc/tBu strategy using HBTU/DIPEA couplings.

Photo-Oxidation/Irradiation

Solutions of the furan-peptide containing catalytic amounts of Rose Bengal as photosensitizer were prepared in small test tubes, vials and eppendorfs. Solutions of the furan-peptide containing catalytic amounts of Rose bengal as photosensitizer were prepared in small glass cylindrical, round bottom test tubes of size: 84 mm tall×9 mm inside diameter and/or 100 mm tall×11 mm inside diameter. Test tubes of size (8-15) mm inside diameter×(75-125) mm tall may be used. The solutions were cooled in an ice bath. Air was gently bubbled through the solution while it was irradiated with a Euromex 100 W cold light microscope lamp.

The Euromex Cold light source 100 Watt Halogen LE.5210 was used. The light intensity was adjustable and the color temperature was max 3100K. We used the maximum scale of intensity. This light source is a continuous wave source.

Xenon Variac Eimac Cermax 300 W lamp was used. We used the maximum scale of intensity.

The diameter of the tube containing the sample preferably is within the diameter of the aperture of the light source, e.g. 11 mm. The volume of the solutions preferably should not exceed greatly the diameter of the light source for homogeneously irradiated samples and thus shortened reaction time (herein 1-1.5 mL). Additionally, it is suggested in the context of this instrumentation, that the solution volume is no lower than 1 mL, for better air bubbling through the solution.

The solutions were placed perpendicularly and well-aligned to the light source, in order for the whole sample to be irradiated. Distance from the light source was minimal to 20 mm.

Samples were irradiated for 2-60 min. Irradiation time varied from 2-60 min depending on the type of the peptide, the solvent, the concentration of the peptide, and the sensitizer as well as the irradiation set-up (e.g. alignment to the lamp). Irradiation time also varied depending on the lamp.

Analyses

ESI-MS spectra were recorded using an LCQ ion trap mass spectrometer (Finnigan MAT). RP-HPLC analyses were performed on an Agilent 1100 Series instrument with a Phenomenex Luna $C_{18}$ column (250×4.6 mm, 5 μm (particle size) at 35° C.). A flow rate of 1 ml/min was used with the following solvent systems: 0.1% TFA in $H_2O$ (A) and MeCN (B). The column was flushed for 3 min with 100% A, then a gradient from 0 to 100% B over 15 min was used, followed by 5 min of flushing with 100% B. The column was flushed for 3 min with 100% A, then a gradient from 0 to 60% B when monitoring labeling of Rev peptide, over 15 min, followed by 5 min of flushing with 100% B.

Preparative purification was performed on an Agilent Technologies PrepStar instrument using a Phenomenex Luna C18 column (250×21.2 mm, 5 μm particle size at 35° C.). The analyses were executed with a flow rate of 3 mL/min and with the following solvent systems: 0.1% TFA in $H_2O$ (A) and MeCN (B). The column was flushed for 2 min with 100% A, then a gradient from 0 to 100% B, followed by 5 min of flushing with 100% B. (ESI-)LC-MS data were collected on an Agilent 1100 Series instrument with a Phenomenex Kinetex C18(2) column (150×4.6 mm, 5 μm at 35° C.) connected to an G1956B type SL mass detector with a flow rate of 1 ml/min was used with the following solvent systems: 5 mM $NH_4OAc$ in $H_2O$ (A) and MeCN (B). The column was flushed with 100% A for 2 min, then a gradient from 0 to 100% B over 15 min was used, followed by 5 min of flushing with 100% B, except in the case of Rev peptide where the column was flushed with 100% A for 2 min, then a gradient from 0 to 60% B over 15 min was used, followed by 5 min of flushing with 60% B.

HRMS data were recorded on an Agilent 6220A Time-of-Flight MS-detector, using an ESI-APCI multimode ionization source.

Example 1: Synthesis of Furan-Peptides 1, 2, 3, 4, and Cell-Penetrating Rev Peptide The furan-peptides 1, 2, 3, and 4 had the amino acid sequence Ac-Ile-Glu-Lys-amino acid 4 (AA4)-Fua-Lys-$NH_2$ with AA4=Phe for furan-peptide 1 (SEQ ID NO. 1), AA4=Trp for furan-peptide 2 (SEQ ID NO. 2), AA4=His for furan-peptide 3 (SEQ ID NO. 3), and AA4=Met for furan-peptide 4 (SEQ ID NO. 4).

The cell-penetrating Rev peptide had the amino acid sequence DTRQARRNRRRRFuaRERQRAAAAR-$NH_2$ (SEQ ID NO. 5).

Figure 5:
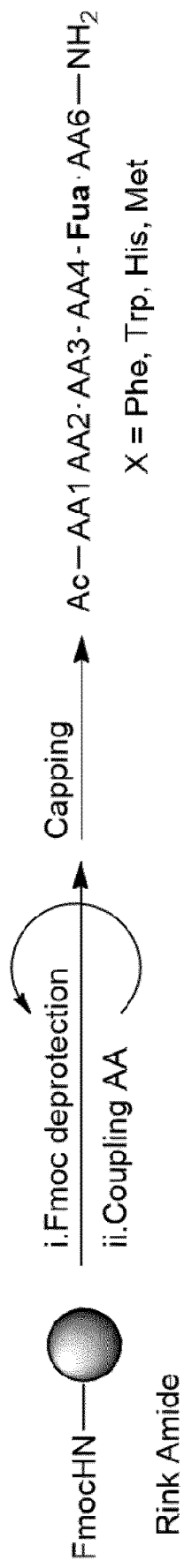
FIG. 5 represents a schematic overview illustrating the synthesis of deprotected furan-peptides, furan-peptide 1 (AA4=Phe), furan-peptide 2 (AA4=Trp), furan-peptide 3 (AA4=His), and furan-peptide 4 (AA4=Met).
Figure 28:
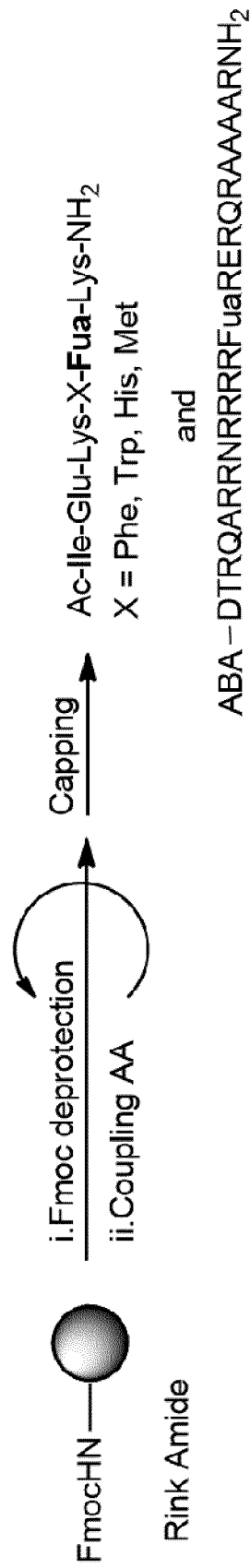
FIG. 28 represents a schematic overview illustrating the synthesis of deprotected furan-peptides, furan-peptide 1 (X=Phe), furan-peptide 2 (X=Trp), furan-peptide 3 (X=His), furan-peptide 4 (X=Met), and Rev peptide.

FIG. 5 provides a schematic overview illustrating the synthesis of a deprotected furan-peptide such as furan-peptide 1 (AA4=Phe), furan-peptide 2 (AA4=Trp), furan-peptide 3 (AA4=His), and furan-peptide 4 (AA4=Met). FIG. 28 provides a schematic overview illustrating the synthesis of a deprotected furan-peptide such as furan-peptide 1 (X=Phe), furan-peptide 2 (X=Trp), furan-peptide 3 (X=His), and furan-peptide 4 (X=Met) and Rev peptide.

The resin was preswollen in DMF for 30 min and then filtered off. Peptide synthesis was performed on an automated peptide synthesizer using the following protocols for Fmoc deprotection and coupling.

Fmoc Deprotection:

A solution of 20% piperidine in DMF was added to the resin. The resin was shaken for 3 min and filtered off. Procedure was repeated and the reaction mixture was shaken for 12 min. The resin was filtered off and washed with DMF (6×30 s).

Coupling:

5 equivalents (equiv.) of a 0.5 M solution of amino acid in DMF, 5 equiv. of a 0.5 M solution of HBTU in DMF, and 10 equiv. of a 2.0 M solution of DIPEA in NMP were added to the resin. The reaction mixture was shaken for 40 min. The resin was filtered off and washed with DMF (4×30 s). The furylalanine coupling was conducted manually using a solution of 3.0 equiv. of the amino acid, 3.0 equiv. of HATU and 6.0 equiv. of DIPEA in DMF. For difficult couplings, this step was repeated once.

Capping:

For peptides 1, 2, 3, and 4: 6 equiv. of acetic anhydride and DIPEA in DMF were added to the resin. The reaction mixture was shaken for 30 min, filtered off and washed with DMF (3×30 s). The capping was repeated once to ensure complete conversion. For the cell-penetrating Rev peptide: 10 equiv. 4-acetamido benzoic acid, 20 equiv. of DIPEA, and 10 equiv. HBTU in DMF were added to the resin. The reaction mixture was shaken for 2 hours, filtered off, and washed with DMF (3×30 s). This was repeated a second time if needed.

Cleavage and Deprotection of Peptides:

For peptides 1, 2, 3, and 4: the resin (1 mg) was treated with 300 μl of TFA/TIS/$H_2O$ (95:2.5:2.5), after 2 hours, the liquid was filtered off and the resin was washed 3 times with TFA. The filtrate was evaporated and redissolved in MQ H₂O for HPLC and LC-MS analysis. For the cell-penetrating Rev peptide: the resin was treated with (1 mL cocktail/10 mg resin): 375 mg phenol, 500 µL mQ, 250 µL thioanisole, 125 µL ethanedithiol and 5 mL TFA. The cocktail was added dropwise on ice. The mixture was then allowed to stir for 15 minutes on ice and for 3 hours at room temperature. After 2 hours, the liquid was filtered off and the resin was washed 3 times with TFA. The filtrate was evaporated and redissolved in MQ H₂O for HPLC and LC-MS analysis.

Example 2: General Procedure for the Preparation of the Labeled Peptides According to an Embodiment of the Present Invention Furan-modified peptides (0.2-6 µmol) were dissolved in aqueous solution (usually 1-1.5 mL), containing catalytic amounts of Rose bengal, as photosensitizer (10 µM or $10^{-4}$ M in cases where isonicotinic hydrazide was used). The solutions were cooled with an ice bath. Air was gently bubbled through the solution while it was irradiated with a Euromex 100 W cold light microscope lamp (as described above) or irradiation with a xenon Variac Eimac Cermax 300 W lamp in cases where isonicotinic hydrazide was used.

All reactions were successfully performed in milliQ water at the pH of the peptide solution, except for the experiment where thiosemicarbazide was employed. In that case the peptide was dissolved in PBS (pH 7.3-7.5), enhancing the reactivity of the fluorophore.

The experiments with LYCH dilithium salt were performed successfully at different pH values.

The reactions were monitored by RP-HPLC and MALDI-TOF analysis or by thin-layer chromatography (TLC) in case of ethyl 3-(furan-2-yl)propionate. After completion of the photo oxidation reaction, the corresponding label (e.g., hydrazide) was added at room temperature. The reaction solution was stirred 2 h-48 h. The reaction progress was monitored by RP-HPLC, MALDI-TOF, and LC-MS analysis. The formation of the desired conjugates was confirmed by RP-HPLC, MALDI-TOF and NMR analysis.

Example 3: Synthesis of the 2-Pyrrolidinone Modified Peptide 1

Figure 6:
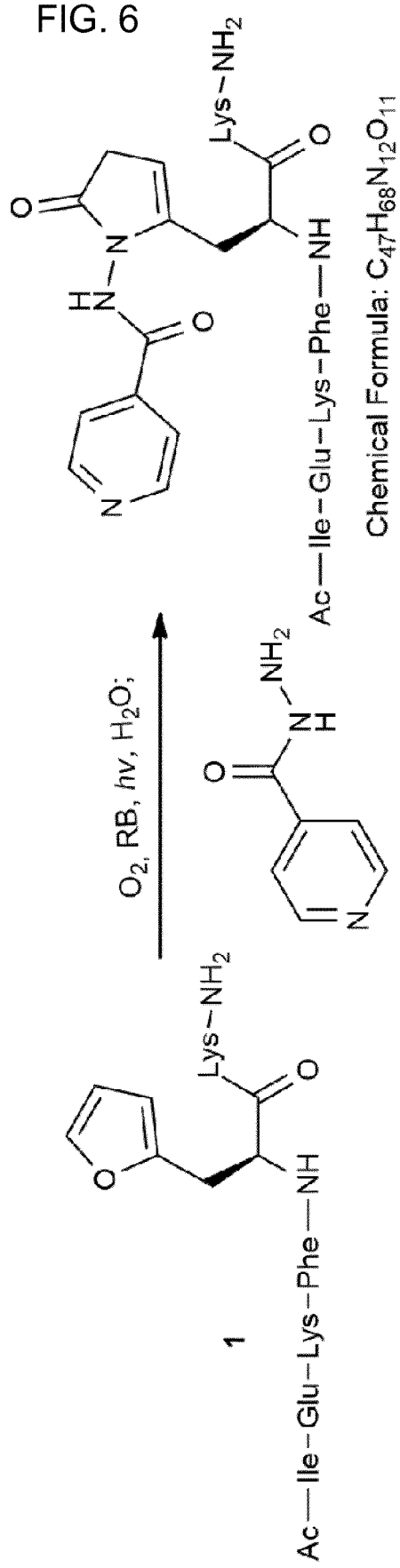
FIG. 6 represents a schematic overview illustrating the synthesis of the 2-pyrrolidinone peptide from furan-peptide 1 and isonicotinic hydrazide.
Figure 7:
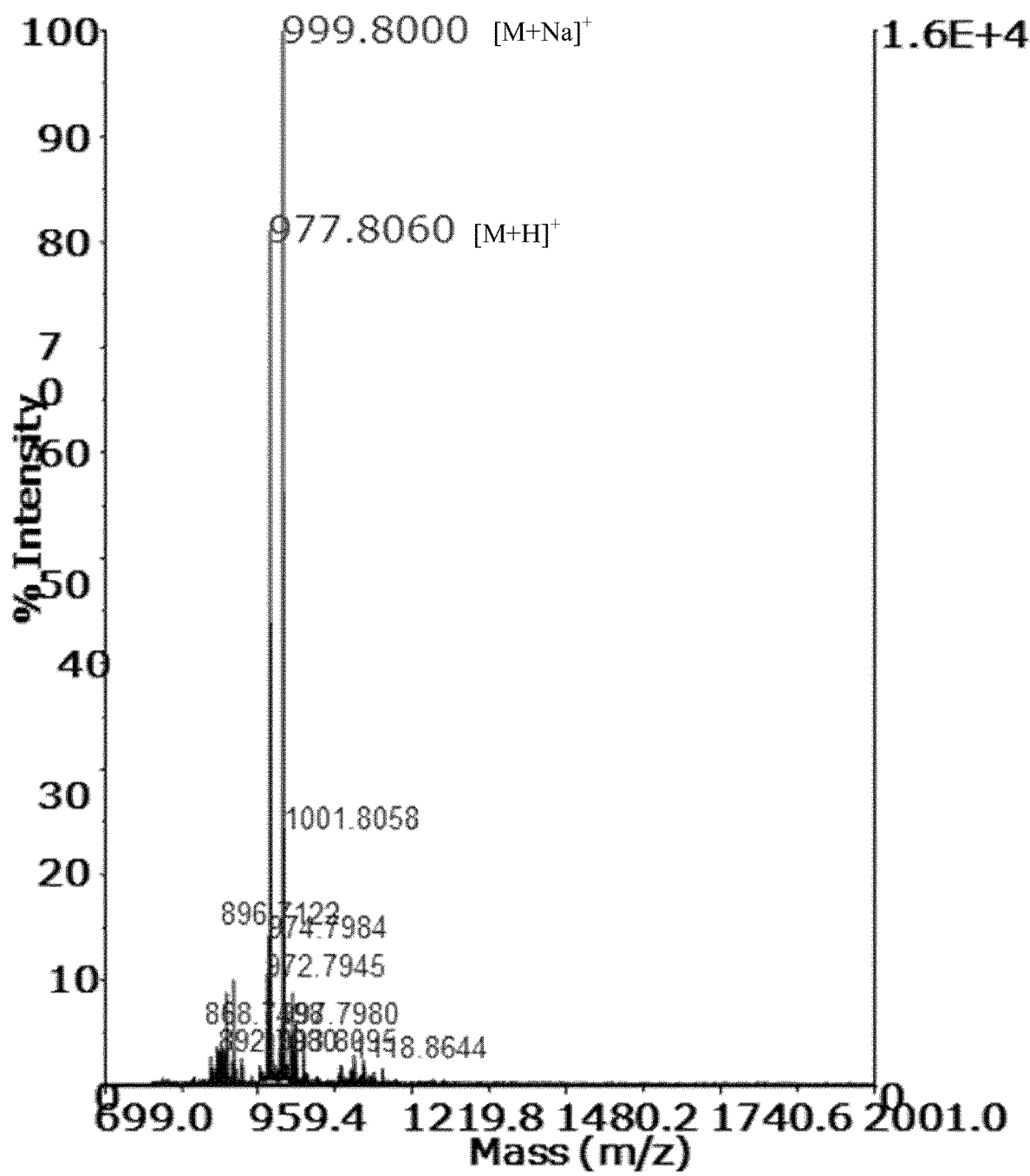
FIG. 7 represents a spectrum illustrating the crude MALDI-TOF analysis of the reaction of furan-peptide 1 and isonicotinic hydrazide after 2 hours.

The coupling reaction of an activated furan-peptide with a second agent comprising a hydrazine moiety, in particular a hydrazide moiety, was first tested using furan-peptide 1 and isonicotinic hydrazide. The reaction was accomplished according to the general experimental set-up described above (Example 2), utilizing furan-peptide 1 (3.0 µmol, added from DMSO stock solution: 20 mg/mL furan-peptide 1 aqueous stock solution containing 10% DMSO) and isonicotinic hydrazide (1.0 equiv., 3.0 µmol, from DMSO stock solution of 1.0 M). Photo-oxidation proceeded in 2.5 mL of aqueous solution (MQ water) for 30 or 40 min, followed by addition of the hydrazide and stirring at room temperature. FIG. 6 illustrates the synthesis of a 2-pyrrolidinone peptide from furan-peptide 1 and isonicotinic hydrazide. Reaction was followed by RP-HPLC and MALDI-TOF analysis. In 30 min the desired product was formed, yet reaction had not reached completion. MALDI-TOF after 2 hours also confirmed the formation of the desired product (FIG. 7). FIG. 8 illustrates the potential mechanism for the oxidation of a furan-peptide and the reaction of an activated furan-peptide with a second agent comprising a hydrazine moiety, in particular a hydrazide moiety (e.g., isonicotinic hydrazide).

Figure 9:
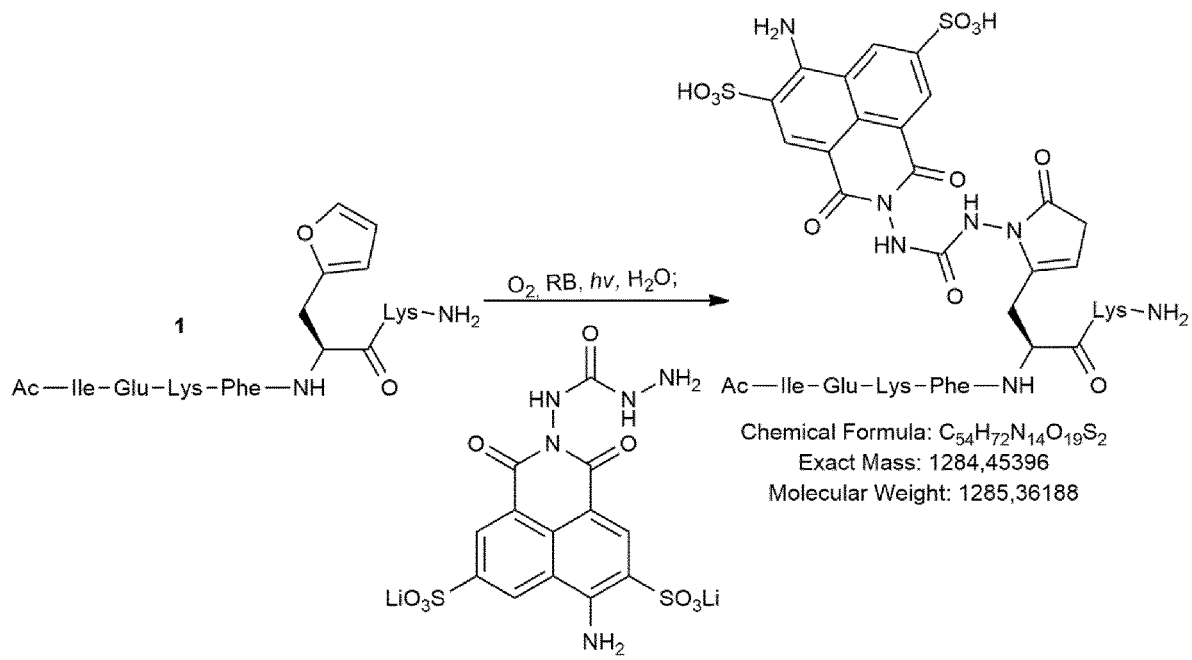
FIG. 9 represents a schematic overview illustrating the coupling of furan-peptide 1 to Lucifer Yellow CH (LYCH) dilithium salt according to an embodiment of the present invention.

Example 4: Labeling of Furan-Peptide 1 with Lucifer Yellow CH (LYCH) Dilithium Salt According to an Embodiment of the Present Invention The coupling of an activated furan-peptide to a second agent, such as a labeling agent, comprising a hydrazine moiety was performed using furan-peptide 1 and Lucifer Yellow CH (LYCH) dilithium salt. The reaction was accomplished according to the general experimental set-up described above (Example 2), utilizing furan-peptide 1 (0.5 µmol, added from aqueous stock solution of 8.3 mM) and LYCH dilithium salt (1.0 equiv, 0.5 µmol, added from aqueous stock solution of 13.8 mM) (FIG. 9). Photo-oxidation was carried out in 1.0 mL of MQ water, for 30 min, followed by addition of the LYCH dilithium salt and stirring at room temperature. FIG. 9 illustrates the coupling of furan-peptide 1 to Lucifer Yellow CH (LYCH) dilithium salt according to an embodiment of the present invention. Reaction was followed by RP-HPLC (FIG. 10) and MALDI-TOF analysis (FIG. 11). The desired product was already formed from 2 hours of stirring (FIGS. 10 and 11).

Figure 10:
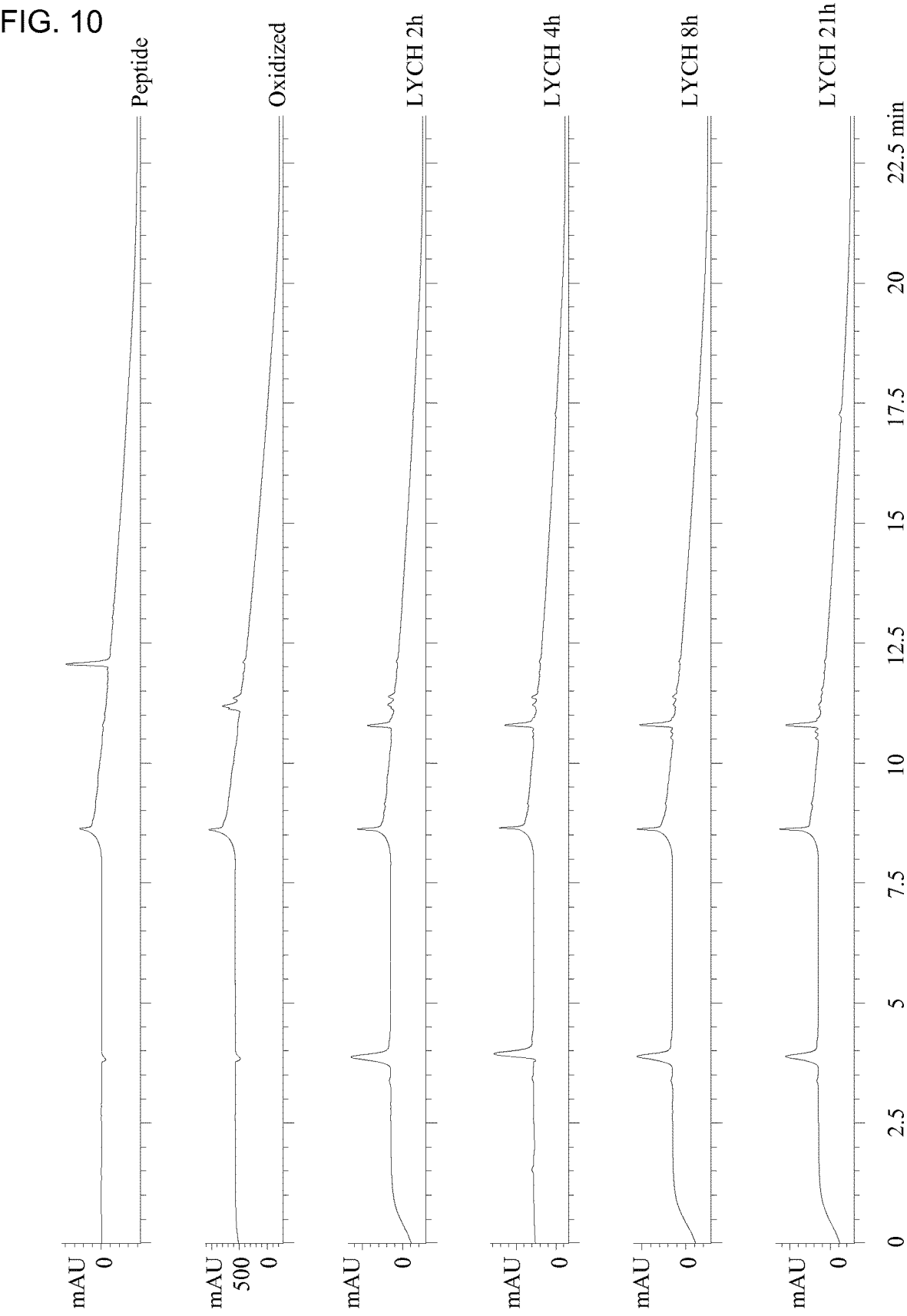
FIG. 10 represents the crude RP-HPLC chromatograms at λ=214 nm illustrating the coupling of the furan-peptide 1 to LYCH dilithium salt and the stability of the labeled peptide over time; from top to bottom: Chromatogram of furan-peptide 1, Chromatogram of activated furan-peptide 1, Chromatogram after 2 h reaction, Chromatogram after 4 h reaction, Chromatogram after 8 h reaction, Chromatogram after 21 h reaction.
Figure 11:
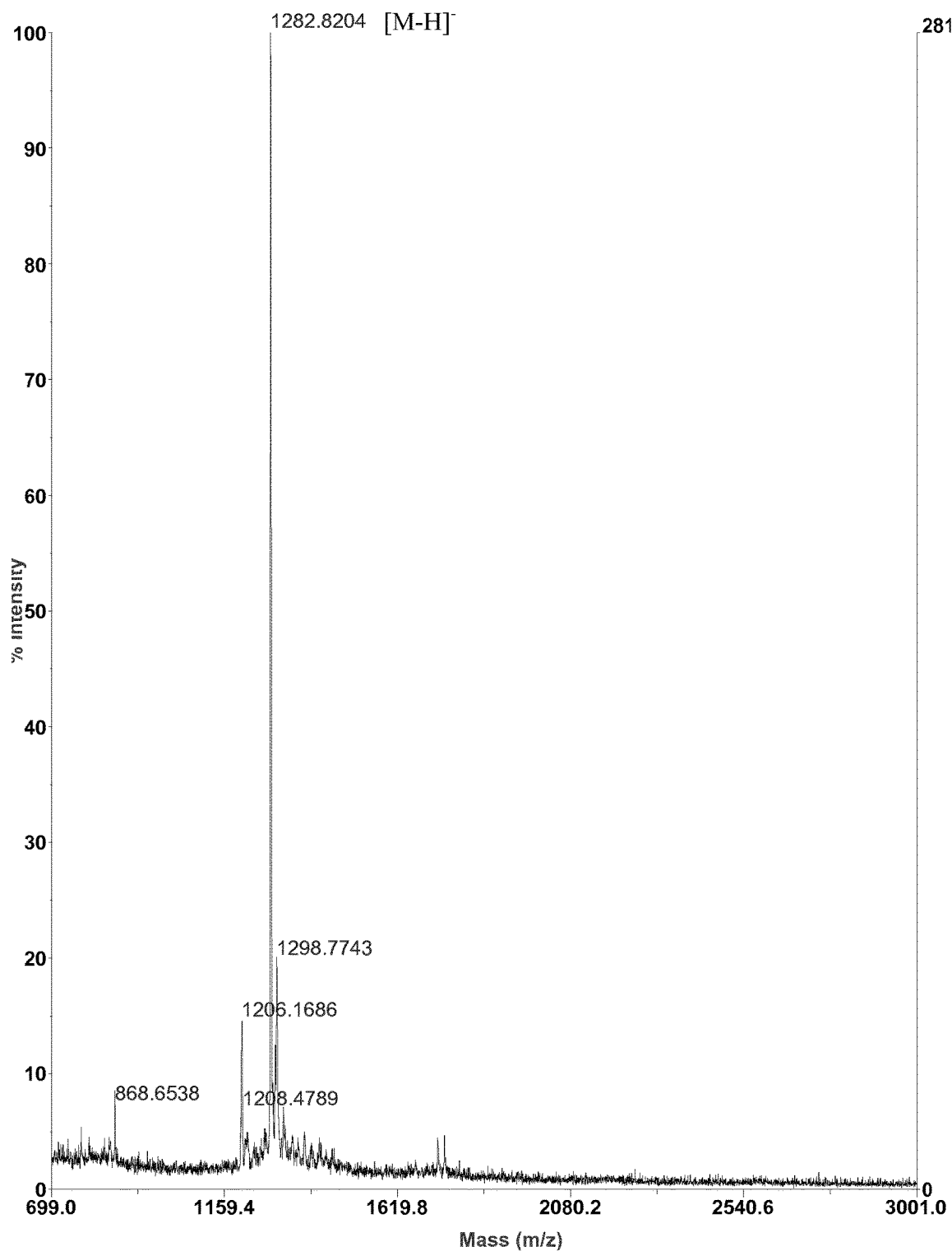
FIG. 11 represents a spectrum illustrating the crude MALDI-TOF analysis of the reaction after 8 hours of reaction.

FIG. 10 represents the crude RP-HPLC chromatograms at A=214 nm illustrating the coupling of the furan-peptide 1 to LYCH dilithium salt and the stability of the labeled peptide over time; from top to bottom: Chromatogram of furan-peptide 1, Chromatogram of activated furan-peptide 1, Chromatogram after 2 h reaction, Chromatogram after 4 h reaction, Chromatogram after 8 h reaction, Chromatogram after 21 h reaction. FIG. 10 illustrates that the reaction was almost completed after 2 hours reaction, using only 1.0 equiv. of LYCH dilithium salt at room temperature. The reaction was completed after 8 h as is illustrated in FIG. 10. FIG. 10 also demonstrates the stability of the labeled peptide over 21 h.

Figure 12:
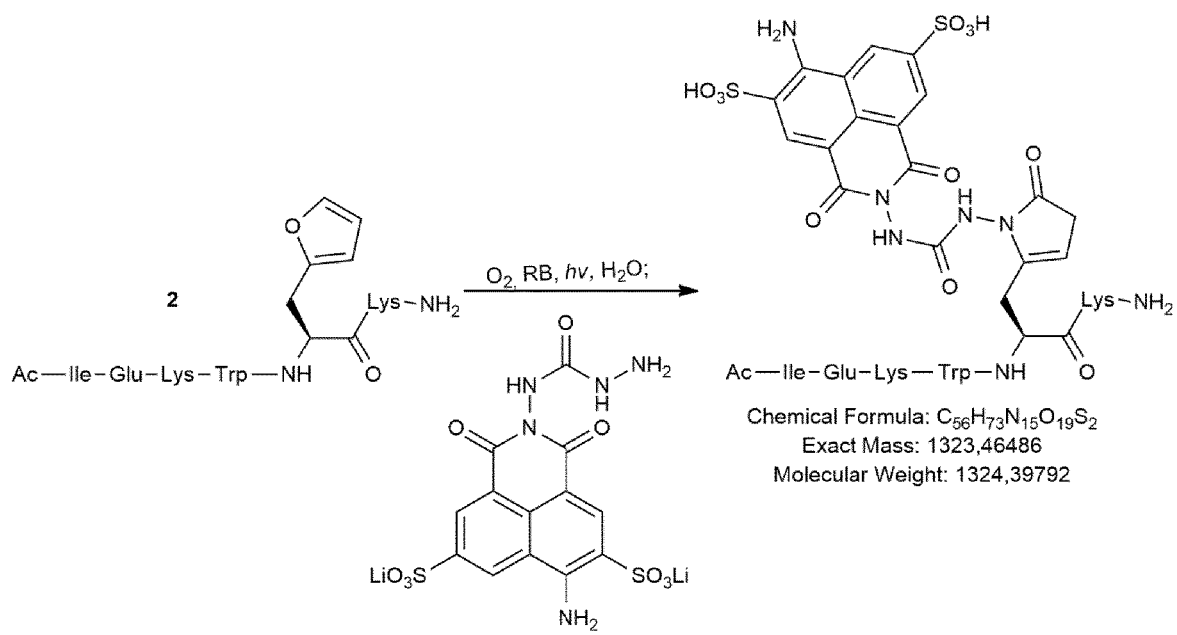
FIG. 12 represents a schematic overview illustrating the coupling of furan-peptide 2 to Lucifer Yellow (LYCH) dilithium salt according to an embodiment of the present invention.
Figure 13:
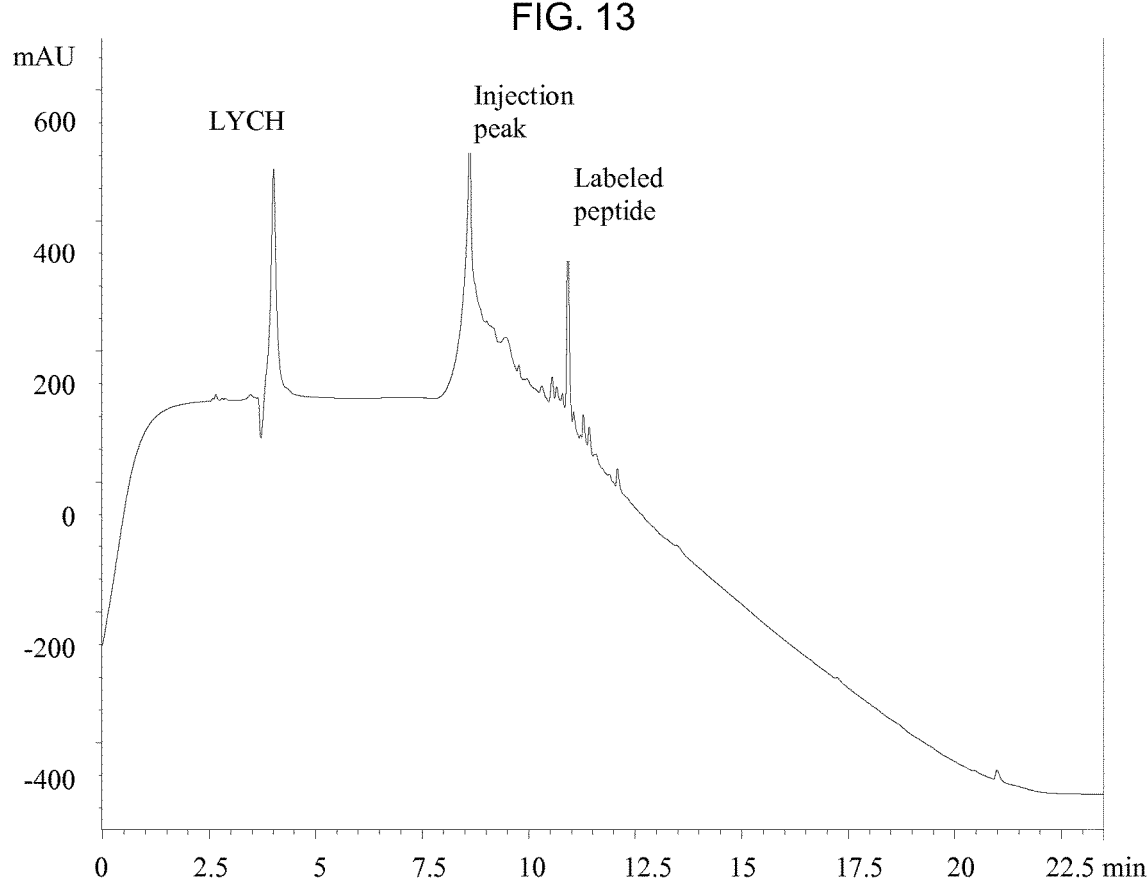
FIG. 13 represents a crude RP-HPLC chromatogram illustrating the coupling of furan-peptide 2 to LYCH dilithium salt after 7 hours of reaction.
Figure 14:
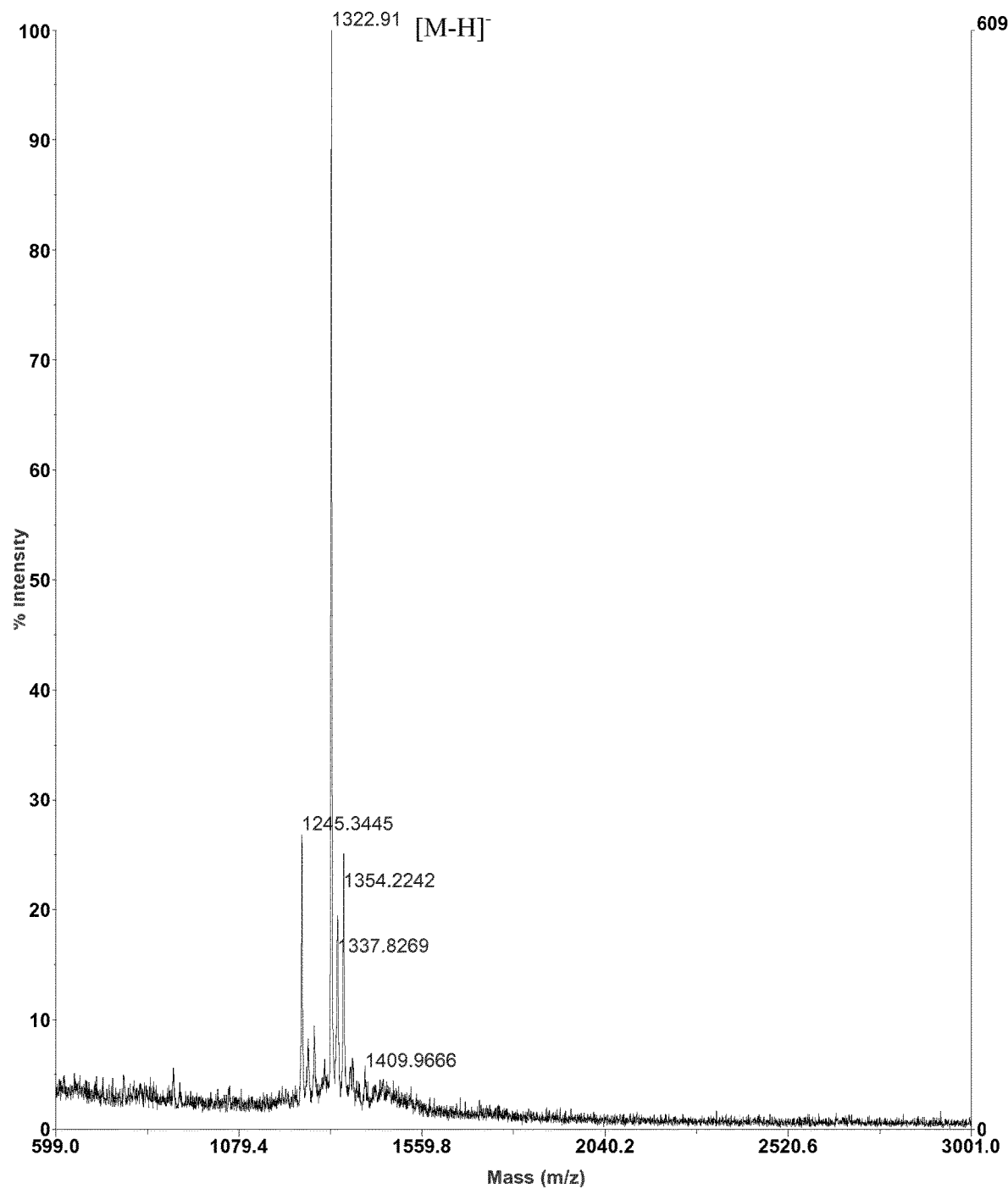
FIG. 14 represent a spectrum illustrating the crude MALDI-TOF analysis of the reaction of furan-peptide 2 and LYCH dilithium salt after 7 hours of reaction.

Example 5: Labeling of Furan-Peptide 2 with Lucifer Yellow CH (LYCH) Dilithium Salt According to an Embodiment of the Present Invention The reaction was accomplished according to the general experimental set-up described above (Example 2), utilizing furan-peptide 2 (0.45 µmol, added from aqueous stock solution of 16.42 mM) activated by a Euromex 100 W cold light microscope lamp and Lucifer yellow CH (1.0 equiv., 0.45 µmol, added from aqueous stock solution of 25.7 mM) (FIG. 12). Photo-oxidation was carried out in aqueous solution of 1.5 mL MQ water, for 50 min, followed by addition of the LYCH dilithium salt and stirring at room temperature. Reaction of furan-peptide 2 and LYCH dilithium salt was followed by RP-HPLC (FIG. 13) and MALDI-TOF analysis (FIG. 14). The desired product was already formed in 7*h* of reaction (FIG. 13, right-hand peak, and FIG. 14).

Figure 15:
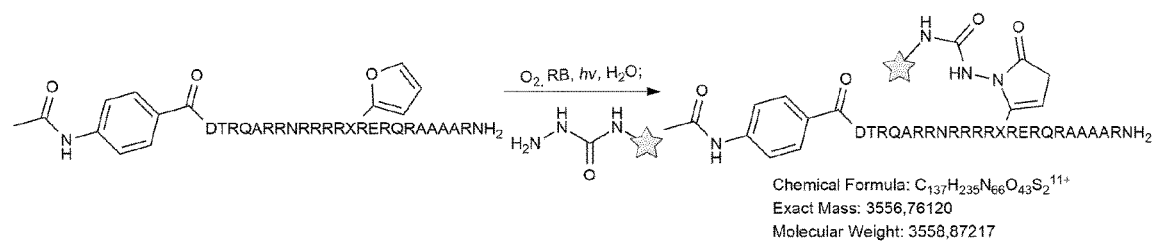
FIG. 15 represents a schematic overview illustrating the coupling of cell-penetrating Rev peptide to Lucifer Yellow CH (LYCH) dilithium salt according to an embodiment of the present invention.
Figure 16:
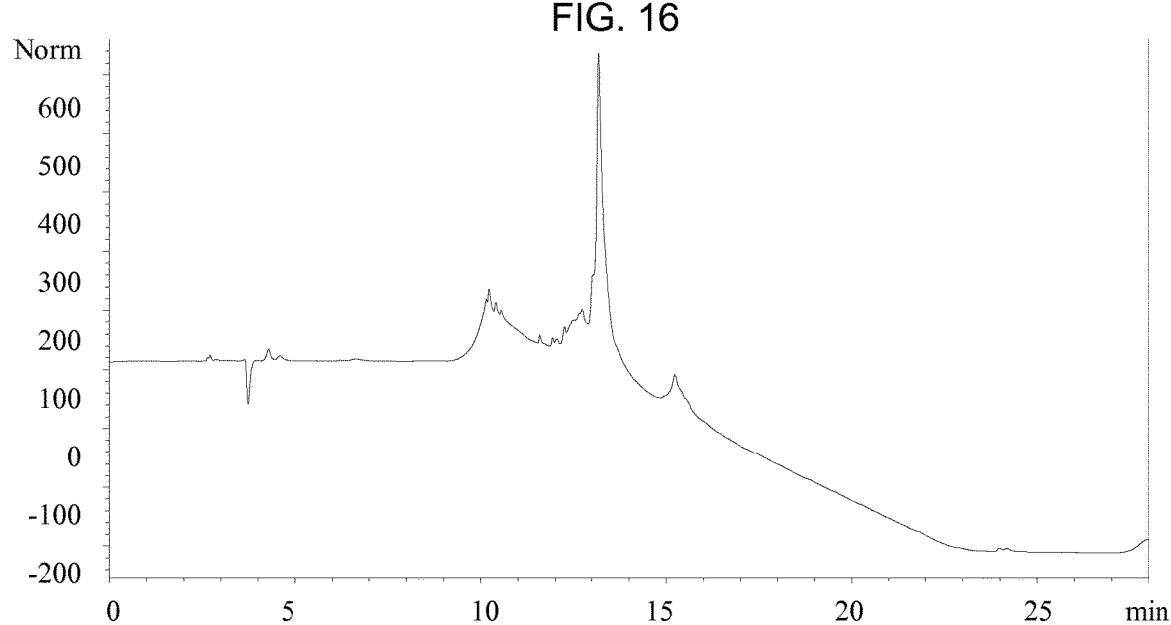
FIG. 16 represents the crude RP-HPLC chromatogram illustrating the coupling of the cell-penetrating Rev peptide to LYCH dilithium salt within 18 h of reaction.
Figure 17:
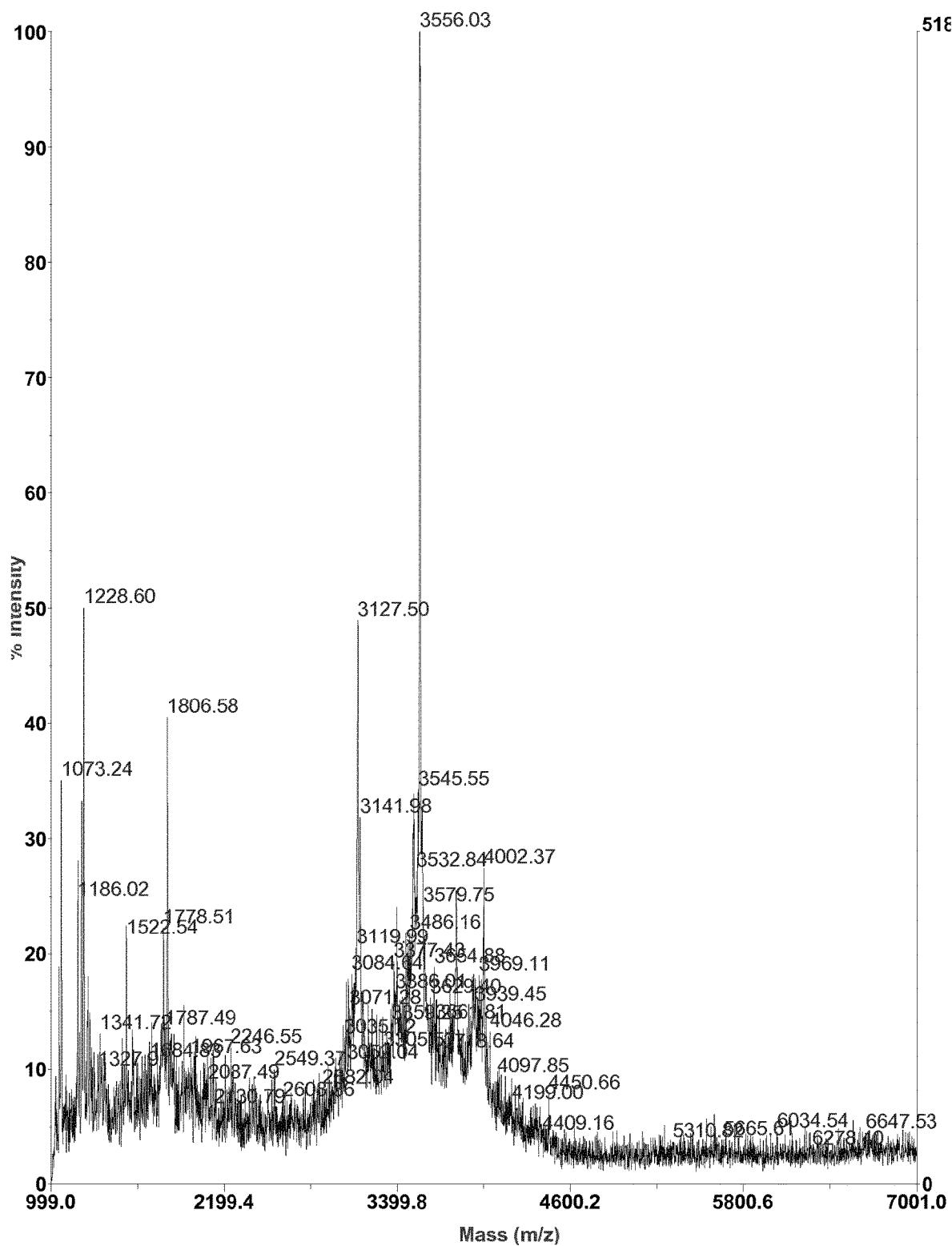
FIG. 17 represents a spectrum illustrating the crude MALDI-TOF analysis of the reaction of the cell-penetrating Rev peptide and LYCH dilithium salt after 18 hours of reaction. The exact mass of the labeled peptide is calculated taking into account that all arginines of the peptide are protonated in the solution.
Figure 34:
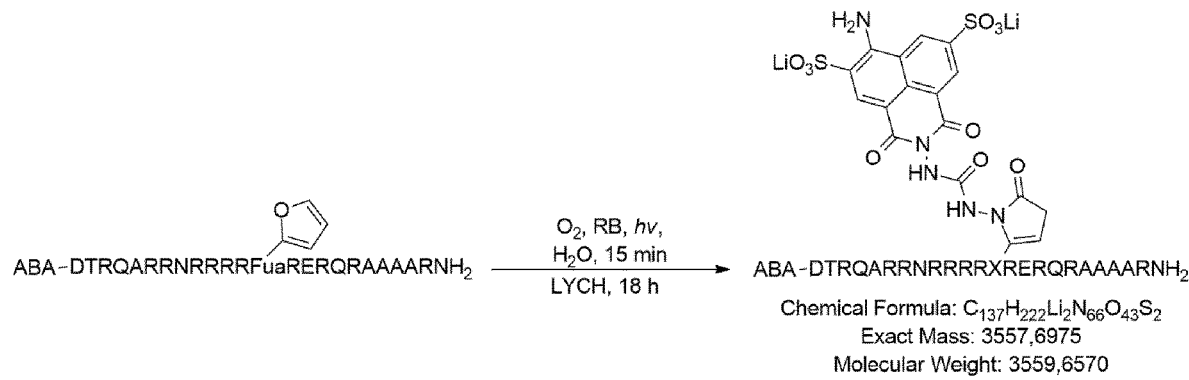
FIG. 34 represents a schematic overview illustrating the coupling of cell-penetrating Rev peptide to Lucifer Yellow CH (LYCH) dilithium salt according to an embodiment of the present invention.

Example 6: Labeling of the Cell-Penetrating Rev Peptide with Lucifer Yellow CH (LYCH) Dilithium Salt According to an Embodiment of the Present Invention The reaction was accomplished according to the general experimental set-up described above, utilizing cell-penetrating Rev peptide (0.36 µmol, added from aqueous stock solution of 11.28 mM) and Lucifer yellow CH (1.0 equiv., 0.36 μmol, added from aqueous stock solution of 35.0 mM) (FIG. 15 and FIG. 34). Photo-oxidation was carried out in aqueous solution of 1.2 mL MQ water, for 15 min, followed by addition of the LYCH dilithium salt and stirring at room temperature. Reaction of cell-penetrating Rev peptide and LYCH dilithium salt was followed by RP-HPLC (FIG. 16 and results not shown) and MALDI-TOF analysis (FIG. 17 and results not shown). The desired product was already formed in 18 hours of stirring (FIG. 16, right-hand peak and FIG. 17, and results not shown).

Figure 18:
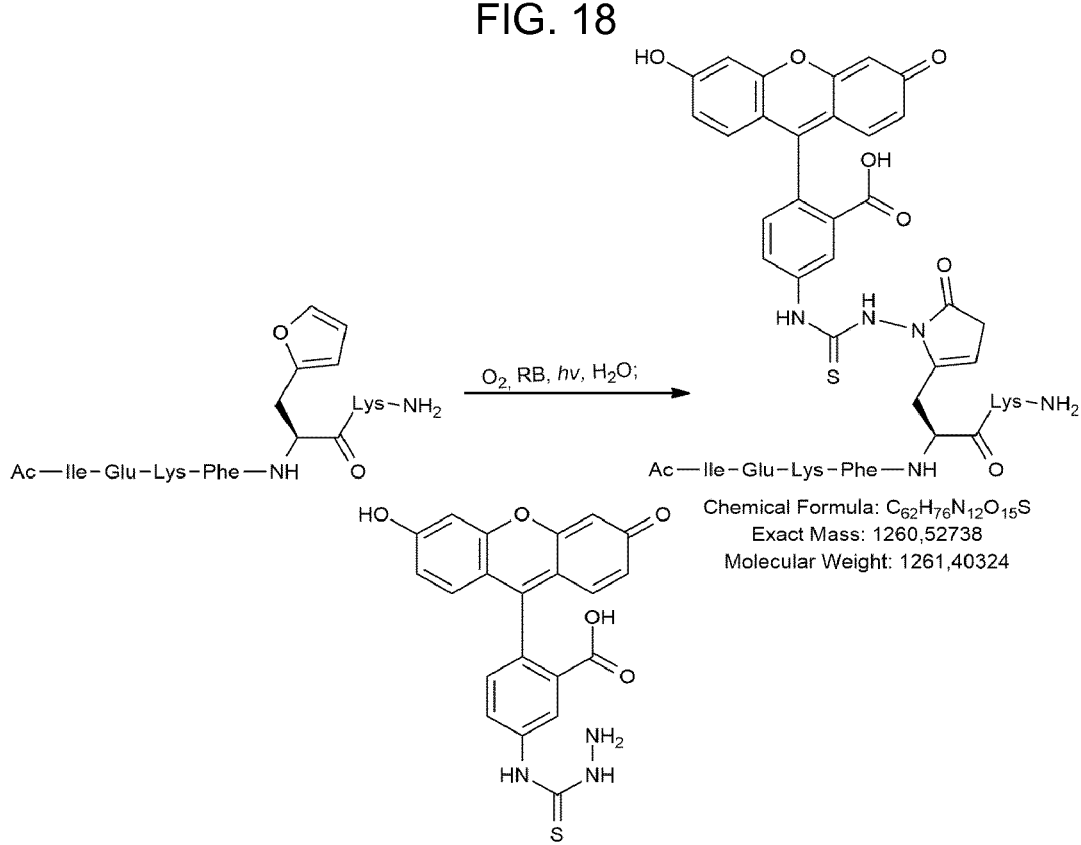
FIG. 18 represents a schematic overview illustrating the coupling of furan-peptide 1 to Fluorescein-5-thiosemicarbazide (FTSC) according to an embodiment of the present invention.
Figure 19:
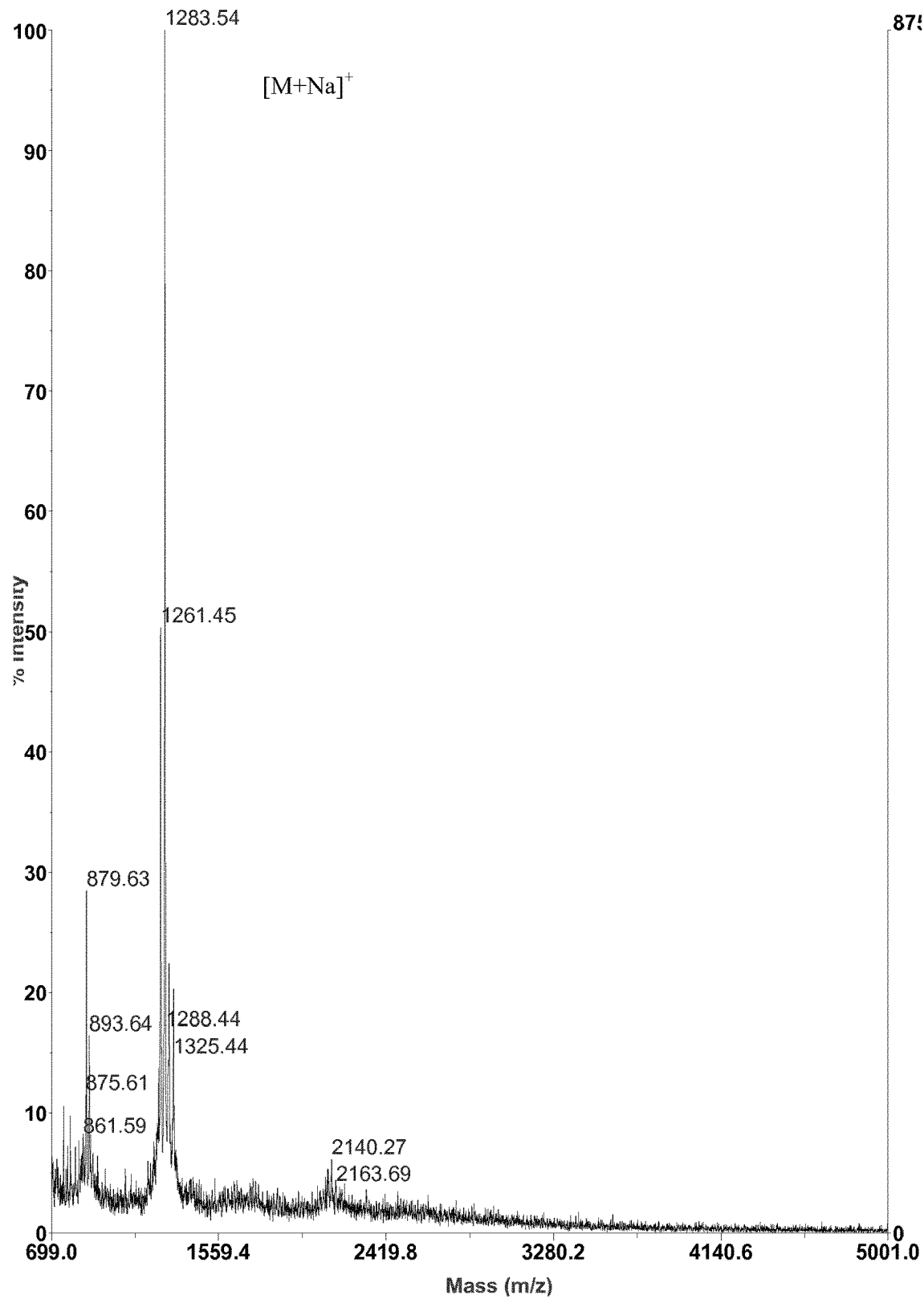
FIG. 19 represents a spectrum illustrating the crude MALDI-TOF analysis of the reaction of furan-peptide 1 and FTSC after 2 days of reaction.

Example 7: Labeling of Furan-Peptide 1 with Fluorescein-5-Thiosemicarbazide (FTSC) According to an Embodiment of the Present Invention The reaction was accomplished according to the general experimental set-up described above, utilizing furan-peptide 1 (0.75 μmol, added from aqueous stock solution of 12.76 mM and Fluorescein-5-thiosemicarbazide (FTSC) (2 equiv., 1.5 μmol, added from DMF stock solution of 0.24 M) (FIG. 18). Photo-oxidation was carried out in 1.5 mL PBS solution (pH 7.3-7.5) for 10 min, followed by addition of the FTSC and stirring at room temperature for 2 days. Reaction of furan-peptide 1 and FTSC was followed by RP-HPLC and MALDI-TOF analysis (FIG. 19). FIG. 19 illustrates the crude MALDI-TOF analysis of the reaction of furan-peptide 1 and FTSC after 2 days (48 h) of reaction.

Figure 20:
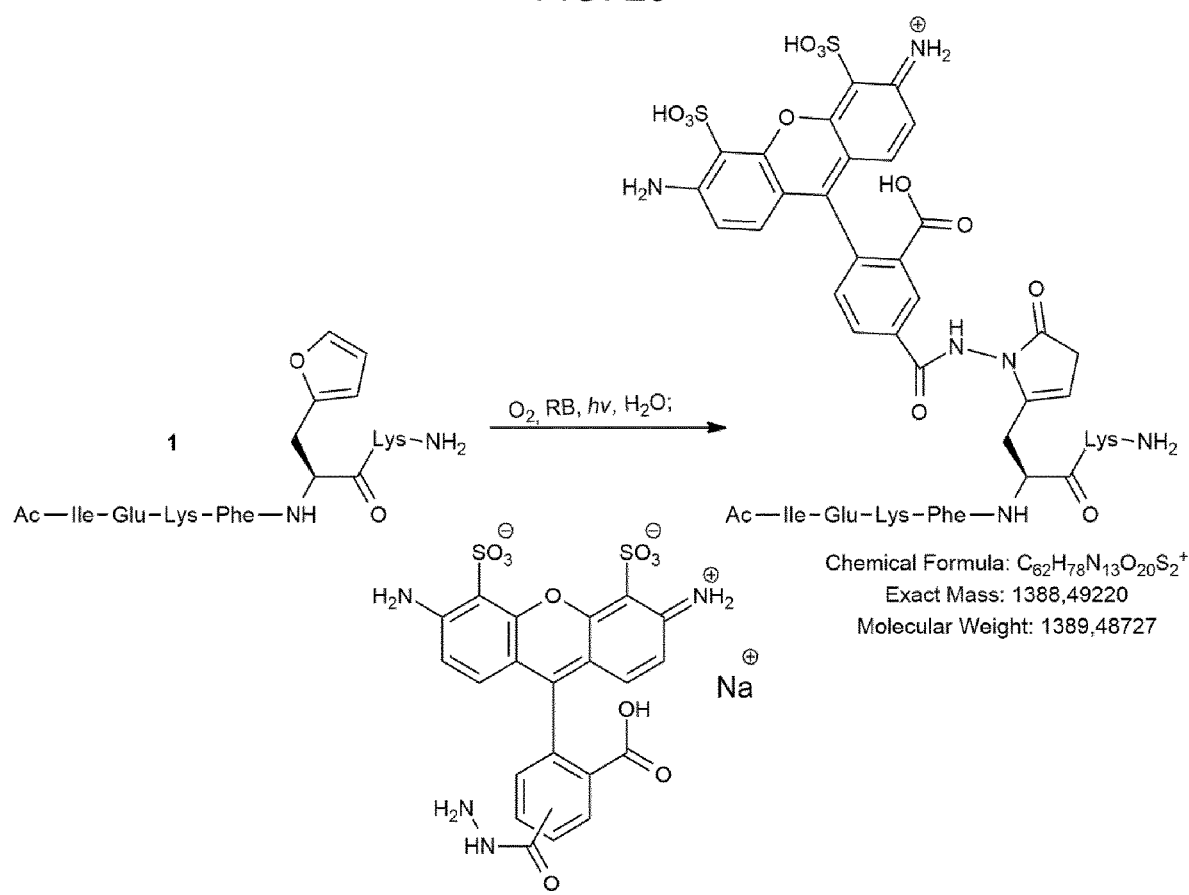
FIG. 20 represents a schematic overview illustrating the coupling of furan-peptide 1 to Alexa Fluor 488 hydrazide according to an embodiment of the present invention.
Figure 21:
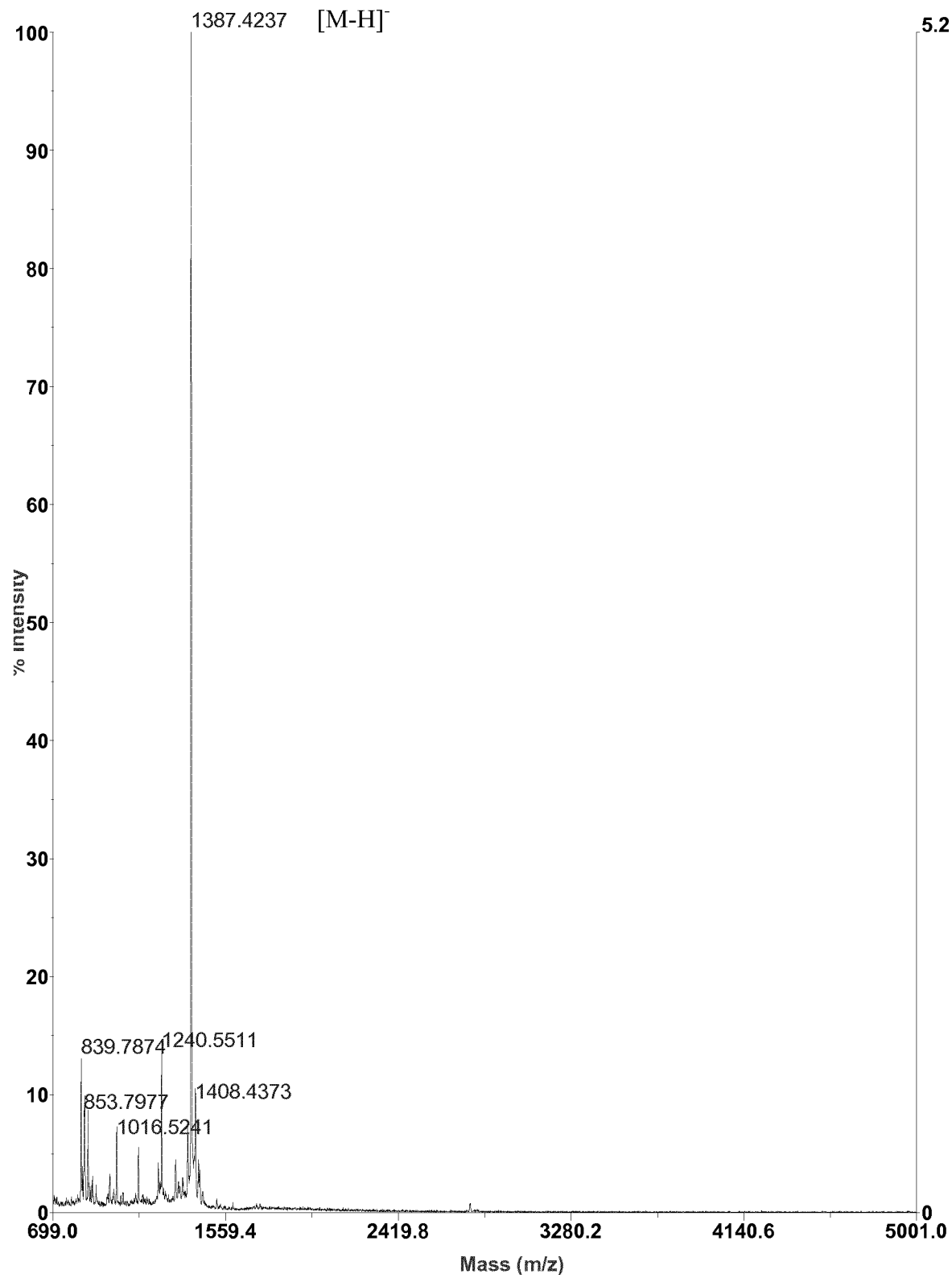
FIG. 21 represents a spectrum illustrating the crude MALDI-TOF analysis of the reaction of furan-peptide 1 and Alexa Flour 488 hydrazide after 4 hours of reaction.
Figure 35:
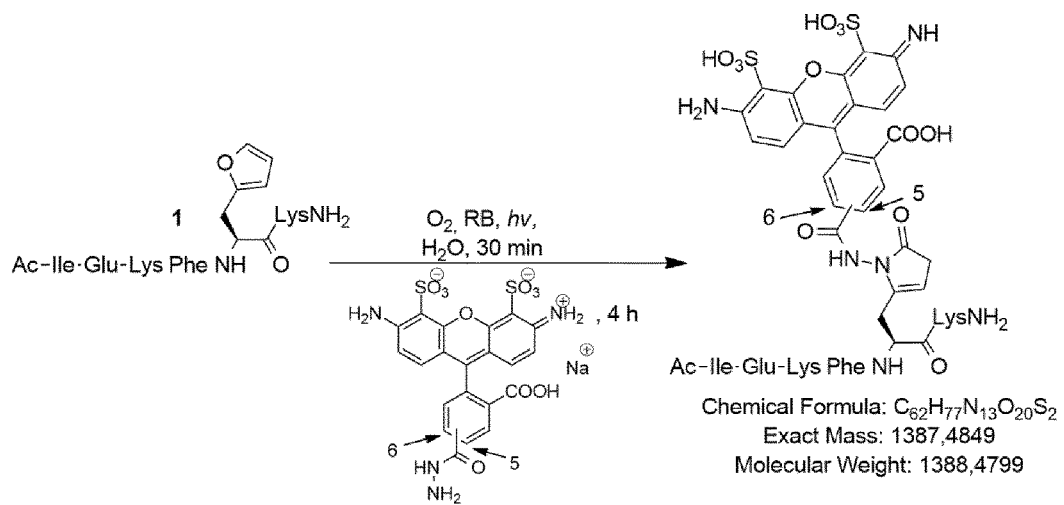
FIG. 35 represents a schematic overview illustrating the coupling of furan-peptide 1 to Alexa Fluor 488 hydrazide according to an embodiment of the present invention.

Example 8: Labeling of Furan-Peptide 1 with Alexa Fluor 488 Hydrazide According to an Embodiment of the Present Invention The reaction was accomplished according to the general experimental set-up described above, utilizing furan-peptide 1 (0.24 μmol, added from aqueous stock solution of 9.86 mM) and Alexa Fluor 488 hydrazide (1.0 equiv., 0.24 μmol, added from aqueous stock solution of 8.76 mM) (FIG. 20 and FIG. 35). Photo-oxidation was carried out in 1.2 mL MQ water, for 30 min followed by addition of the hydrazide and stirring at room temperature. Reaction of furan-peptide 1 and Alexa Flour 488 was followed by RP-HPLC and MALDI-TOF analysis (FIG. 21 and results not shown). The desired product was formed in 4 hours of reaction (FIG. 21 and results not shown).

FIG. 36 illustrates reaction conditions for the labeling of furan-peptide 1 using different fluorophores.

Example 9: Synthesis of a Pyridazine Modified Peptide and a Pyridazinium Cation Modified Peptide In order to investigate the site-specific peptide functionalization, the transformation of a furan-peptide to a pyridazine ring-containing peptide was investigated.

Figure 22:
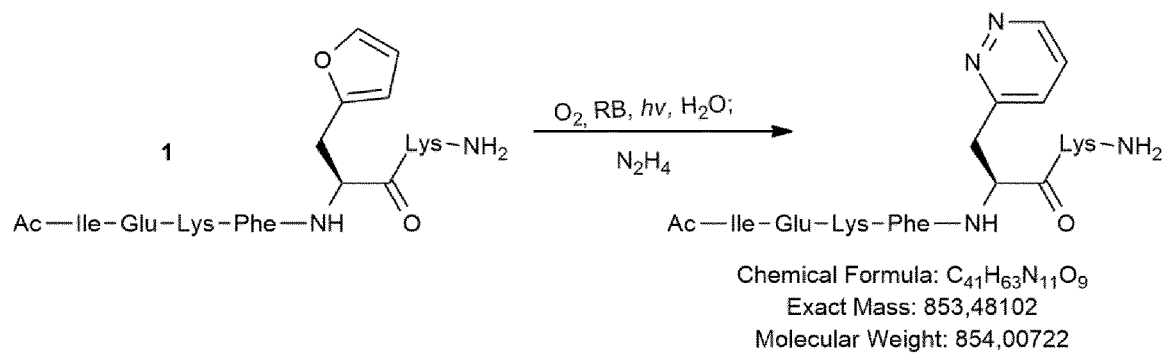
FIG. 22 represents a schematic overview illustrating the synthesis of the pyridazine-modified peptide from furan-peptide 1 and hydrazine.
Figure 37:
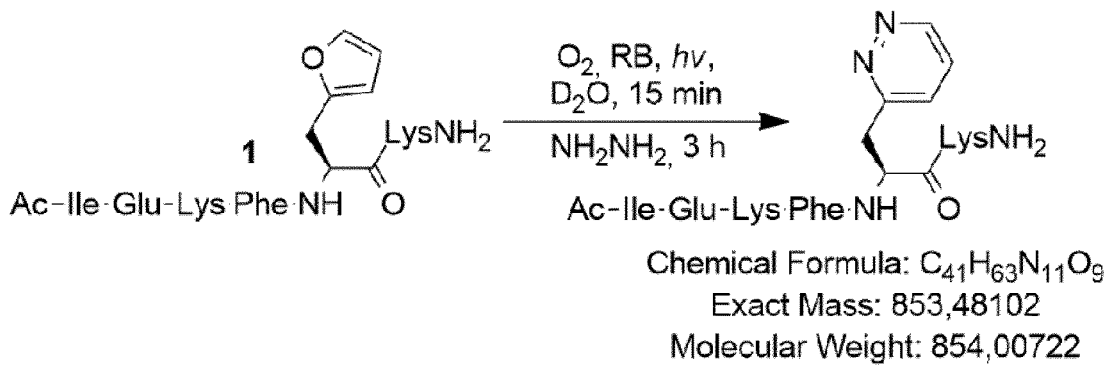
FIG. 37 represents a schematic overview illustrating the synthesis of the pyridazine-modified peptide from furan-peptide 1 and hydrazine.
Figure 38:
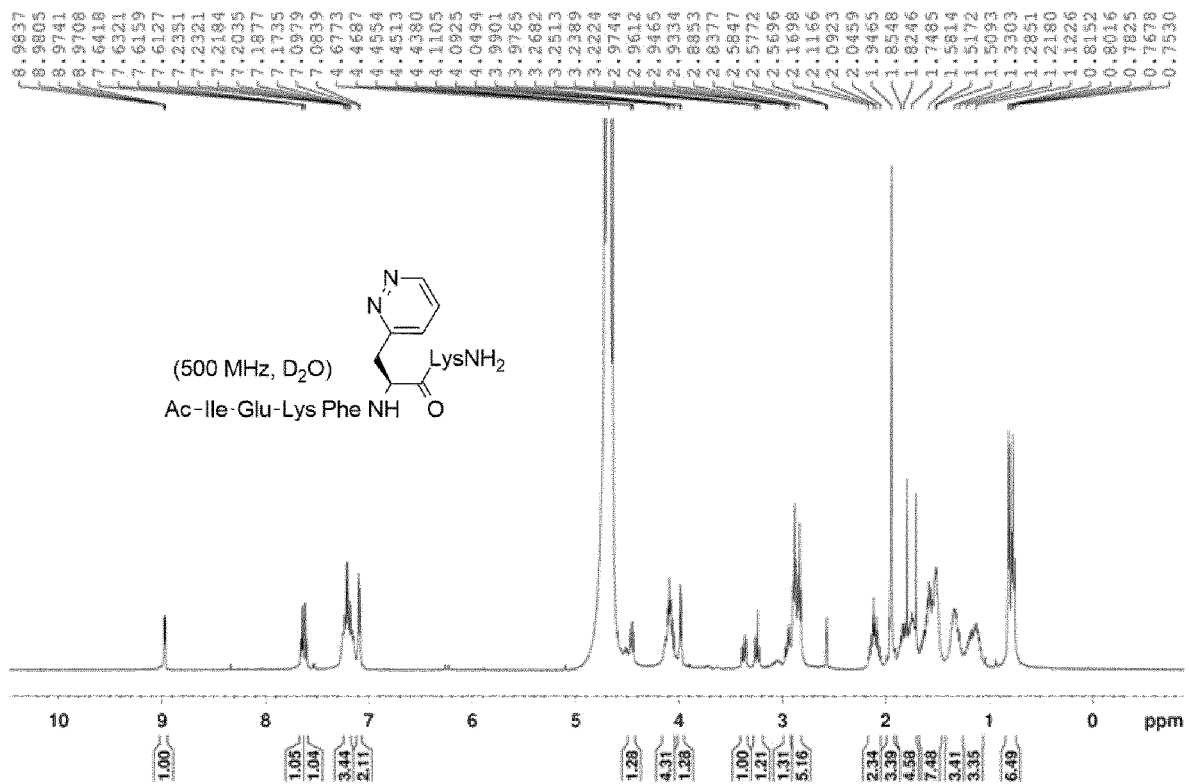
FIG. 38 represents a spectrum illustrating the $^1$H-NMR of the pyridazine adduct synthesized from furan-peptide 1 and hydrazine.

A first reaction was accomplished according to the general experimental set-up described above (Example 2), utilizing furan-peptide 1 (i.e., a phenylalanine-containing peptide) (6 μmol, added from 20 mg/mL $D_2O$ stock solution containing 10% DMSO-d6) and hydrazine (2.0 equiv., from $D_2O$ stock solution) (FIG. 22 and FIG. 37). Photo-oxidation proceeded in 2.5 mL $D_2O$, for 15 min, by irradiation with a xenon Variac Eimac Cermax 300 W lamp, followed by the addition of hydrazine. The mixture was stirred for 3 hours after which $^1$H-NMR confirmed the formation of a pyridazine ring with characteristic peaks at δ=7.61 ppm, 7.65 ppm and 9 ppm (8.98 ppm) (FIG. 38 and results not shown). The desired adduct was also confirmed by LC-MS and MALDI-TOF analysis (results not shown).

Figure 23:
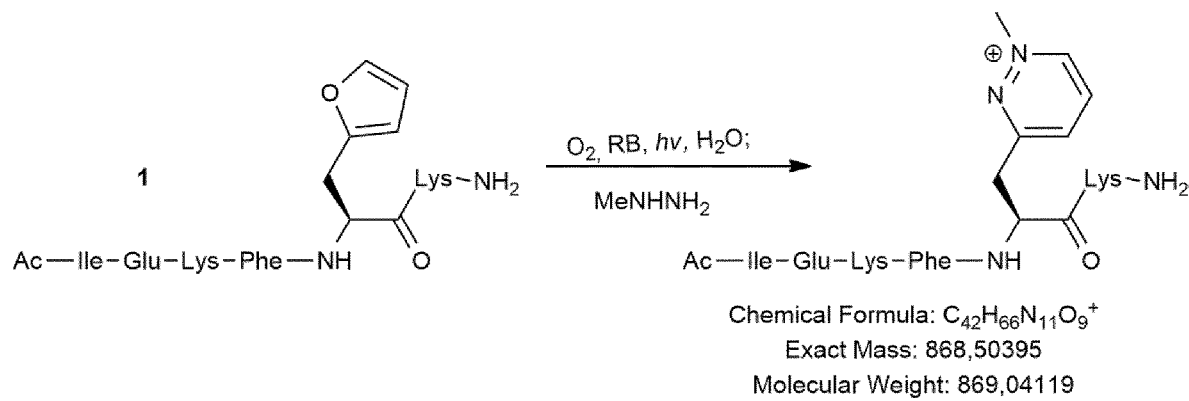
FIG. 23 represents a schematic overview illustrating the synthesis of the pyridazinium cation modified peptide 1 from furan-peptide 1 and methylhydrazine.
Figure 24:
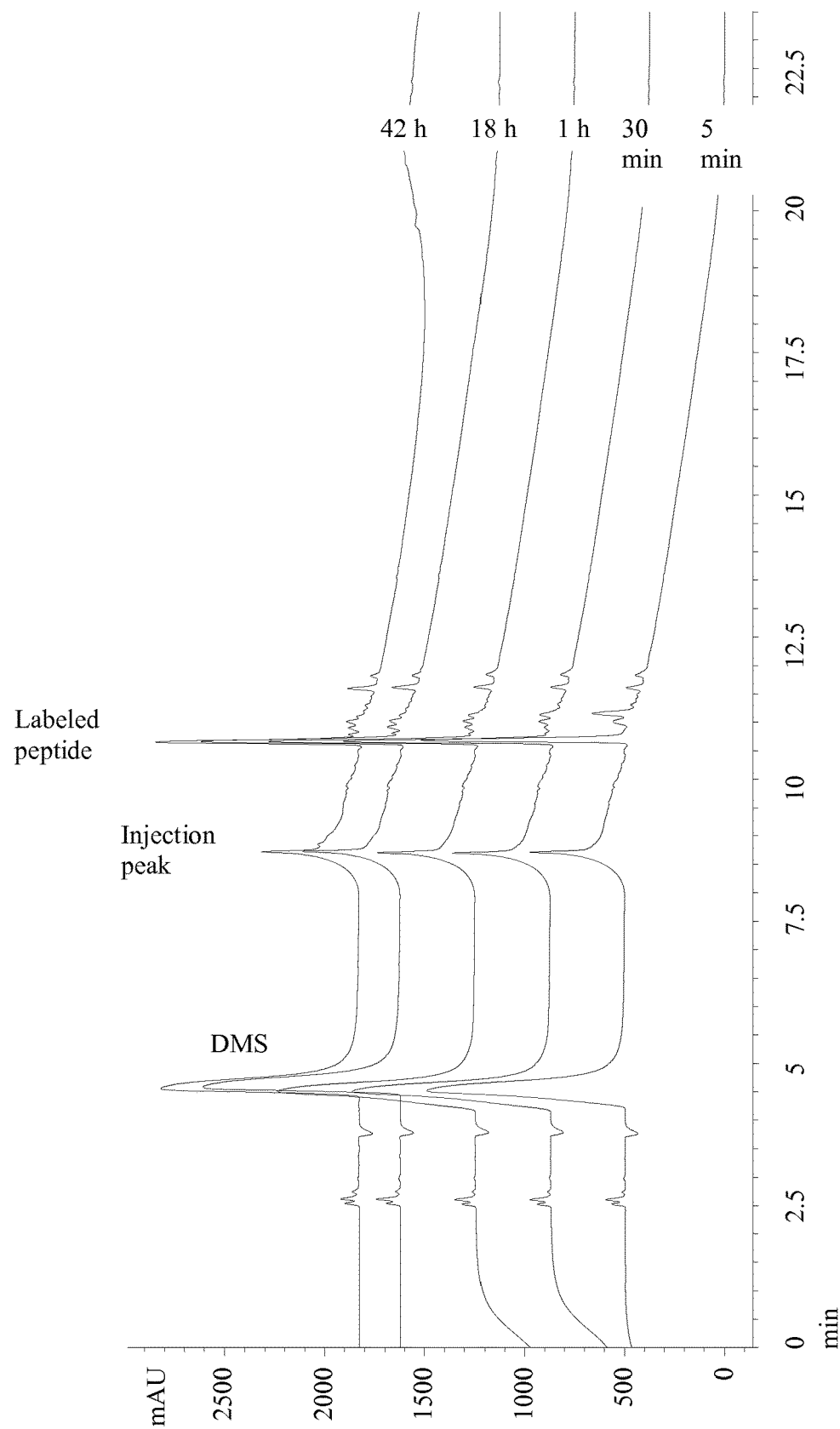
FIG. 24 represents the crude RP-HPLC chromatograms illustrating the stability of the pyridazinium cation modified peptide 1 over time; from top to bottom: Chromatogram after 42 hours reaction, Chromatogram after 18 hours reaction, Chromatogram after 1 hour reaction, Chromatogram after 30 min reaction, Chromatogram after 5 min reaction.

A second reaction was accomplished according to the general experimental set-up described above (Example 2), utilizing furan-peptide 1 (6 μmol, added from 20 mg/mL aqueous stock solution containing 10% DMSO) and methyl hydrazine (1 equiv., 6 μmol, from aqueous stock solution of 0.19 M) (FIG. 23). Photo-oxidation was carried out in 2.5 mL of MQ water, by irradiation with a xenon Variac Eimac Cermax 300 W lamp, followed by addition of the methyl-hydrazine and the reaction mixture was left stirring at room temperature. Reaction was followed by RP-HPLC (FIG. 24) and MALDI-TOF analysis (results not shown). In 30 min, the desired product was already formed (FIG. 24). Samples were taken at 5 min where the reaction was incomplete, and further completed at 30 min. Stability of the pyridazinium cation adduct was investigated. Reaction was monitored over time by HPLC. FIG. 24 illustrates the stability of the pyridazinium cation modified peptide 1 over time; from top to bottom: Chromatogram after 40 hours reaction, Chromatogram after 16 hours reaction, Chromatogram after 1 hour reaction, Chromatogram after 30 min reaction, Chromatogram after 5 min reaction. Product was formed from 5 minutes. Complete conversion and stability were confirmed after 30 min, 1 hour, 18 hours, and 42 hours (FIG. 24).

Figure 25:
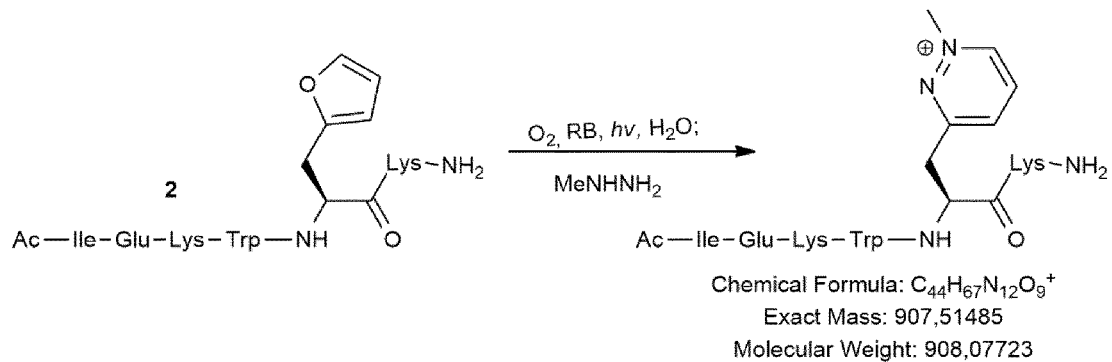
FIG. 25 represents a schematic overview illustrating the synthesis of the pyridazinium cation modified peptide 2 from furan-peptide 2 and methylhydrazine.

Example 10: Synthesis of a Pyridazinium Cation Modified Tryptophan-Containing Peptide The reaction was accomplished according to the general experimental set-up described above (Example 2), utilizing furan-peptide 2 (i.e., a tryptophan-containing peptide) (0.45 μmol, added from aqueous stock of 16.42 mM) and methyl hydrazine (10 equiv., 4.5 μmol, added from aqueous stock solution of 0.19 M) (FIG. 25). Photo-oxidation was carried out in 1.5 mL MQ water, for 50 min, followed by addition of methyl hydrazine, and the reaction mixture was left stirring at room temperature. Reaction was followed by RP-HPLC and MALDI-TOF analysis (results not shown). In 15 min, the desired product was already formed.

Figure 26:
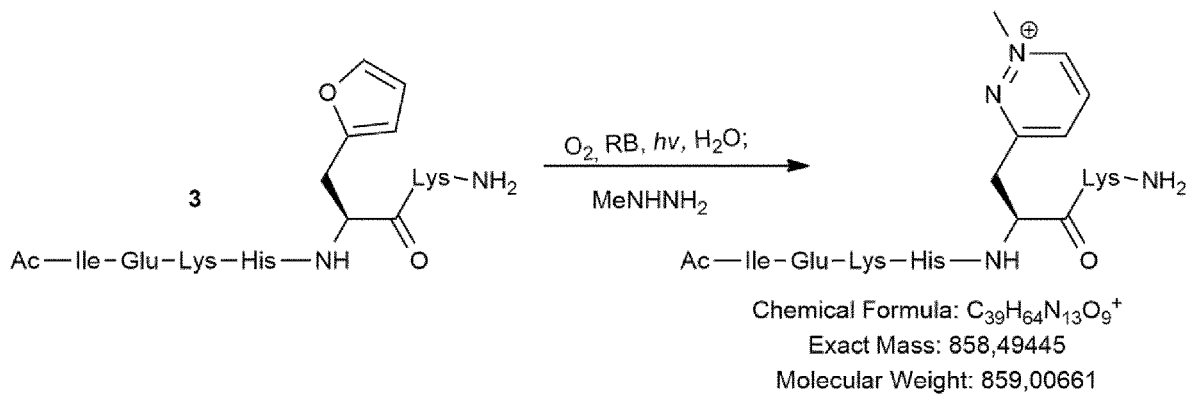
FIG. 26 represents a schematic overview illustrating the synthesis of the pyridazinium cation modified peptide 3 from furan-peptide 3 and methylhydrazine.

Example 11: Synthesis of a Pyridazinium Cation Modified Histidine-Containing Peptide The reaction was accomplished according to the general experimental set-up described above (Example 2), utilizing furan-peptide 3 (i.e., a histidine-containing peptide) (0.45 μmol, added from aqueous stock solution of 13.96 mM) and methyl hydrazine (10 equiv., 4.5 μmol, added from aqueous stock solution of 0.19 M) (FIG. 26). Photo-oxidation was carried out in 1.5 mL MQ water for 30 min, followed by addition of methylhydrazine, and the reaction mixture was left stirring at room temperature. Reaction was followed by RP-HPLC and MALDI-TOF analysis (results not shown). In 30 min the desired product was already formed.

Figure 27:
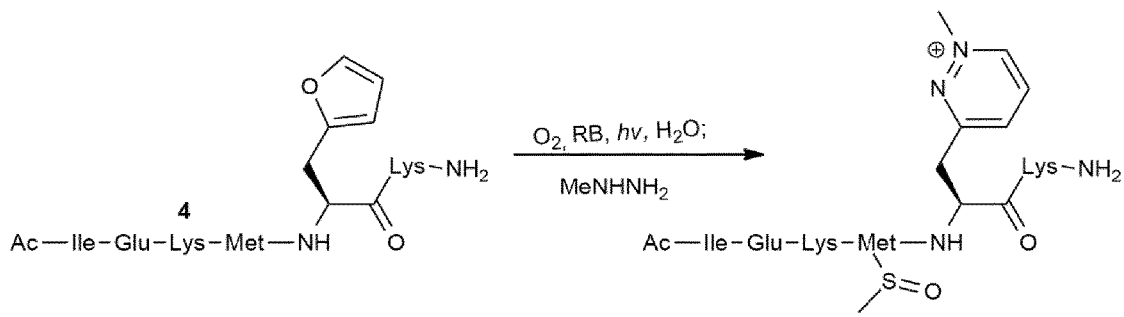
FIG. 27 represents a schematic overview illustrating the synthesis of the pyridazinium cation modified peptide 4 from furan-peptide 4 and methylhydrazine.

Example 12: Synthesis of a Pyridazinium Cation Modified Methionine-Containing Peptide The reaction was accomplished according to the general experimental set-up described above, utilizing furan-peptide 4 (i.e., a methionine-containing peptide) (0.36 μmol, added from aqueous stock solution of 9.7 mM concentration) and methylhydrazine (10 equiv, 3.6 μmol, added from aqueous stock solution of 0.19 M) (FIG. 27 and FIG. 42). Photo-oxidation proceeded in 1.2 mL aqueous solutions containing 10% phosphate buffered saline (PBS) followed by addition of methyl hydrazine, and the reaction mixture was left stirring at room temperature. Reaction was followed by RP-HPLC and MALDI-TOF analysis. In 15 min, the desired product was already formed. The pyridazinium peptide containing a methionine sulfoxide residue was formed as the major product accompanied with the non-oxidized methionine analog as minor product (results not shown).

FIG. 43 illustrates optimized conditions for the photo-oxidation of different peptides containing Trp (peptide 2), His (peptide 3), Met (peptide 4), or methionine sulfoxide (peptide 4a) residue.

Example 13: General Procedure for the Preparation of Pyridazine and Pyridazinium Adducts According to Embodiments of the Present Invention In order to investigate the site-specific peptide functionalization, the transformation of a furan-peptide to a pyridazine ring-containing peptide was investigated.

Furan containing compounds were dissolved in MilliQ water, containing catalytic amounts of rose Bengal, as photosensitizer (10 µM for 2, 3, 4 or $10^{-4}$ M for 1 and ethyl 3-(furan-2-yl)propionate). The solutions were cooled with an ice bath. Air was gently bubbled through the solution while it was irradiated with a Euromex 100 W cold light microscope lamp (or irradiation with a xenon Variac Eimac Cermax 300 W lamp when furan-peptide 1 and ethyl 3-(furan-2-yl)propionate were used). The reactions were monitored by RP-HPLC (or by TLC in case of ethyl 3-(furan-2-yl)propionate) and the products were analyzed by MALDI-TOF analysis and by NMR. After completion of the photo-oxidation reaction (usually 15 to 50 minutes), hydrazine or methyl hydrazine was added and the reaction was stirred for 15 min to 3 h. In case of the small pyridazinium adduct, the product was isolated after removal of water under reduced pressure.

Example 14: Example illustrating the synthesis of Ethyl 3-(1-(isonicotinamido)-5-oxo-4,5-dihydro-1H-pyrrol-2-yl)propanoate 9

An experiment was conducted using ethyl 3-(furan-2-yl) propionate as a furan substrate. The reaction was accomplished according to the general experimental set-up described above (Example 13).

Figure 29:
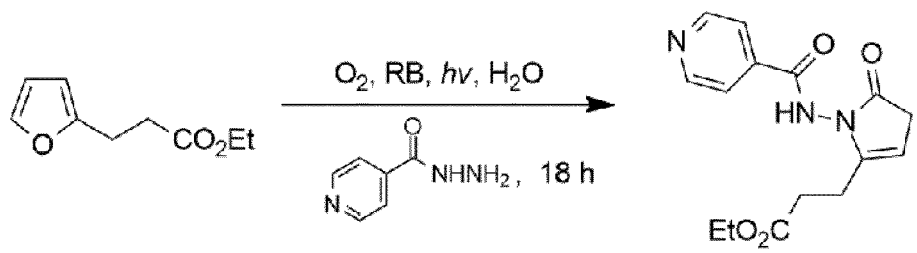
FIG. 29 represents a schematic overview illustrating the synthesis of the 2-pyrrolidinone adduct from the furan substrate (ethyl 3-(furan-2-yl)propionate) and isonicotinic hydrazide.
Figure 30:
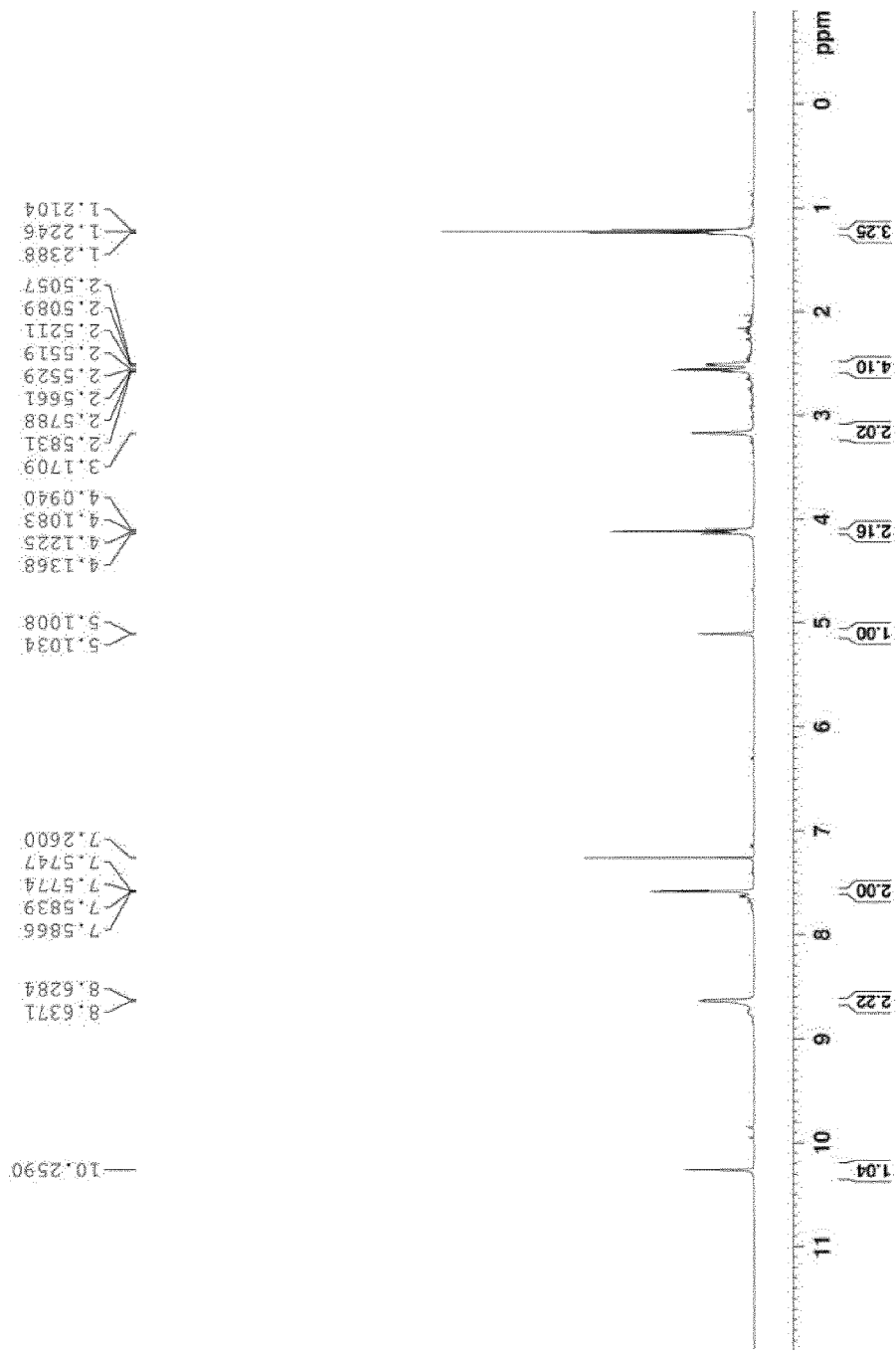
FIG. 30 represents a spectrum illustrating the $^1$H-NMR of the 2-pyrrolidinone adduct synthesized from ethyl 3-(furan-2-yl)propionate and isonicotinic hydrazide.
Figure 31:
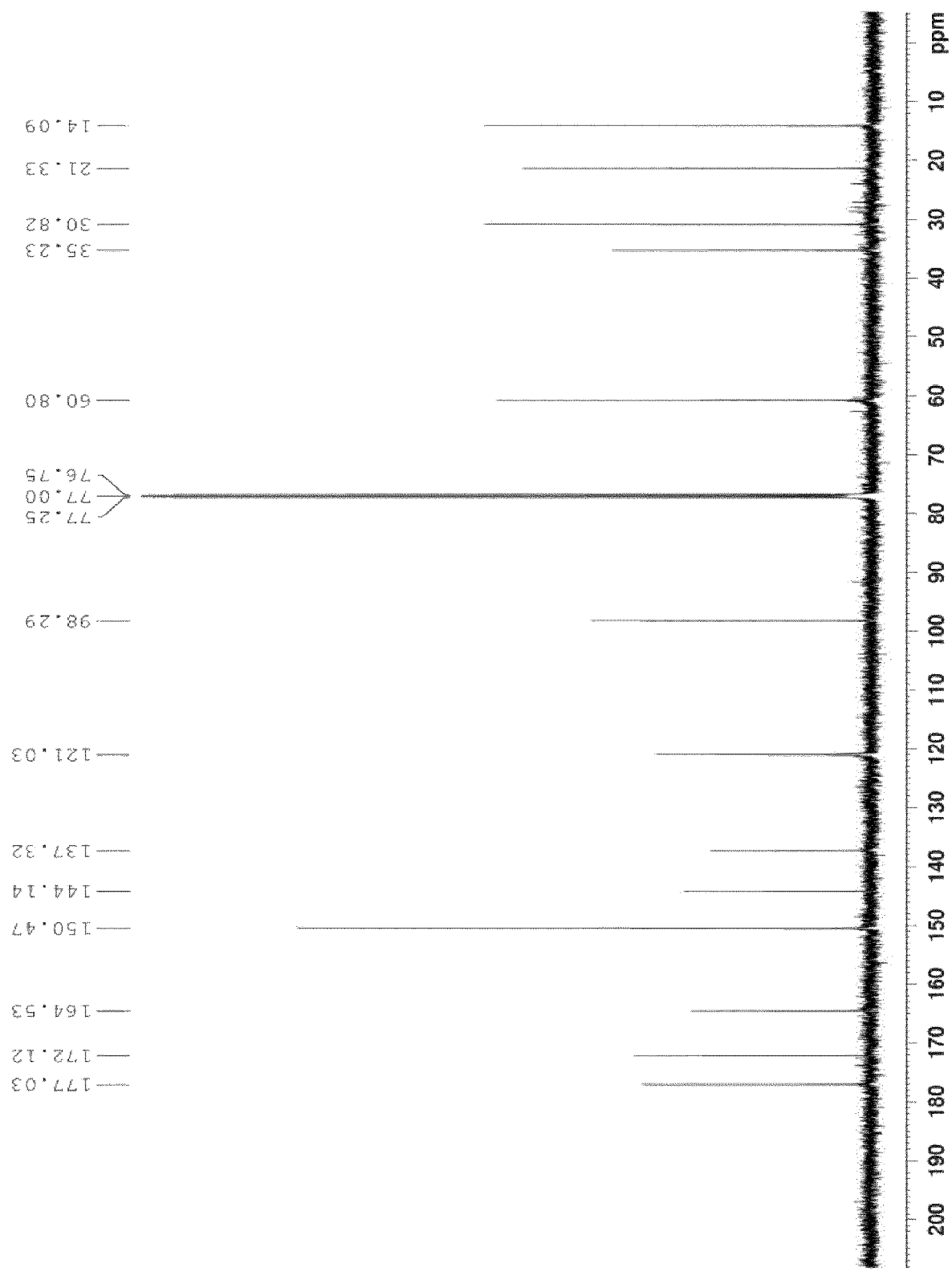
FIG. 31 represents a spectrum illustrating the $^{13}$C-NMR of the 2-pyrrolidinone adduct synthesized from ethyl 3-(furan-2-yl)propionate and isonicotinic hydrazide.

Ethyl 3-(furan-2-yl)propionate (0.5 mmol, 84 mg) was dissolved in water (10 mL) containing catalytic amounts of rose Bengal, as photosensitizer ($10^{-4}$ M). The solution was cooled with an ice bath. Oxygen was gently bubbled through the solution while it was irradiated with a xenon Variac Eimac Cermax 300 W lamp. The reaction was monitored by TLC. After completion of the reaction (30 min) isonicotinic hydrazide (0.5 mmol, 69 mg) was added and the reaction mixture was left stirring at room temperature for 18 h. After completion of the reaction, the mixture was extracted with EtOAc (2×10 mL). The combined organic phases were concentrated in vacuo and the product was purified by flash column chromatography (silica gel neutralized with Et$_3$N, petroleum ether/EtOAc, 1:2). Yield: 52% (79 mg). FIG. 29 illustrates the synthesis of a 2-pyrrolidinone adduct from ethyl 3-(furan-2-yl)propionate and isonicotinic hydrazide. $^1$H-NMR (FIG. 30) and $^{13}$C-NMR (FIG. 31) confirm the formation of the 2-pyrrolidinone adduct.

Example 15: Labeling of Furan-Peptide 1 with Lucifer Yellow CH (LYCH) Dilithium Salt According to an Embodiment of the Present Invention The coupling of a furan-peptide to a second agent comprising a hydrazide moiety was also performed in a one pot reaction using furan-peptide 1 and LYCH dilithium salt.

Figure 33:
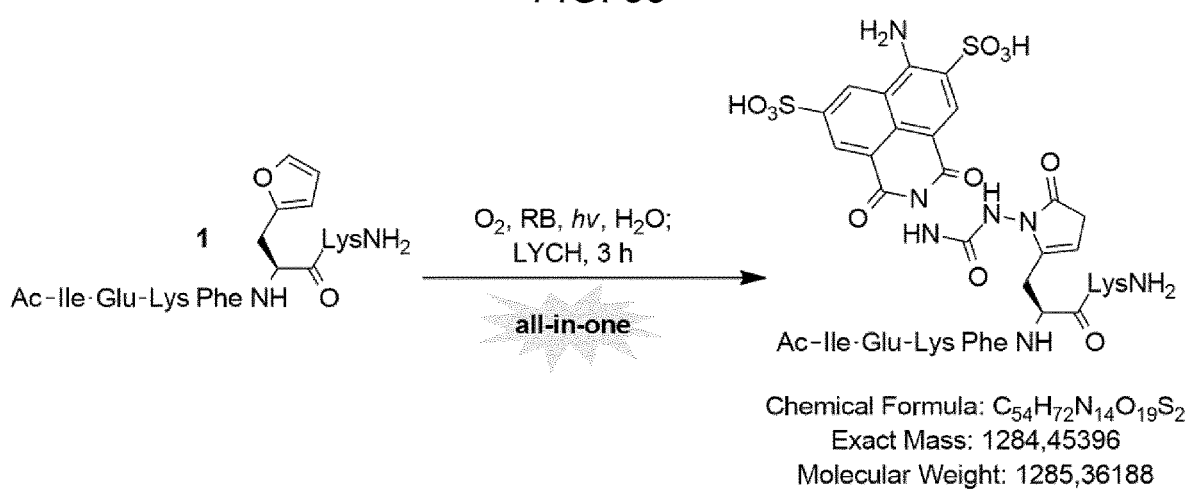
FIG. 33 represents a schematic overview illustrating the all-in-one coupling of furan-peptide 1 to Lucifer Yellow CH (LYCH) dilithium salt according to an embodiment of the present invention.

The one pot conversion of furan-peptide 1 could be achieved by photooxidation of furan-peptide 1 in the presence of 10 µM of rose Bengal (RB) and 1 equiv. of LYCH (FIG. 33).

A mixture of furan-peptide 1 (0.5 µmol, added from aqueous stock solution of 9.6 mM) with LYCH (0.5 µmol, added from aqueous stock solution of 15.7 mM) in MQ water (1.0 mL) containing 10 µM of Rose Bengal, was photooxidized for 15 min and left to stand at room temperature. The reaction was quasi completed after 3 h (results not shown). MALDI-TOF analysis confirmed the formation of the desired product (results not shown).

Example 16: Example Illustrating the Synthesis of 3-(3-Ethoxy-3-Oxopropyl)-1-Methylpyridazin-1-ium 4

An experiment was conducted using ethyl 3-(furan-2-yl) propionate as a furan substrate.

Figure 39:
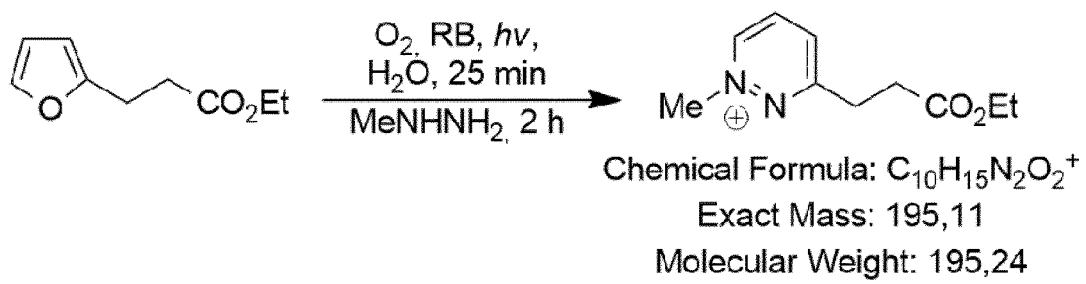
FIG. 39 represents a schematic overview illustrating the synthesis of the pyridazinium cation adduct from furan substrate (ethyl 3-(furan-2-yl)propionate) and methylhydrazine.
Figure 40:
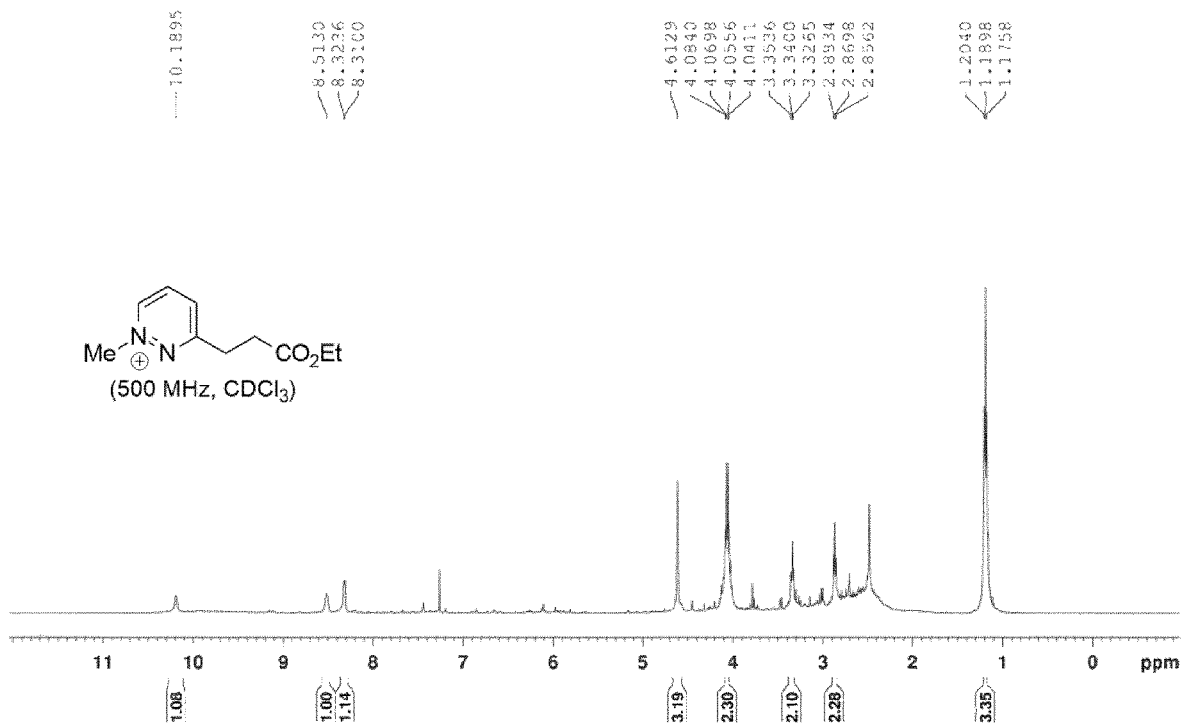
FIG. 40 represents a spectrum illustrating the $^1$H-NMR of the pyridazinium adduct synthesized from ethyl 3-(furan-2-yl)propionate and methylhydrazine.
Figure 41:
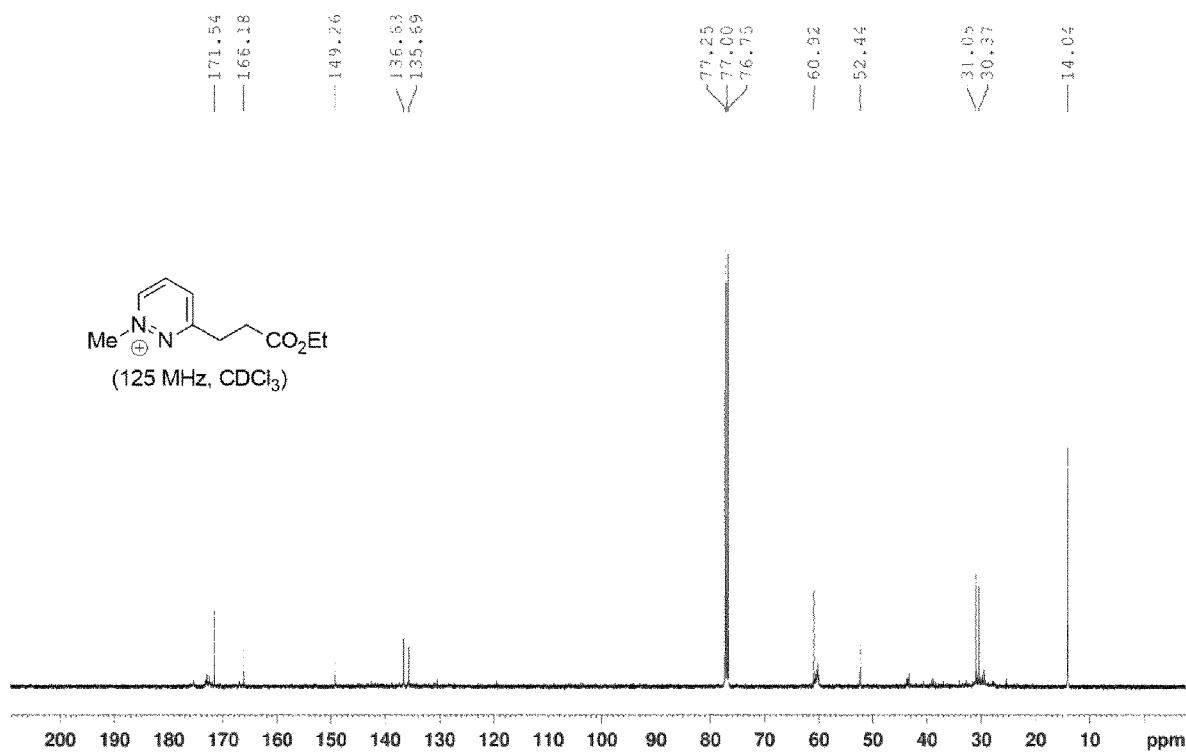
FIG. 41 represents a spectrum illustrating the $^{13}$C-NMR of the pyridazinium adduct synthesized from ethyl 3-(furan-2-yl)propionate and methylhydrazine.

The reaction was accomplished according to the general experimental procedure described above (Example 13), utilizing the model furan substrate (0.3 mmol, 50 mg) in water (8 mL), which was photooxidized for 25 min, by irradiation with a xenon Variac Eimac Cermax 300 W lamp, followed by the addition of methyl hydrazine (0.3 mmol, 16 µL) and stirring of the solution at room temperature for 2 h (FIG. 39). The reaction was monitored by TLC. The crude product was analyzed after removal of the solvent under reduced pressure (FIG. 40 and FIG. 41). FIGS. 40 and 41 confirm the formation of the desired product. $^1$H NMR (500 MHz, CDCl$_3$): δ=10.19 (brs, 1H), 8.51 (m, 2H), 8.32 (d, J=6.8 Hz, 2H), 4.61 (brs, 3H), 4.06 (q, J=7.1 Hz, 2H), 3.34 (t, J=6.8 Hz, 2H), 2.87 (t, J=6.8 Hz, 2H), 1.19 (t, J=7.1 Hz, 3H) ppm; $^{13}$C NMR (125 MHz, CDCl$_3$): δ=171.5, 166.2, 149.3, 136.6, 135.7, 60.9, 52.4, 31.1, 30.4, 14.0 ppm; HRMS (TOF ESI): calcd for C$_{10}$H$_{15}$N$_2$O$_2^+$: 195.1128 [M]$^+$; found:195.1126.

Example 17: Labeling of Furan-Peptide 1 with LYCH Dilithium Salt According to an Embodiment of the Present Invention In order to test whether a labeling agent with photosensitizer properties, such as LYCH, can be used as a photosensitizer in a method according to an embodiment of the present invention, the coupling of a furan-peptide to LYCH dilithium salt as a second agent comprising a hydrazide moiety was performed in a one pot reaction, without the addition of a sensitizer.

A mixture of furan-peptide 1 (0.6 µmol, added from aqueous stock solution of 9.6 mM) with LYCH (0.6 µmol, added from aqueous stock solution of 15.7 mM) in MQ water (1.0 mL) was photo-oxidised by irradiation with white light for 10 min, 20 min, and 60 min. The labeling reaction was followed by RP-HPLC which demonstrated the formation of the labeled peptide (results not shown). However, the observed reaction was not completed, possibly due to damage from prolonged irradiation or because LYCH was consumed acting as photosensitizer and labeling agent at the same time.

Example 18: Labeling of Furan-Containing Protein Human Carbonic Anhydrase with LYCH Dilithium Salt According to an Embodiment of the Present Invention In order to investigate labeling of a biologically functional protein, a furan-containing protein, namely human carbonic anhydrase (hCA), was prepared and subsequently labeled with LYCH dilithium salt with a method according to an embodiment of the present invention.

Pyrrolysine amber suppression protein expression technique was used to produce hCA protein with a site-selectively incorporated unnatural furan amino acid. Briefly, this approach is based on the natural system of pyrrolysine incorporation in methane producing archaea species and employs an aminoacyl-tRNA synthetase and a tRNA to incorporate an unnatural amino acid in response to an amber codon. Pyrrolysyl-tRNA synthetase PylSNorb, a synthetase designed for a norbornene amino acid was used (Kaya et al., 2012, Angew. Chem. Int. Ed., 51, 4466-4469).

The used furan amino acid was the furan modified amino acid (faa) as shown in FIG. 44. Mass spectroscopic (MS) analysis of hCA confirmed the presence of the faa on the correct position (amino acid position 36, starting from the methionine). Besides the furan amino acid also some other amino acids were found on position 36 (mainly glutamine). This was likely due to the fact that the synthetase was not entirely selective for the furan amino acid.

A 80 µL solution containing 5 µM of furan-containing hCA protein (11.7 µL of 34 µM stock solution) and 2 µM of rose Bengal (added from a 0.05 mM stock solution) was irradiated with white light for 5 and 10 minutes at 2° C. LYCH (1.0 equiv, from a 0.016 mM stock solution) was then added and the labeling reaction was followed by RP-HPLC. The mixture was left overnight to react.

For the RP-HPLC analysis, 4 µL of the reaction mixture was dissolved in 4 µL of MQ water. RP-HPLC analyses were performed on an Agilent 1100 Series instrument with a Phenomenex Jupiter C4 column (250×4.6 mm, 5 µm particle size at 35° C.). A flow rate of 1 ml/min was used with the following solvent systems: 0.1% TFA in H2O (A) and MeCN (B). The column was flushed for 3 min with 100% A, then a gradient from 0 to 100% B. The labeling reaction was followed by RP-HPLC which revealed the formation of a highly absorbing peak at 310 nm which was not present in the chromatogram of the oxidized protein (results not shown).

Example 19: Peptide-Peptide Stitching or Synthesis of Peptide-Peptide Conjugates According to an Embodiment of the Present Invention The general utility of the methodology of the present invention was also investigated for the coupling of a peptide containing an N-terminal, C-terminal, or internal furan moiety (referred to herein as "N-terminal furan-peptide", "C-terminal furan-peptide", and "internal furan-peptide" respectively) (FIG. 45) with a peptide containing an N-terminal or C-terminal hydrazine moiety (referred to herein as "N-terminal hydrazine peptide" and "C-terminal hydrazine peptide" respectively) or with peptides containing an N-terminal or C-terminal hydrazide moiety (referred to herein as "N-terminal hydrazide peptide" and "C-terminal hydrazide peptide" respectively).

Furthermore, C-terminal furan-peptides bearing a different amino acid (AA) next to the furan moiety (furylalanine) were tested (FIG. 45). In this way, C- to N-terminal, N- to N-terminal, internal to N-terminal as well as C- to C-terminal conjugations were achieved demonstrating the versatility of the present method.

C-terminal furan-peptides Ac-IEKFXaaFua-NH$_2$ with Xaa being Lys (SEQ ID NO. 6), Arg (SEQ ID NO. 7), Ala (SEQ ID NO. 8), Ser (SEQ ID NO. 9), Glu (SEQ ID NO. 10), Val (SEQ ID NO. 11), and Trp (SEQ ID NO. 12), and with Fua being furylalanine were synthesized according to the procedure as described in Example 1. Also, internal furan-peptide ABA-IEKFFuaG-NH$_2$ (SEQ ID NO. 13) with ABA being acetamidobenzoic acid and Fua being furylalanine, and N-terminal furan-peptide Ac-FualEKFK-NH$_2$ (SEQ ID NO. 14), with Fua being furylalanine, were synthesized according to the procedure as described in Example 1.

Protocol for the Preparation of an N-Terminal Hydrazine Peptide

N-terminal hydrazine peptides were synthesized by solid phase peptide synthesis as described herein (Material and methods, peptide syntheses) (FIG. 46). Subsequently, the N-terminus of the peptide was capped by tri-Boc hydrazinoacetic acid (3 equiv), using HATU as coupling reagent (3 equiv) and DIPEA (6 equiv) in DMF (1.5 mL). The mixture of tri-Boc hydrazinoacetic acid, HATU and DIPEA was added to the resin and shaken for 120 minutes. Afterwards, the solution was filtered off and the resin was washed with DMF/DCM/DMF (6×10 seconds each). Cleavage and deprotection were performed as described previously, and the N-terminal hydrazine peptides NH$_2$—NH—CH$_2$—C(O)-Gly-Arg-Gly-Asp-Ser-NH$_2$ (SEQ ID NO. 15) and NH$_2$—NH—CH$_2$—C(O)-Gly-Arg-Gly-Asp-Ser-Phe-NH$_2$ (SEQ ID NO. 16) were obtained (FIG. 46).

Protocol for the Preparation of C-Terminal Hydrazide Peptides

Preparation of 2-Cl-(Trt)-NHNH$_2$ Resin 50 mg of 2-Cl-(Trt)-NHNH$_2$ resin was washed with DMF/DCM/DMF (3×10 seconds each). Then, the resin was swollen in DMF/DCM (1:1) for 30 minutes and the solution was filtered off. The 2-Cl-(Trt)-NHNH$_2$ resin was freshly prepared for stability reasons. Then 2 mL of 5% (vol/vol) NH$_2$NH$_2$ was added to the resin for hydrazination (FIG. 47A). The mixture was agitated for 30 min in microwaves at 40° C. and then filtered off. The resin was washed three times with DMF/DCM/DMF and the hydrazination procedure was repeated. Then the mixture was filtered off, the resin was washed again and 2 mL of 5% (vol/vol) MeOH/DMF were added to the resin for 10 min. Then the resin was washed and drained. The resin was colored light green-yellow.

Coupling of 4-(Fmoc-amino)benzoic acid or 4-(Fmoc-aminomethyl) benzoic acid

After the hydrazination of the resin, 4-(Fmoc-amino) benzoic acid and the 4-(Fmoc-aminomethyl) benzoic acid were coupled to the resin for the synthesis of two different kind of hydrazide peptides (FIG. 47B). For the coupling of each reagent 3 equiv were used together with HATU (3 equiv) and DIPEA (6 equiv) in DMF (1.5 mL). The resin was shaken for 90 minutes. Then it was washed with DMF/DCM/DMC (6×10 seconds each). The peptide synthesis was further performed using automated peptide synthesizer. However, the next coupling on the amino benzoic residue was performed manually as the amine is aromatic.

Therefore, a mixture of Fmoc-Ser(tBu)-OH (10 equiv), HATU (10 equiv) and DIPEA (20 equiv) was added to the resin and the mixture was agitated in the microwaves for 1 h at 75° C. Then the mixture was filtered off, washed and the peptide synthesis was continued on the automated peptide synthesizer. Acetylation and cleavage were conducted as described herein and the C-terminal hydrazide peptides Ac-Gly-Arg-Gly-Asp-Ser-NH—$C_6H_4$—C(O)—NH—$NH_2$ (SEQ ID NO. 17) and Ac-Gly-Arg-Gly-Asp-Ser-NH—$CH_2$—$C_6H_4$—C(O)—NH—$NH_2$ (SEQ ID NO. 18) were obtained (FIG. 47B).

Protocol for the Preparation of N-Terminal Hydrazide Peptide

Figure 48:
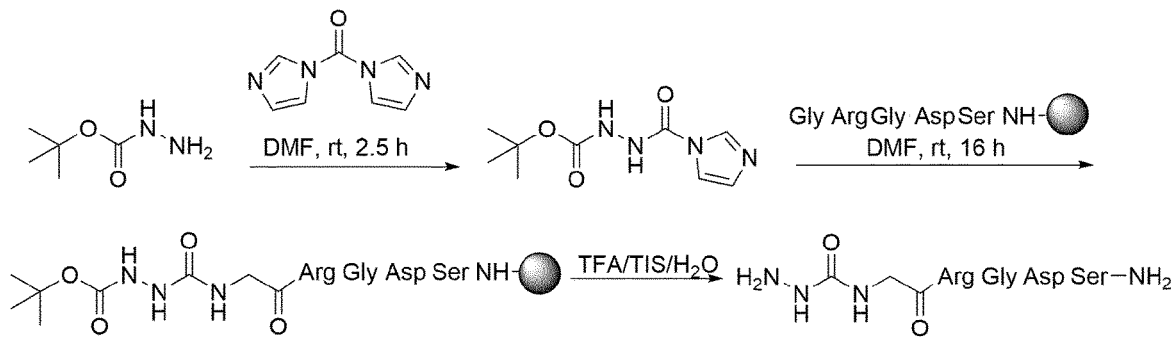
FIG. 48 represents a schematic overview illustrating the synthesis of an N-terminal hydrazide peptide to be used in a method according to an embodiment of the present invention.

To a suspension of 1,1'-Carbonyldiimidazole (210 μmol) in dry DMF (300 μL), tert-butyl carbazate (210 μmol) in dry DMF (200 μL) was added portionwise under $N_2$ for 2.5 h. Then the mixture was added to the peptide bound on resin (35 μmol) and the reaction was left for 16 hours at room temperature to ensure the coupling (FIG. 48). Resin was then filtered off, washed and cleaved as described herein, and the N-terminal hydrazide peptide $NH_2$—NH—C(O)—NH-Gly-Arg-Gly-Asp-Ser-$NH_2$ (SEQ ID NO. 19) (i.e., a semicarbazide) was obtained (FIG. 48).

Procedure for the Preparation of Peptide-Peptide Conjugates

Furan-containing peptides were dissolved in MilliQ water, containing catalytic amounts of rose Bengal, as photosensitizer (10 μM). The solutions were cooled with an ice bath. Air was gently bubbled through the solution while it was irradiated with a Euromex 100 W cold light microscope lamp. The reactions were monitored by RP-HPLC. After completion of the photo-oxidation reaction (usually 40 minutes), hydrazine or hydrazide-containing peptides were added and the reaction was shaken for 30 min to 18 h. The reactions were monitored by RP-HPLC and the products were analyzed by LC/MS and MALDI-TOF analysis.

Example 20: Pyridazinium-Based Conjugation of C-Terminal Furan-Peptides to an N-Terminal Hydrazine Peptide According to Embodiments of the Present Invention In order to investigate the influence of different chemical environments of the furan moiety on the coupling, the conjugation of different C-terminal furan-peptides containing each a different amino acid (Xaa) next to the furan moiety (furyl-alanine) with an N-terminal hydrazine peptide was performed (FIG. 49).

Figure 49:
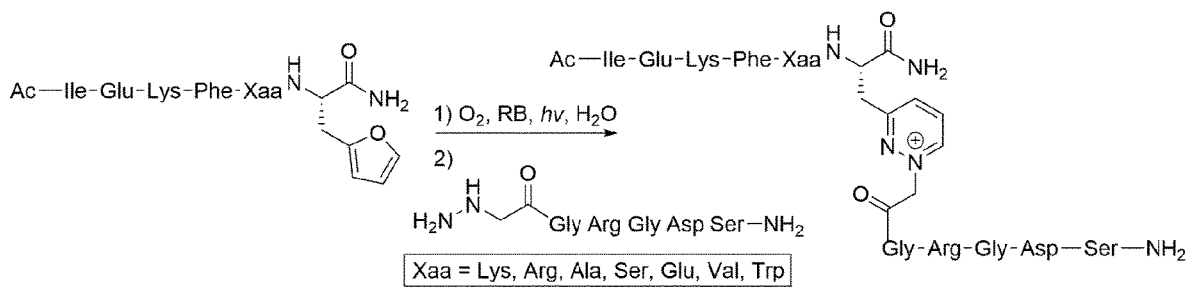
FIG. 49 represents a schematic overview illustrating a method according to an embodiment of the present invention for the pyridazinium-based conjugation of a C-terminal furan-peptide to an N-terminal hydrazine peptide.

The reaction was performed according to the general experimental procedure described above (Example 19), utilizing as C-terminal furan-peptides Ac-IEKFXaaFua-$NH_2$ with Xaa being Lys (SEQ ID NO. 6), Arg (SEQ ID NO. 7), Ala (SEQ ID NO. 8), Ser (SEQ ID NO. 9), Glu (SEQ ID NO. 10), Val (SEQ ID NO. 11), and Trp (SEQ ID NO. 12), and with Fua being furyl-alanine, and utilizing as N-terminal hydrazine peptide $NH_2$—NH—$CH_2$—C(O)-Gly-Arg-Gly-Asp-Ser-$NH_2$ (SEQ ID NO. 15) (FIG. 49). The C-terminal furan-peptides were synthesized according to the procedure as described in Example 1. The N-terminal hydrazine peptide was prepared as described in Example 19 (with reference to FIG. 46).

For Xaa being Lys (SEQ ID NO. 6), the reaction was accomplished according to the general experimental procedure described above, utilizing the AcIEKFKFua$NH_2$ peptide (0.6 μmol, added from aqueous stock solution of 17.2 mM) in MQ $H_2O$ (1.2 mL), which was photo-oxidised for 40 min followed by addition of the N-terminal hydrazine peptide (0.6 μmol, added from 100 mM phosphate buffer stock solution of 45.6 mM, pH 7). The reaction was monitored by RP-HPLC and in 30 min the desired conjugate was already formed as shown by a shift in the retention time of the conjugate as compared with the oxidized peptide (results not shown). The product was analyzed by MALDI-TOF analysis. MALDI-TOF spectrum of the collected peak at $t_R$=11.7 min demonstrated the formation of the desired conjugate along with a fragmentation product which seemed to be formed during the MALDI-TOF analysis (results not shown).

For Xaa being Arg (SEQ ID NO. 7), the reaction was accomplished according to the general experimental procedure described above, utilizing the AcIEKFRFua$NH_2$ peptide (0.6 μmol, added from aqueous stock solution of 25 mM) in MQ $H_2O$ (1.2 mL), which was photo-oxidised for 40 min followed by addition of the N-terminal hydrazine peptide (0.6 μmol, added from 100 mM phosphate buffer stock solution of 45.6 mM, pH 7). The reaction was monitored by RP-HPLC and the product was analyzed by MALDI-TOF analysis. In 30 min the desired conjugate was already formed as shown by a shift in the retention time of the conjugate as compared with the oxidized peptide (results not shown).

For Xaa being Ala (SEQ ID NO. 8), the reaction was accomplished according to the general experimental procedure described above, utilizing the AcIEKFAFua$NH_2$ peptide (0.6 μmol, added from aqueous stock solution of 22.4 mM, containing 2% DMSO) in MQ $H_2O$ (1.2 mL), which was photo-oxidised for 40 min followed by addition of the N-terminal hydrazine peptide (0.6 μmol, added from 100 mM phosphate buffer stock solution of 45.6 mM, pH 7). The reaction was monitored by RP-HPLC and the product was analyzed by MALDI-TOF analysis. In 30 min the desired conjugate was already formed as shown by a shift in the retention time of the conjugate as compared with the oxidized peptide (results not shown).

For Xaa being Trp (SEQ ID NO. 12), the reaction was accomplished according to the general experimental procedure described above, utilizing the AcIEKFWFua$NH_2$ peptide (0.6 μmol, added from aqueous stock solution of 17.8 mM, containing 10% DMSO) in MQ $H_2O$ (1.2 mL), which was photo-oxidised for 30 min followed by addition of the N-terminal hydrazine peptide (0.6 μmol, added from 100 mM phosphate buffer stock solution of 39.1 mM, pH 7). The reaction was monitored by RP-HPLC and the product was analyzed by MALDI-TOF analysis. In 30 min the desired conjugate was already formed as shown by a shift in the retention time of the conjugate as compared with the oxidized peptide (results not shown).

For Xaa, being Ser (SEQ ID NO. 9), the reaction was accomplished according to the general experimental procedure described above, utilizing the AcIEKFSFua$NH_2$ peptide (0.6 μmol, added from aqueous stock solution of 23.1 mM) in MQ $H_2O$ (1.2 mL), which was photo-oxidised for 40 min followed by addition of the N-terminal hydrazine peptide (0.6 μmol, added from 100 mM phosphate buffer stock solution of 39.1 mM, pH 7). The reaction was monitored by RP-HPLC and the product was analyzed by MALDI-TOF analysis. In 30 min, the desired conjugate was already formed as shown by a shift in the retention time of the conjugate as compared with the oxidized peptide (results not shown).

For Xaa being Glu (SEQ ID NO. 10), the reaction was accomplished according to the general experimental procedure described above, utilizing the AcIEKFEFua$NH_2$ peptide (0.6 μmol, added from aqueous stock solution of 14.6 mM, containing 9% DMSO) in MQ $H_2O$ (1.2 mL), which was photo-oxidised for 40 min followed by addition of the N-terminal hydrazine peptide (0.6 µmol, added from 100 mM phosphate buffer stock solution of 39.1 mM, pH 7). The reaction was monitored by RP-HPLC and the product was analyzed by MALDI-TOF analysis. In 30 min the desired conjugate was already formed as shown by a shift in the retention time of the conjugate as compared with the oxidized peptide (results not shown).

For Xaa being Val (SEQ ID NO. 11), the reaction was accomplished according to the general experimental procedure described above, utilizing the AclEKFVFuaNH$_2$ peptide (0.6 µmol, added from aqueous stock solution of 12.7 mM, containing 30% DMSO) in MQ H$_2$O (1.2 mL), which was photo-oxidised for 40 min followed by addition of the N-terminal hydrazine peptide (0.6 µmol, added from phosphate buffer stock solution of 39.1 mM, pH 7). The reaction was monitored by RP-HPLC and the product was analyzed by MALDI-TOF analysis. In 30 min the desired conjugate was already formed as shown by a shift in the retention time of the conjugate as compared with the oxidized peptide (results not shown).

Figure 50:
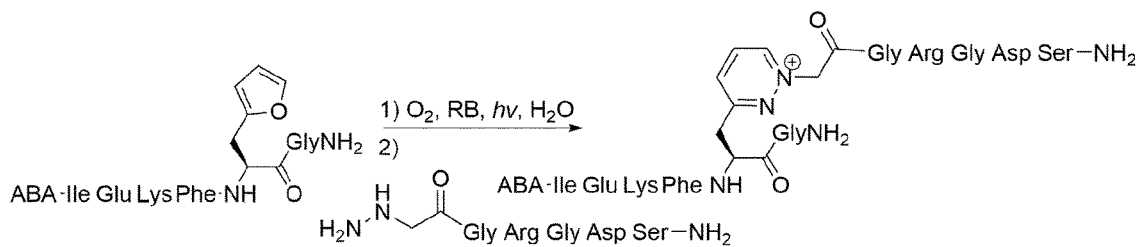
FIG. 50 represents a schematic overview illustrating a method according to an embodiment of the present invention for the pyridazinium-based conjugation of an internal furan-peptide to an N-terminal hydrazine peptide.

Example 21: Pyridazinium-Based Conjugation of an Internal Furan-Peptide to an N-Terminal Hydrazine Peptide According to an Embodiment of the Present Invention The reaction was accomplished according to the general experimental procedure described above (Example 19), utilizing the internal furan-peptide ABA-IEKFFuaGNH$_2$ (SEQ ID NO. 13) (0.6 µmol, added from aqueous stock solution of 59.6 mM, containing 20% DMSO) in MQ H$_2$O (1.2 mL), which was photo-oxidised for 40 min followed by addition of the N-terminal hydrazine peptide NH$_2$—NH—CH$_2$—C(O)-Gly-Arg-Gly-Asp-Ser-NH$_2$ (SEQ ID NO. 15) (0.6 µmol, added from 100 mM phosphate buffer stock solution of 39.1 mM, pH 7) (FIG. 50). The internal furan-peptide was synthesized according to the procedure as described in Example 1. The N-terminal hydrazine peptide was prepared as described in Example 19 (with reference to FIG. 46). The reaction was monitored by RP-HPLC and the product was analyzed by MALDI-TOF analysis. In 30 min the desired conjugate was already formed together with a small amount of side products (results not shown).

Figure 51:
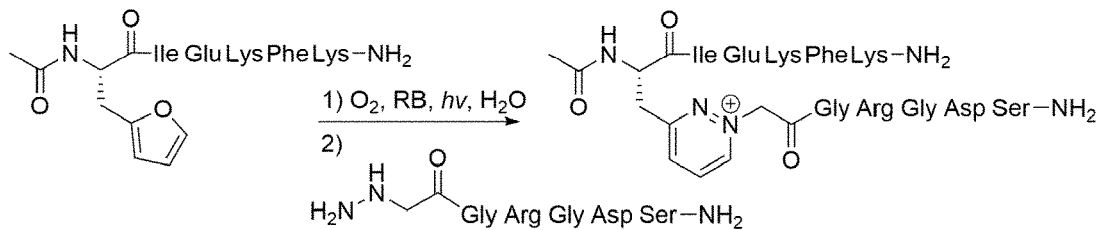
FIG. 51 represents a schematic overview illustrating a method according to an embodiment of the present invention for the pyridazinium-based conjugation of an N-terminal furan-peptide to an N-terminal hydrazine peptide.

Example 22: Pyridazinium-Based Conjugation of an N-Terminal Furan-Peptide to an N-Terminal Hydrazine Peptide According to an Embodiment of the Present Invention The reaction was accomplished according to the general experimental procedure described above (Example 19), utilizing the N-terminal furan-peptide AcFualEKFKNH$_2$ (SEQ ID NO. 14) (0.6 µmol, added from aqueous stock solution 21.2 mM, containing 20% DMSO) in MQ H$_2$O (1.2 mL), which was photo-oxidised for 40 min followed by addition of the N-terminal hydrazine peptide NH$_2$—NH—CH$_2$—C(O)-Gly-Arg-Gly-Asp-Ser-NH$_2$ (SEQ ID NO. 15) (0.6 µmol, added from 100 mM phosphate buffer stock solution of 28 mM, pH 7) (FIG. 51). The N-terminal furan-peptide was synthesized according to the procedure as described in Example 1. The N-terminal hydrazine peptide was prepared as described in Example 19 (with reference to FIG. 46). The reaction was monitored by RP-HPLC and the product was analyzed by MALDI-TOF analysis. In 30 min the desired conjugate was already formed together with a small amount of side products (results not shown).

Figure 52:
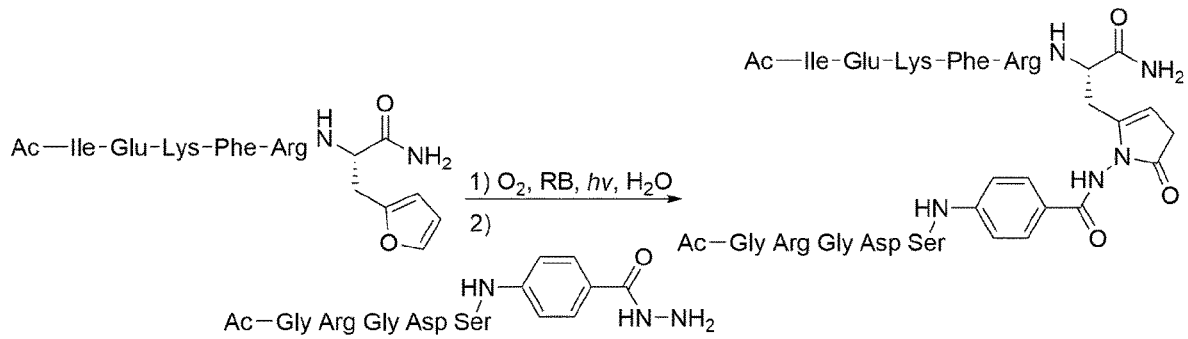
FIG. 52 represents a schematic overview illustrating a method according to an embodiment of the present invention for the pyrrolidinone-based conjugation of a C-terminal furan-peptide to a C-terminal 4-aminobenzoic hydrazide peptide.

Example 23: Pyrrolidinone-Based Conjugation of a C-Terminal Furan-Peptide to a C-Terminal 4-Aminobenzoic Hydrazide Peptide According to an Embodiment of the Present Invention The reaction was accomplished according to the general experimental procedure described above (Example 19), utilizing the C-terminal furan-peptide AclEKFRFuaNH$_2$ peptide (SEQ ID NO. 7) (0.6 µmol, added from aqueous stock solution 25 mM) in MQ H$_2$O (1.2 mL), which was photo-oxidised for 40 min followed by addition of a C-terminal 4-aminobenzoic hydrazide peptide Ac-Gly-Arg-Gly-Asp-Ser-NH—C$_6$H$_4$—C(O)—NH—NH$_2$ (SEQ ID NO. 17) (0.6 µmol, added from aqueous stock solution of 10 mM, pH was adjusted to 5.4) (FIG. 52). The C-terminal furan-peptide was synthesized according to the procedure as described in Example 1. The C-terminal 4-aminobenzoic hydrazide peptide was prepared as described in Example 19 (with reference to FIG. 47A and upper panel of FIG. 47B). The reaction was monitored by RP-HPLC and was almost completed in 18 h (results not shown). MALDI-TOF spectrum of the crude reaction mixture (18 h), demonstrated the formation of the conjugated product (results not shown).

Figure 53:
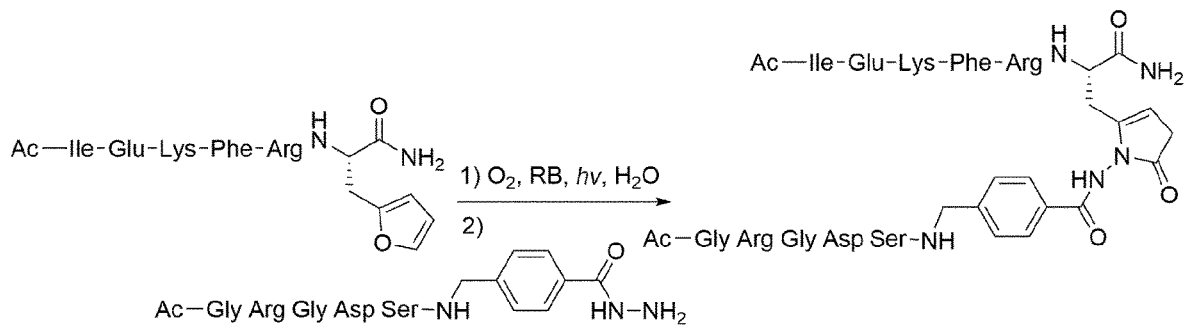
FIG. 53 represents a schematic overview illustrating a method according to an embodiment of the present invention for the pyrrolidinone-based conjugation of a C-terminal furan-peptide to a C-terminal 4-aminomethyl benzoic hydrazide peptide.

Example 24: Pyrrolidinone-Based Conjugation of a C-Terminal Furan-Peptide to a C-Terminal 4-Aminomethyl Benzoic Hydrazide Peptide According to an Embodiment of the Present Invention The reaction was accomplished according to the general experimental procedure described above (Example 19), utilizing the C-terminal furan-peptide AclEKFRFuaNH$_2$ (SEQ ID NO. 7) (0.6 µmol, added from aqueous stock solution 25 mM) in MQ H$_2$O (1.2 mL), which was photo-oxidised for 40 min followed by addition of a C-terminal 4-aminomethyl benzoic (acid) hydrazide peptide Ac-Gly-Arg-Gly-Asp-Ser-NH—CH$_2$—C$_6$H$_4$—C(O)—NH—NH$_2$ (SEQ ID NO. 18) (0.6 µmol, added from aqueous stock solution of 19.6 mM, pH 3.6) (FIG. 53). The C-terminal furan-peptide was synthesized according to the procedure as described in Example 1. The C-terminal 4-aminomethyl benzoic hydrazide peptide was prepared as described in Example 19 (with reference to FIG. 47A and lower panel of FIG. 47B). The reaction was monitored by RP-HPLC and was almost completed in 18 h (results not shown). The MALDI-TOF spectrum of the collected peak at $t_R$=12.1 min demonstrated the formation of the desired conjugate (results not shown).

Figure 54:
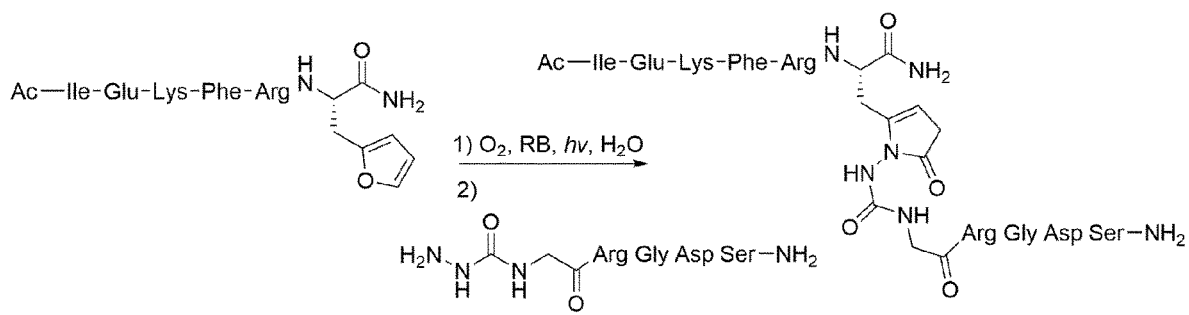
FIG. 54 represents a schematic overview illustrating a method according to an embodiment of the present invention for the pyrrolidinone-based conjugation of a C-terminal furan-peptide to an N-terminal semicarbazide peptide.

Example 25: Pyrrolidinone-Based Conjugation of a C-Terminal Furan-Peptide to a N-Terminal Semicarbazide Peptide According to an Embodiment of the Invention The reaction was accomplished according to the general experimental procedure described above (Example 19), utilizing the C-terminal furan-peptide AclEKFRFuaNH$_2$ (SEQ ID NO. 7) (0.6 µmol, added from aqueous stock solution 25 mM) in MQ H$_2$O (1.2 mL), which was photo-oxidised for 40 min followed by addition of an N-terminal semicarbazide peptide NH$_2$—NH—C(O)—NH—CH$_2$—C(O)-Arg-Gly-Asp-Ser-NH$_2$ (SEQ ID NO. 19) (0.6 µmol, added from stock solution of 41.8 mM, adjusted pH 4) (FIG. 54). The C-terminal furan-peptide was synthesized according to the procedure as described in Example 1. The N-terminal semicarbazide peptide was prepared as described in Example 19 (with reference to FIG. 48). The reaction was monitored by RP-HPLC and was almost completed in 18 h (results not shown). MALDI-TOF spectrum of the collected peak at $t_R$=12.2 min (18 hours) demonstrated the formation of the desired conjugate (results not shown).

Figure 55:
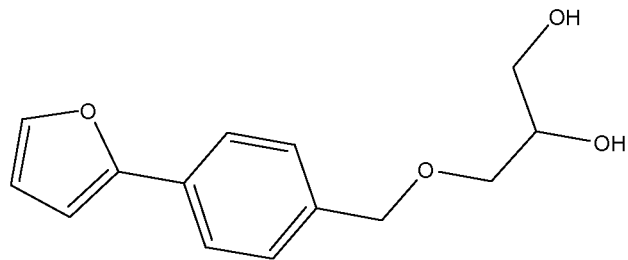
FIG. 55 represents the sequence of furan-modified oligonucleotides ODN1a and ODN1b and the furan building block of Formula (1) to be used in methods according to embodiments of the present invention.

Example 26: Synthesis of a Pyridazinium-Modified Oligonucleotide According to an Embodiment of the Present Invention Synthesis of furan-modified oligonucleotides The following furan-modified oligonucleotides (referred to herein as "furan-oligonucleotides") were synthesized (FIG. 55):

```
ODN1a:
                                 (SEQ ID NO. 20)
5'-d(CTG ACG C1C TGC)-3'
and ODN1b:
                                 (SEQ ID NO. 21)
5'-d(CTG ACG G1G TGC)-3'.
```

Furan building block 1 (FIG. 55) was synthesized according to Op De Beeck and Madder, 2012, JACS, 134, 10737-10740.

The furan-oligonucleotides were synthesized on the ABI 394 DNA synthesizer (Applied Biosystems, CA, USA) with the DMT-on method and purified with Sep-Pak cartridge (Waters NV/SA, Zellik, Belgium). The nucleosides where purchased from Glen Research, the other reagents from Proligo.

The 3' end of the ODN was attached to the solid phase and the synthesis was done in the 3' to 5' direction. The coupling of the furan modified building block was performed manually. Before synthesis, the furan-modified building block was dissolved in dry acetonitrile to a concentration of 0.06 M. The automated synthesis was interrupted at the moment the furan-modified building block needed to be incorporated. First 0.5 mL of phosphoramidite and 0.5 mL of dicyano imidazole-activator were repeatedly brought on the column. Subsequently, the column was rinsed with 1 mL acetonitrile, followed by a manual capping procedure. Here, the ODN was capped by adding a 1:1 mixture of CAP A (THF: 2,6-lutidine: acetic acid, 8:1:1) and CAP B (10% of 1-methylimidazole in THF) and afterwards rinsed again with acetonitrile. Thereafter, the automated synthesis was resumed. The synthesis was performed with DMT-on modus implying that the 5'-end remains DMT-protected after synthesis, allowing for Sep-Pak purification. Cleavage and deprotection was performed overnight by adding ammonium hydroxide (1 mL, 28%) and stirring at 55° C. Finally, Sep-Pak purification was performed by consecutively applying acetonitrile (10 mL) and TEAA (5 mM, 10 mL) on the cartridge. Subsequently, the synthesized ODN was injected into the column, and consecutively ammonium hydroxide (2.8%; 15 ml) and milliQ water (10 ml) were applied to rinse off side products. Then, TFA (1.5 M; 10 ml) was used on the column for deprotection and DMT cations were formed resulting in an orange colour. MilliQ water (10 ml), acetonitrile/water (1:4.5 ml) were applied to rinse of the synthesized ODN of the column.

Analysis of Synthesized Furan-Oligonucleotides

The purity of the furan-oligonucleotides was assessed and confirmed by HPLC-chromatography. The mass of the Sep-Pak purified oligonucleotide (ODN) was determined with MALDI-TOF. 1 µL of sample was mixed with 2 µL matrix containing 3-hydroxypicoline acid (50 mg in 200 µL milliQ and 250 µL MeCN) and ammonium citrate (35 mg in 500 µL milliQ) in a 9:1 ration (HPA:AC). Then Dowex beads were added to desalt the sample. Finally 1 µL of sample was spotted on the MALDI plate and measured after crystallization. For the determination of the concentration of the ODN Trinean dropsense was used. This equipment is based on UV-spectrometry. The sample was measured at 260 nm at room temperature.

Figure 56:
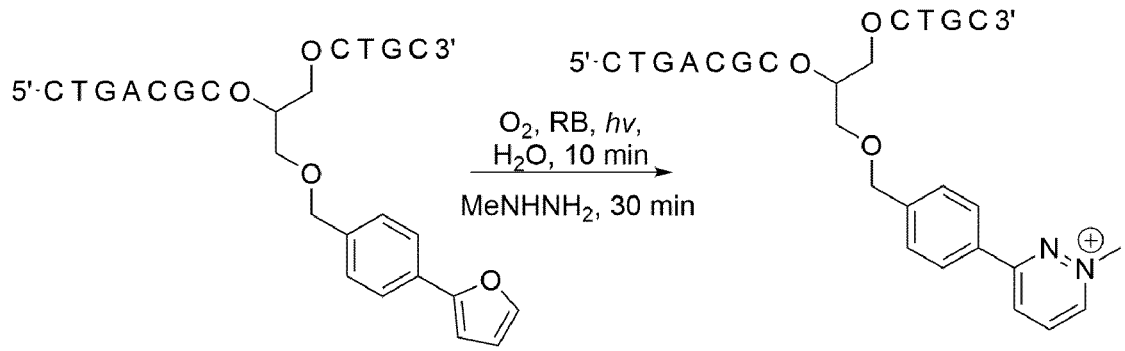
FIG. 56 represents a schematic overview illustrating the synthesis of a pyridazinium-modified oligonucleotide according to an embodiment of the present invention.

Synthesis of a Pyridazinium Cation Modified Oligonucleotide According to an Embodiment of the Present Invention The modified ODN1a (40 µM) and rose bengal (1 µM) were dissolved in milliQ (50 µL). The mixture was irradiated by green light for 10 minutes and stirred with a thermoshaker at 950 rpm at 20° C. After irradiation, 8 equivalents of methylhydrazine were added to the solution and then it was incubated in the thermoshaker for 30 min at 950 rpm and 20° C. (FIG. 56). After each step a sample was taken for HPLC analysis (4 µL sample and 16 µL milliQ). A linear gradient was used: 0%-20% MeCN in 30 min, 20%-100% MeCN in 6 min. The measurements were performed at a temperature of 50° C. The chromatograms were analyzed at a wavelength of 260 nm and 470 nm. Transformation into the labeled oligonucleotide was observed by the appearance in the chromatogram of a peak corresponding to the desired conjugate (results not shown).

Figure 57:
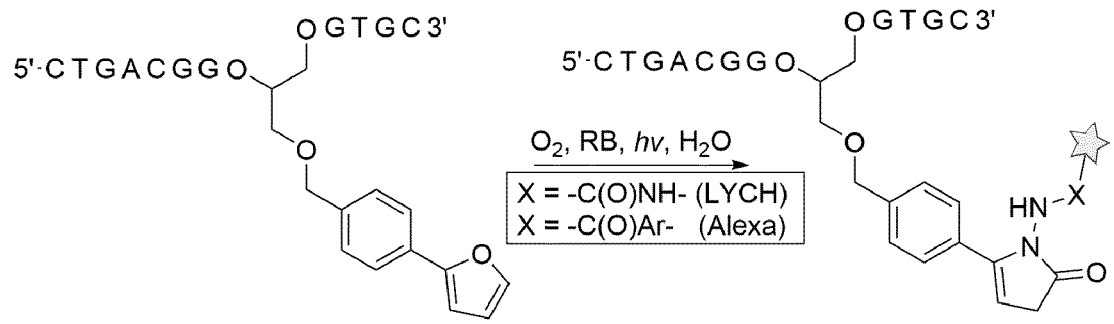
FIG. 57 represents a schematic overview illustrating the labeling of a furan-oligonucleotide with Lucifer Yellow CH dilithium salt (LYCH) or with Alexa Fluor 488 hydrazide (Alexa) according to an embodiment of the present invention.

Example 27: Labeling of Furan-Oligonucleotide with Lucifer Yellow CH (LYCH) Dilithium Salt According to an Embodiment of the Present Invention The modified ODN1b (40 µM) and rose bengal (1 µM) were dissolved in milliQ (25 µL). The mixture was irradiated by green light for 10 minutes and stirred with a thermoshaker at 950 rpm and 20° C. Then 10 equivalents of Lucifer Yellow CH were added and the reaction was incubated for 30 minutes (FIG. 57). Reaction was followed by RP-HPLC.

The formation of the desired peak was confirmed by MALDI-TOF (result not shown).

Example 28: Labeling of Furan-Oligonucleotide with Alexa Fluor 488 Hydrazide According to an Embodiment of the Present Invention A 25 µL solution containing 40 µM solution of the oligonucleotide ODN1b, 1 µM rose bengal solution and 5 equivalents of Alexa Fluor 488 Hydrazide was irradiated for 10 minutes with green light (FIG. 57), after which the starting oligonucleotide was almost fully converted to the oxidized species and the labeled oligonucleotide (results not shown). Further conversion to the desired labeled oligonucleotide was observed after 30 min of incubation. Reaction was followed by RP-HPLC and MALDI-TOF confirmed the formation of the expected product (results not shown).

Figure 58:
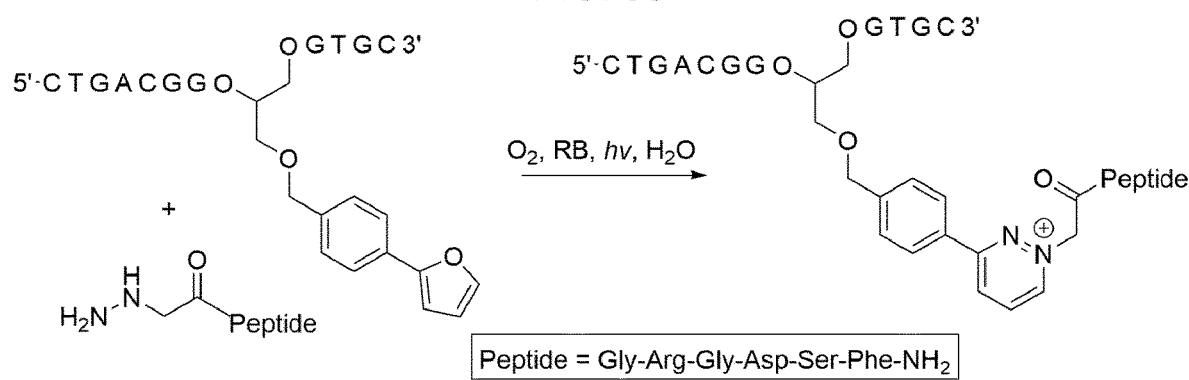
FIG. 58 represents a schematic overview illustrating the synthesis of a peptide-oligonucleotide conjugate according to an embodiment of the present invention.

Example 29: Preparation of a Peptide-Oligonucleotide Conjugate According to an Embodiment of the Present Invention A solution of ODN1b furan-oligonucleotide (5 nmol) and N-terminal hydrazine peptide $NH_2$—NH—$CH_2$—C(O)-Gly-Arg-Gly-Asp-Ser-Phe-$NH_2$ (SEQ ID NO. 16) (25 nmol, added from 100 mM phosphate buffer stock solution of 7.3 mM, pH 7) in MQ H$_2$O (150 μL) was irradiated with green light in presence of rose Bengal (2 μM) (FIG. 58). The ODN1b oligonucleotide was synthesized according to the procedure as described in Example 26. The N-terminal hydrazine peptide was prepared as described in Example 19 (with reference to FIG. 46). Reaction was followed by HPLC. Irradiation for 10 min already yielded the desired conjugate with almost full conversion of the starting furan-oligonucleotide and then the reaction was left to react for 1 h. MALDI analysis confirmed the formation of the desired conjugate (results not shown).

The invention claimed is:

1. A method for site-selective coupling of a first agent to a second agent, comprising the steps of:
contacting a first agent comprising at least one furan moiety with an activation signal and with a second agent comprising at least one hydrazine moiety or at least one hydroxylamine moiety, thereby activating said furan moiety to an activated furan moiety; and
reacting said activated furan moiety with the hydrazine moiety or the hydroxylamine moiety, thereby site-selectively coupling said first agent to said second agent;
wherein the first agent is a peptide, a small molecule or a polynucleotide;
wherein the second agent is a labeling reagent, a small molecule, a solid surface, a biomolecule, or a polymer;
wherein the activation signal is a reactive oxygen species; and
wherein the furan moiety is converted to a pyridazinium cation or to a dihydropyrrol-2-one moiety.

2. The method according to claim 1, comprising the steps of:
a) providing a first agent comprising at least one furan moiety;
b) contacting said first agent with the activation signal, thereby activating said furan moiety to the activated furan moiety;
c) contacting said activated furan moiety with a second agent comprising at least one hydrazine moiety or at least one hydroxylamine moiety; and
d) reacting said activated furan moiety with the hydrazine moiety or the hydroxylamine moiety, thereby site-selectively coupling said first agent to said second agent.

3. The method according to claim 1, comprising the steps of:
a) providing a first agent comprising at least one furan moiety;
b') contacting the first agent with a second agent comprising at least one hydrazine moiety or at least one hydroxylamine moiety, thereby obtaining a mixture of the first agent and the second agent;
c') contacting the mixture of the first agent and the second agent with the activation signal, thereby activating said furan moiety to the activated furan moiety; and
d) reacting the activated furan moiety with the hydrazine moiety or the hydroxylamine moiety, thereby site-selectively coupling the first agent to the second agent.

4. The method according to claim 1, wherein the first agent is contacted with the activation signal immediately after contacting the first agent with the second agent.

5. The method according to claim 1, wherein the second agent comprises a hydrazine moiety or hydroxylamine moiety having a structure of Formula I, wherein $X^1$ is O, S, or NH, $L^1$ is N or O, and, if $L^1$ is N, $R^1$ is hydrogen, $C_{1-30}$alkyl, or $C_{6-20}$aryl, and if $L^1$ is O, $R^1$ is absent, and wherein Formula I is

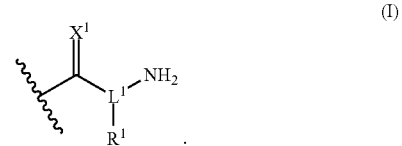

6. The method according to claim 1, wherein the second agent comprises a hydrazine moiety or hydroxylamine moiety having a structure of Formula Ia, wherein EDG is an electron donating group, wherein $X^1$ is O, S, or NH, $L^1$ is N or O, and, if $L^1$ is N, $R^1$ is hydrogen, $C_{1-30}$alkyl, or $C_{6-20}$aryl, and if $L^1$ is O, $R^1$ is absent, and wherein Formula Ia is

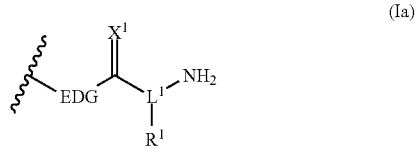

and wherein the EDG is selected from the group consisting of —NH—; —O—; —S—; $C_{1-30}$alkyl; $C_{6-20}$aryl; and $C_{5-20}$heteroaryl; wherein the $C_{1-30}$alkyl; $C_{6-20}$aryl; or $C_{5-20}$heteroaryl group is optionally substituted with an $C_{1-6}$alkyl, $C_{3-6}$cycloalkyl, carboxyl, or $C_{1-6}$alkoxy.

7. The method according to claim 1, wherein the second agent comprises a hydrazine moiety selected from the group consisting of a hydrazide, a carbohydrazide, a semicarbazide, a thiosemicarbazide, an iminosemicarbazide, a guanyl hydrazine, a dansyl hydrazine, a hydrazine, and a methyl hydrazine.

8. The method according to claim 1, wherein the biomolecule is a peptide, a polysaccharide, a lipid, a nucleic acid, or a combination thereof.

9. The method according to claim 1, wherein the activation signal is singlet oxygen.

10. The method according to claim 9, wherein the singlet oxygen is generated by irradiation of air or oxygen in the presence of a sensitizer.

11. The method according to claim 10, wherein the irradiation is polychromatic light, Xenon light, or monochromatic light.

12. The method according to claim 10, wherein the sensitizer is selected from the group consisting of xanthene, xanthene derivatives, fluorescein, fluorescein derivatives, methylene blue, porphyrine, porphyrine derivatives, phtalocyanine, phtalocyanine derivatives, naphthalocyanines, bacteriochlorins, texaphyrins, cholorophyll, and *spirulina*.

13. The method according to claim 9, wherein the singlet oxygen is generated by irradiation of air or oxygen by polychromatic light in the presence of Rose bengal.

14. The method according to claim 1, wherein the activation signal is a reactive oxygen species (ROS) which is generated by cells.

15. The method according to claim 1, wherein the method is performed in an aqueous solution.

16. The method according to claim 1, wherein the method is performed at a pH ranging from about 3 to about 11.

17. The method according to claim 1, wherein the first agent is contacted with the activation signal at most 10 minutes after contacting the first agent with the second agent.

18. The method according to claim 1, wherein the first agent is a peptide.

19. The method according to claim 1, wherein the method is performed at a pH ranging from about 4 to about 8.

20. The method according to claim 1, wherein the activation signal activates the furan moiety of said first agent to an intermediate comprising a hydroxy-hydroperoxy moiety and/or an intermediate comprising a keto-enal moiety or a (2,5-dihydroxy-2H-furan-5-yl)-moiety.

21. The method according to claim 1, wherein the method is performed at physiological conditions.

* * * * *